United States Patent [19]
Herren et al.

[11] Patent Number: 6,108,635
[45] Date of Patent: Aug. 22, 2000

[54] INTEGRATED DISEASE INFORMATION SYSTEM

[75] Inventors: L. Tandy Herren; Pamela K. Fink; Kenneth S. Kornman; Christopher J. Moehle, all of San Antonio, Tex.; Debra J. Moore, Cincinnati, Ohio

[73] Assignee: Interleukin Genetics, Inc., San Antonio, Tex.

[21] Appl. No.: 08/858,200

[22] Filed: Apr. 30, 1997

Related U.S. Application Data

[63] Continuation-in-part of application No. 08/651,554, May 22, 1996, abandoned.

[51] Int. Cl.$^7$ .................................................... G06F 17/60
[52] U.S. Cl. ...................... 705/2; 705/3; 705/4; 600/300
[58] Field of Search ....................... 705/2, 3, 4; 600/300; 364/578; 128/200.3; 530/391.7

[56] References Cited

U.S. PATENT DOCUMENTS

| | | |
|---|---|---|
| 3,833,796 | 9/1974 | Fetner et al. . |
| 4,315,309 | 2/1982 | Coli .................................................. 705/3 |
| 4,858,121 | 8/1989 | Barber et al. ................................. 705/2 |

(List continued on next page.)

FOREIGN PATENT DOCUMENTS

| | | | |
|---|---|---|---|
| 0 813 155 A1 | 12/1997 | European Pat. Off. . | |
| WO 92/04860 | 4/1992 | WIPO ............................... A61B 5/00 |
| WO 94/00817 | 1/1994 | WIPO .............................. G06F 15/00 |
| WO 96/32684 | 10/1996 | WIPO .............................. G06F 17/18 |
| WO 98/022837 | 1/1998 | WIPO .............................. G06F 19/00 |

OTHER PUBLICATIONS

Chandrasekaran, B., "On Evaluating Al Systems for Medical Diagnosis", The Al Magazine, pp. 34–37, Summer 1983.

Clancey, W. J., "Viewing Knowledge Bases as Qualitative Models", IEEE Expert, pp. 10–23, Summer 1989.

Dalton, J. T., Wientjes, M. G. and Au, J. L., "Effects of Bladder Resorption on Pharmacokinetic Data Analysis", Journal of Pharmacokinetics & Biopharmaceutics, vol. 22, No. 3, pp. 183–205, 1994.

(List continued on next page.)

*Primary Examiner*—Allen R. MacDonald
*Assistant Examiner*—M. Irshadullah
*Attorney, Agent, or Firm*—Fenwick & West LLP

[57] ABSTRACT

A system including a set of software based Explorers, and a computer assisted methodology support the development of new medical interventions for diseases. The system includes Explorer modules for discovering proposed interventions, designing clinical trials, performing pharmacoeconomic analysis, and illustrating disease progression for various patients over time including creating disease progression tutorials for patients. The Explorers support a bottom-up or data driven methodology that enables a user, such as medical researcher, to mine data sources of clinical, biologic, expert or other types of data to discover, test, evaluate, and understand a proposed intervention and its impact on disease progression in different patient types. A Target Discovery Explorer assists the user in identifying leverage points in disease progression in relationship to various patient attributes and interventions, thereby identifying a proposed intervention for the desease. A Clinical Trials Explorer assists the user in designing clinical trials based through identification of combinations of patient attributes and intervention attributes that yield efficacious changes in selected disease progression measures. A Pharmacoeconomic Explorer enables the user to determine relative costs-benefits of a proposed intervention for patients, practitioners, and payers, including quality of life results for patients, practice results for practitioners, and financial payment results for payers. A Disease Progression Explorer enables the user to visually project disease progression for specified patient attributes and interventions, in order to better understand and explain the effects of an intervention on a disease for such patients and their practitioners, and to select disease progression tutorials that are directed to the specific patient attributes and their corresponding effect on disease progression over time.

65 Claims, 36 Drawing Sheets

U.S. PATENT DOCUMENTS

| | | | |
|---|---|---|---|
| 4,881,175 | 11/1989 | Ladner | 705/138 |
| 5,005,143 | 4/1991 | Altschuler et al. | |
| 5,019,998 | 5/1991 | Cowan et al. | |
| 5,025,388 | 6/1991 | Cramer, III et al. | |
| 5,081,584 | 1/1992 | Omichinski et al. | |
| 5,260,882 | 11/1993 | Blanco et al. | |
| 5,331,573 | 7/1994 | Balaji et al. | |
| 5,517,405 | 5/1996 | McAndrew et al. | 705/45 |
| 5,526,281 | 6/1996 | Chapman et al. | 705/22 |
| 5,545,721 | 8/1996 | Carrol et al. | 530/391.7 |
| 5,557,514 | 9/1996 | Seare et al. | 705/2 |
| 5,642,731 | 7/1997 | Kehr | 600/300 |
| 5,657,255 | 8/1997 | Fink et al. | 364/578 |
| 5,676,129 | 10/1997 | Rocci, Jr. et al. | 128/200.3 |
| 5,713,350 | 2/1998 | Yokota et al. | 600/300 |

OTHER PUBLICATIONS

Discovery And Representation of Casual Relationships fro a Large Time–Oriented Clinical Database: The TRX Project, Apr. 1981.

Eas MA: A program for the meta–analysis of clinical trials, Computer Methods and Programs in Biomedicine, vol. 53, No. 3, Jul. 1997.

EON: A Component–Based Approach of Protocol–Directed Theory, JAMIA, vol. 3, No. 6, Nov. 1996.

A Perspective on the role of decision analysis in clinical practice, 1986.

Fink, P.K. and Herren, L.T., "Modeling Disease Processes for Drug Development: Bridging the Gap Between Quantitative and Heuristic Models", 1996 Winter Simulation Conference Proceedings, Dec. 8–11, 1996, pp. 1183–1190, XP002076640, San Diego, California.

Klinger, D.E., Jaffe, M.E., "An Information Technology Architecture for Pharmaceutical Research and Development", Fourteenth Annual Symposium on Computer Applications in Medical Care, Nov. 4–7, 1990, pp. 256–260, XP002076642, Washington, D.C.

Leff, C.F., "Building An Automated Manpower–Estimating System", Proceedings of the 20$^{th}$ Annual Seminar/Symposium—Project Management Institute, Sep. 17–21, 1988, pp. 517–520, XP002076639, Drexel Hill, Pennsylvania.

Rosenberg, M.J., "ClinAccess: An Integrated Client/Server Approach to Clinical Data Management and Regulatory Approval", Proceedings of 21$^s$ Annual SAS Users Group International Conference, Mar. 10–13, 1996, XP002076641, Cary, North Carolina.

Baclawski, K., and Fridman, N., "M&M–Query: Database Support for the Annotation and Retrieval of Biological Research Articles", Technical Report NU–CSS–94–07, Northeastern University, College of Computer Science, 1994.

Baclawski, K., Futrelle, R., Fridman, N., and Pescitelli, M., "Database Techniques for Biological Materials and Methods", Proceedings of the 1$^{st}$ International Conference on Intelligent Systems for Molecular Biology, pp. 21–28, Jul. 1993.

Fink, P. K. and Lusth, J. C., "Expert Systems and Diagnostic Expertise in the Mechanical and Electrical Domains", IEEE Transactions on Systems, Man, and Cybernetics, vol. SMC–17, No. 3., pp. 340–349, May/Jun. 1987.

Fishwick P. A., "Qualitative methodology in simulation model engineering", Simulation vol. 52, No. 3, pp. 95–101, Mar. 1989.

Miller, R. A., Pople, Jr., H. E., and Myers, J.D., "*Internist–I*, an Experimental Computer–Based Diagnostic Consultant for General Internal Medicine", The New England Journal of Medicine, vol. 307, No. 8, pp. 468–476, Aug. 19, 1982.

Patil, R. S., Szolovits, P. and Schwartz, W. B., "Causal Understanding of Patient Illness in Medical Diagnosis", IJCAI, pp. 893–899, 1981.

Rieger, C. and Grinberg, M., "The Declarative Representation and Procedural Simulation of Causality in Physical Mechanisms", Knowledge Repr.–4: Rieger, pp. 250–256.

Robertson, M. J., Dougall, I. G., Harper, D., McKechnie K. C. W. and Leff, P., "Agonist–antagonist interactions at angiotensin receptors: application of a two–state receptor model", Trends in Pharmacological Sciences, vol. 15, No. 10, pp. 364–369, Oct., 1994.

Shortliffe, Ph.D., E. H., "Computer–Based Medical Consultations: MYCIN", Artificial Intelligence Series, Chapter 1, pp. 1–55.

Sieburg, H. B. and Müller–Sieburg, C., "The CyberMensch Simulation Server for the Planning of Clinical Trials", Interactive Technology and the New Paradigm for Healthcare, Chapter 65, pp. 445–454, 1995.

Sieburg, H. B., "*In Silico* Environments Augment Clinical Trials", 4527 IEEE Engineering in Medicine and Biology, vol. 15, No. 2, pp. 47–59, Mar./Apr., 1996.

Sieburg, H. B., "Methods in the Virtual Wetlab I: Rule–based reasoning driven by nearest–neighbor lattice dynamics", Artificial Intelligence in Medicine, vol. 6, No. 4, pp. 301–319, Aug., 1994.

Uckun, S., "Model–Based Reasoning in Biomedicine", Critical Reviews in Biomedical Engineering, vol. 19(4), pp. 261–292, 1992.

Waterman, D. A., "Catalog of Expert Systems", A Guide to Expert Systems, pp. 244–329.

Weiss, S. M., Kulikowski, C. A., and Amarel S., "A Model–Based Method for Computer–Aided Medical Decision–Making", Artificial Intelligence, vol. 11, pp. 145–172, 1978.

FIG. 12a

Treatment Regimen
File Run View

PROPOSED INTERVENTION

| | |
|---|---|
| Drug Therapy | estrogen replacement ▽ |
| Dose Concentration | 0.1 mg ▽ |
| Doses per Day | 1 ▽ |
| *Refill Schedule* | every six months ▽ |
| Subject Compliance | 95 |

TREATMENT CYCLE

| | |
|---|---|
| Treatment Start | age 60 |
| Length of Treatment Cycle | 5 years |
| Cycles per Year | none |

☐ Decline a custom treatment pattern

123 →

Back    Continue

*FIG. 12b*

Practice Description

File  Run  View

Describe the Gynecology Practice:

Practice Volume

Number of Patients Treated Daily: 25

Number of Patients in Practice: 400

Percentage of Osteoporosis Treatment: 19

Principle Coverage of Patients in Practice

Percentage Indemnity: 38

Percentage Managed Care: 32

Percentage Capitation: 27

Percentage Self Paid: 3

Describe the Patient: — 213

Level of Cosmetic Concern: moderate

Employment Status: nonexempt

Posture Affected: ○ Yes  ○ No

Mobility Affected: ○ Yes  ● No

Likelihood of Insurance paying for New Therapy: 25 — 217

[Execute Study]

Please enter the level of the patient's cosmetic concern.

INTEGRATED DISEASE INFORMATION SYSTEM

CROSS REFERENCE TO RELATED APPLICATIONS

This application is a continuation in part of Ser. No. 08/651,554, entitled "Pharmaceutical Process System for Creating and Analyzing Information," filed on May 22, 1996.

COPYRIGHT NOTIFICATION

Portions of this patent application contain materials that are subject to copyright protection. The copyright owner has no objection to facsimile reproduction of the patent document or the patent disclosure by anyone, as it appears in the Patent and Trademark Office patent file or records, but otherwise reserves all copyright rights whatsoever.

FIELD OF THE INVENTION

The present invention relates to computer-based systems for disease information input, analysis, and output. In particular, the invention relates generally to systems for developing new therapies, tests, devices, regimens, or other interventions for biological systems and more particularly to systems providing integrated management and analysis of multiple data sources of biological, patient, or population data in developing new interventions.

BACKGROUND OF THE INVENTION

New therapy and medical test (hereafter "intervention") development is extremely speculative. In order to bring a new intervention to market, numerous hurdles must be overcome. Each hurdle involves gaining knowledge about how the intervention works, under what situations it works, and whether or not it is safe. The major hurdles in development are discovering a proposed intervention, testing it in a human population, determining whether its effect produces a significant improvement over other interventions for a given disease, and finally, educating practitioners and patients about its benefit and appropriate use. Each of these hurdles requires the generation, collection, and analysis of a large amount of data to test hypotheses about the proposed intervention, i.e., whether or not it is effective; for which patients it is most effective; and whether or not it is an improvement over standard interventions for the same disease. The system described in this application was developed to help researchers achieve each of these major hurdles.

The development of interventions consists of four identifiable stages: target discovery, clinical trial design, pharmacoeconomic assessment, and product distribution/use. Target discovery is the process of finding a biological or cellular mechanism in the biology of the disease process that, if affected or known through testing, alters the course of disease progression. Target discovery identifies both the particular target in the disease biology and the intervention that affects or identifies the target. The pathology of a disease is often so complex that it takes years of research to discover a target leverage point that provides a cure or at least relieves the symptoms. This is clearly one of the most difficult problems facing pharmaceutical research. It is a very labor-intensive and time-consuming stage in which a positive outcome is not assured. It relies on discovering an insight, which happens in due course rather than on a fixed schedule.

Current approaches to target discovery concentrate on standard laboratory experimentation to generate hypotheses and animal trials to further evaluate those hypotheses. These standard approaches are often limited by the knowledge and understanding that the researchers have of the disease biology. Researchers bring to the design of their studies a paradigm or guiding theory that directs the questions they seek to answer. While this top-down approach to target discovery can be very successful if the theory is good, it begs the question of how to develop a theory in the first place. In the absence of a guiding theory, researchers must cull through large bodies of data to develop an initial insight. There are few tools and no standard approaches that support this bottom-up, or data-driven approach to target discovery and the identification of proposed interventions.

The next stage in intervention development involves designing and conducting formal clinical trials of the proposed intervention. Clinical trials typically isolate narrowly on a single variable, e.g., the proposed intervention, and use a control group as a baseline from which the variable is measured. Observations from a clinical trial attempt to draw conclusions from statistical differences between the control and experimental groups. Because of the enormous expense of conducting trials large enough to statistically assess a broad range of variables, these observations often fail to take into account the multivariate, dynamic nature of the patients individually or as a group.

Clinical trials are very data intensive, time-consuming and costly. The goal is to gather enough evidence to support the claims of the intervention's efficacy and to obtain regulatory approval. A typical cycle for a clinical trial may take several years. For example, designing the trial may take six months, performing the trial may take a year, and analyzing the results may take yet another six months. After years of testing, the results may still be unexpected or difficult to interpret.

The design of a clinical trial is limited by the researchers' knowledge of the underlying disease process, how patient attributes affect it, and how the proposed intervention, the disease biology, and the patient attributes interact. Without this knowledge, designers might test patient types for which the intervention is ineffective or has adverse effects. Additionally, they might design an inappropriate regimen for delivering the proposed intervention. Either of these alternatives could lead the research team to conclude that a proposed intervention has no effect, when in fact it is very effective for the right patients with the correct delivery schedule. Alternatively, without this knowledge, a positive clinical trial might lead the research team to conclude that a proposed intervention has a profound effect without a full understanding of the possible limitations.

Much research is underway to develop tools to support the clinical trial design process. Most of these tools concentrate on analyzing the merit of alternative designs given the researchers' assumptions about the pharmacokinetics and pharmacodynamics of an intervention. Given the appropriate assumptions, these tools help the researchers assess the risks of the clinical trial design, select the appropriate dose requirements, and reveal the statistical characteristics of the proposed study. Thus, researchers must have considerable prior knowledge of the intervention effects, including knowledge of the effects of the intervention on the disease biology and of the efficacy of alternative regimens for delivering the intervention at the biological level. They take the effects of the intervention on different patient types as a given, and proceed to evaluate competing clinical trial designs for their statistical power. Again, this approach is based only on a top-down methodology that does not support clinical trial design by exploration of biological effects of a proposed intervention on patient types. No currently available tools support the development of clinical trial design by a data driven analysis of the patient attributes which are efficaciously effected by a proposed intervention.

The third stage in the development of interventions, pharmacoeconomic analysis, involves analyzing the benefits of the proposed intervention relative to standard, existing interventions. The pharmaceutical industry is still grappling with how to adequately evaluate the pharmacoeconomic benefit of a potential product and there are no established methods for conducting pharmacoeconomic analysis. Many pharmaceutical companies, as well as the FDA, recognize the need to establish standard procedures for generating claims about the relative effectiveness of competing products, but the methodologies that have been used are extremely expensive, involving comparative clinical trials. To date, methods of evaluating relative clinical outcomes and quantifying quality of life differences between competing intervention scenarios have not been rigorously formalized. The computational methodologies that do exist involve mining large databases of clinical use data to find patterns that can support effectiveness claims. However, these are post hoc approaches; there are no standards for estimating pharmacoeconomic value during the intervention development process. As a result, companies may invest a large amount of money bringing a product to market that cannot achieve an adequate market share to justify the development expense.

The final stage in the development of interventions is product distribution and use. This process involves bringing knowledge and information about the new intervention to the practitioners and patients in order to educate them about the processes underlying the disease, the expected changes in the patient's manifestation of the disease over time (i.e., the disease progression), and the effects of alternative interventions in the disease progression and the patient's overall outcome, including the patient's resulting quality of life and cost. This process draws on the data that supported the target discovery, clinical trials, and pharmacoeconomic analyses to help practitioners and patients make informed decisions about the use of the product.

Traditional approaches to product distribution include developing brochures and pamphlets that present the benefits of the new product and discuss its use. These approaches emphasize the new product and seldom offer unbiased comparisons to existing methods and practices. In addition, companies seldom develop materials to support patient education. However, automated support for practitioner education that clearly presents the disease progression over time for specific patient attributes, and further shows the benefits and limitations of a new intervention is not now currently available. Without automated support for this process that combines and synthesizes all sources of existing data into a meaningful clinical interpretation of estimated disease progression for a specific patient over time and that provides a comparison with existing intervention practices, companies are handicapped in their ability to explain the benefits of their new intervention to potential users and to indicate when it is most effective. Thus, it is difficult to bring the new product to the appropriate constituencies.

A need clearly exists to support, speed, and improve the four major stages of developing disease interventions. The present invention overcomes prior limitations by supporting the collection, storage, and analysis of the data targeted at each of the major hurdles in the development process from discovery to commercialization. The outcome achieved by the present invention aids the discovery of proposed interventions to support therapies and/or medical tests, the design of relevant clinical trials for the proposed intervention, a comparison of the benefits of the proposed intervention to existing practices, and the education of patients and practitioners in the appropriate use of the new intervention to support product commercialization.

SUMMARY OF THE INVENTION

The present invention, as embodied in the Integrated Disease Information System, supports, speeds, and improves the four major stages in the development of interventions. Users of the system may reap large financial benefits because the system streamlines the process of searching for a suitable intervention, designing clinical trials, evaluating the potential market and consumer benefits of the proposed intervention over current methods and practices, and designing marketing, sales, and educational aids for practitioners providing the proposed intervention and patients receiving it.

The dynamic, computer-based system of the present invention receives user provided, or database stored data relating to biological parameters, disease measures, patient characteristics, analyzes biological findings and hypotheses, and outputs the results of the analyses to support identification of targets and interventions, the design of clinical trials, the pharmacoeconomic analysis of interventions, and the presentation of disease progression information. The analyses may be based on data generated by models that simulate the disease process at the cellular and subcellular levels. The analyses may also be based on other sources of data, such a legacy databases, clinical trials, and expert knowledge. The present invention provides an interface to assist in identifying proposed interventions, developing a better understanding of key biological mechanisms, assessing the potential for influencing important clinical outcomes, evaluating the pharmacoeconomic benefit of the proposed intervention, and projecting disease outcomes across time under various intervention scenarios with varying risk factors.

The Integrated Disease Information System embodies an architectural framework that supports the entire intervention development process. This framework not only divides the development effort into four discrete steps (target discovery, clinical trial design, pharmacoeconomic analysis, and product commercialization and education), but also provides a unique methodological approach to performing each of the steps.

Target discovery and clinical trial design can both be conceptualized within an experimental paradigm. Experiments enable a researcher to discover a proposed intervention, and a clinical trial is an experiment to test the efficacy of the proposed intervention. Conventionally, researchers approach these tasks in a top-down manner, using a theory or other governing principle to direct the search for an intervention and design a clinical trial. The Integrated Disease Information System inverts the process and replaces it with a bottom-up or data-driven approach that enables the user to efficiently explore and discover complex relationships between patient attributes, biological parameters, disease progression measures, and intervention attributes. The Integrated Disease Information System provides the user a method of examining a large amount of data to support target discovery and clinical trial design.

In one embodiment, the Integrated Disease Information System provides four primary modules, called Explorers, which assist the user in understanding disease progression, identifying interventions, designing clinical trials, and developing disease progression educational information. The system is coupled to various types of data sources, such as expert systems, simulation environments, clinical data, and the like. Each of the Explorers supports a data driven exploration of their respective application areas, allowing a user of the system to explore the relationships between various patient attributes, intervention attributes, biologic parameters, and other data in the data sources. This exploratory approach to intervention development results in reduced costs and development to the intervention developer, along with increased capacity to demonstrate the efficacy of an intervention to various constituents, including payers, practitioners, and patients.

With respect to identification of targets and proposed intervention, the present invention provides a data driven methodology for identification of targets and interventions, and a Target Discovery Explorer that supports the methodology. To perform target discovery, the user of the system need not create any models of disease progression or intervention operation at a cellular or biologic level. Rather, this information is directly or indirectly captured in the underlying data sources, such as through knowledge acquisition from experts in the relevant medical or biological field as embodied in an expert system, literature databases, clinical trial databases, simulation modeling, or the like. The user queries these data sources with variations in patient attributes, biologic parameters, intervention attributes. These various inputs are processed against the various appropriate data sources, to provide to the user outputs indicating resulting changes in disease progression parameters associated with the disease progression. The user explores the biologic parameters, patient attributes, and intervention attributes in this manner to identify a proposed intervention that efficaciously affects the disease progression, or measures the disease progression.

The Target Discovery Explorer supports this methodology by providing a Biologic Manipulation Tool that receives the various user inputs and queries the data sources and determines the resulting changes in the disease progression, and a Biologic Change Evaluation Facility that provides various forms of visualization of the resulting changes in disease progression.

In supporting clinical trial design, the present invention differs substantially from conventional approaches in that it helps researchers to develop information about the effects of a proposed intervention at the biological level (e.g., what patient types exhibit the best response to which form of intervention). The present invention enables researchers to evaluate how patient attributes affect the impact of the intervention at the biological level. The biological information is used to develop a proposed clinical trial design in terms of the patient types that should be included in a clinical trial and the attributes of the patient or intervention that need to be controlled for in the clinical trial design. More particularly, the present invention enables the user to select various combinations of biological parameters, patient attributes, and intervention attributes, apply these selections to the underlying data sources to determine which combinations of parameters and attributes are demonstrative of the efficacy of the intervention. In this manner, the user can determine the impact of various clinical trial designs prior to actual implementation of the clinical trial, to determine the likelihood of useful results. In contrast, in conventional clinical trial design, the biological parameters, patient attributes and intervention attributes are assumed, instead of being analyzed as part of the clinical trial design itself. By providing a data driven exploration of the alternative clinical trial design factors, the present invention enables a user to effectively identify attributes for inclusion in a clinical trial, and attributes which are not useful to test. This yields increased value in the clinical trial results, faster clinical trial design, and reduced costs.

The Integrated Disease Information System embodiment of the present invention supports clinical trial design with a Clinical Trials Explorer, including a Patient Type Efficacy module and a Clinical Trial Design module. The Patient Type Efficacy module is for determining the impact of an intervention on a specific patient type. The module receives user inputs of a specific combination of patient attributes, intervention attributes and biologic parameters, queries the data sources, and displays the resulting effects on the disease progression from the combination of factors. The Clinical Trial Design module is for comparing the disease progression for various types of patients that are to be part of a potential clinical design. This module takes as inputs the various combinations of patient attributes to be studied and the proposed intervention, and simulates the disease progression for the various groups over time given the intervention. This enables the user to compare the efficacy of an intervention with existing standard interventions.

The present invention supports pharmacoeconomic analysis on two levels. First, it provides a method for collecting and representing expert knowledge about how to determine the relative benefit of a proposed intervention for three different groups, the patient, the practitioner, and the payer or insurer, and it recognizes that a proposed intervention should be beneficial for each of the groups in order to be successful. Secondly, it provides a method for encoding the expert knowledge and using it to calculate the pharmacoeconomic benefit of the proposed intervention. The Integrated Disease Information System embodiment of the present invention uses these underlying sources of data, and enables the user to determine the relative cost-benefits of a proposed intervention relative to standard interventions, as a function of payer attributes such as patient quality of life and participation factors, and practitioner attributes for practitioners providing the proposed intervention, such as practice type and size, and insurance coverage, and payer attributes, such as intervention costs, and future intervention requirements.

In application, the user provides to the system various inputs for these attributes, and the system determines, either qualitatively or quantitatively, outcomes for these various constituents under both the proposed intervention and under standard inventions. This information enables the user to evaluate the commercialization aspects of a proposed intervention. In the Integrated Disease Information System embodiment, the present invention provides this functionality in a Pharmacoeconomic Explorer that includes a Patient Outcome Analysis module, a Practitioner Outcome Analysis module, and a Payer Outcome Analysis module.

Finally, the Integrated Disease Information System conceptualizes product commercialization as a process of patient and practitioner education of the disease progression, and particularly disease progression as impacted by the proposed intervention, standard interventions, or no intervention at all, and the particular attributes of patient type. This approach differs from traditional approaches employed in marketing materials, which are static and emphasize only a single product, and do so without taking account of specific patient attributes. The approach used by the Integrated Disease Information System is not designed as a sales technique or mere marketing literature. Instead, it enables the creation of a disease progression tutorial of information for practitioners or patients about the effects of the proposed intervention on the disease progression, in terms of the underlying biology of the disease process and a comparison with existing interventions. It also supports the practitioner in developing a good mental model of the relative outcomes of alternative interventions for a specific patient. And, it provides the practitioner with a good understanding of the relative pharmacoeconomic benefit to the patient in terms of cost and overall quality of life. Patients receive a clear understanding of the likely outcomes of alternative courses of intervention. They receive an explanation that supports their decision making process by providing them an appropriate representation of this disease process and how an intervention would affect it. Finally, the Integrated Disease Information System provides patients an understanding of the relative benefits of alternative interventions in terms of cost and quality of life.

The present invention supports these features by enabling a user to input patient attributes for a specific patient type, intervention attributes, and a relevant time period for determining the disease progression. These various attributes are used to query the underlying data source that captures disease progression information for various patient attributes, and at different stages of disease progression. This information is dynamically used to model the disease progression over time for the specific patient, such as showing changes in various disease progression measures, and graphically illustrating, either through charts, plots, or anatomical representations, the disease progression over time. In this way, a practitioner can demonstrate to a patient the disease progression that patient will experience both with and without an intervention, thereby improving the patient's and the practitioner's understanding to the disease progression in that patient.

The Integrated Disease Information System embodiment of the present invention supports creation of disease progression information in this way through a Disease Progression Explorer that includes a Patient History module, a Disease Progression Evaluation module, and Disease Progression Tutorials. The Patient History module receives user inputs of the specific patient attributes, and intervention attributes (if any) to be projected for a disease, and queries the data sources for disease progression measures that result from the specified inputs. The Disease Progression Evaluation module uses the resulting disease progression measures, and projects these measures onto various graphical or anatomical representations, thereby showing the specific effects of the disease on the patient. The Disease Progression Tutorials are used to provide background tutorial information on the biology of a disease and mechanism of an intervention.

The various methodological aspects of the invention, along with their various embodiments in the individual Explorers, can be used in isolation or in various combinations, thereby further increasing their utility to different classes of users. For example, a pharmaceutical company which has a proposed intervention under development, may use just the Clinical Trials module to explore the factors of attributes desirable for inclusion in a clinical trial, without using the Target Discovery Explorer to identify an intervention (since it already has one). Alternatively, the company may have already developed a model of disease biology in the form of an expert system or simulation model, and couple this data source to the Target Discovery Explorer to explore this model to identify a target in the biology and a proposed intervention to effect or measure that target. Alternatively, a company which already has identified a proposed intervention and seeks to market it, may use the Pharmacoeconomic Explorer to demonstrate to payers that the proposed intervention is more cost effective than standard interventions, and thereby should be included in their treatment plans and insurance plans. This type of company may provide the Disease Progression Explorer to practitioners so as to enable them to understand the disease progression as impacted by its proposed intervention, and as compared to standard interventions (or no intervention at all), and also to enable the practitioners to use the Disease Progression Explorer with their individual patients to educate such patients. Thus, the various uses and implementations of present invention can be beneficially employed by themselves, or may be combined into an integrated system and method.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 12*a* and FIG. 12*b* show examples of the graphical user interface for the Patient Type Efficacy Module;

FIG. 21 provides an example user interface that receives data/information about the patient and practitioner to support the pharmacoeconomic analysis;

DETAILED DESCRIPTION OF A PREFERRED EMBODIMENT

Figure 1:
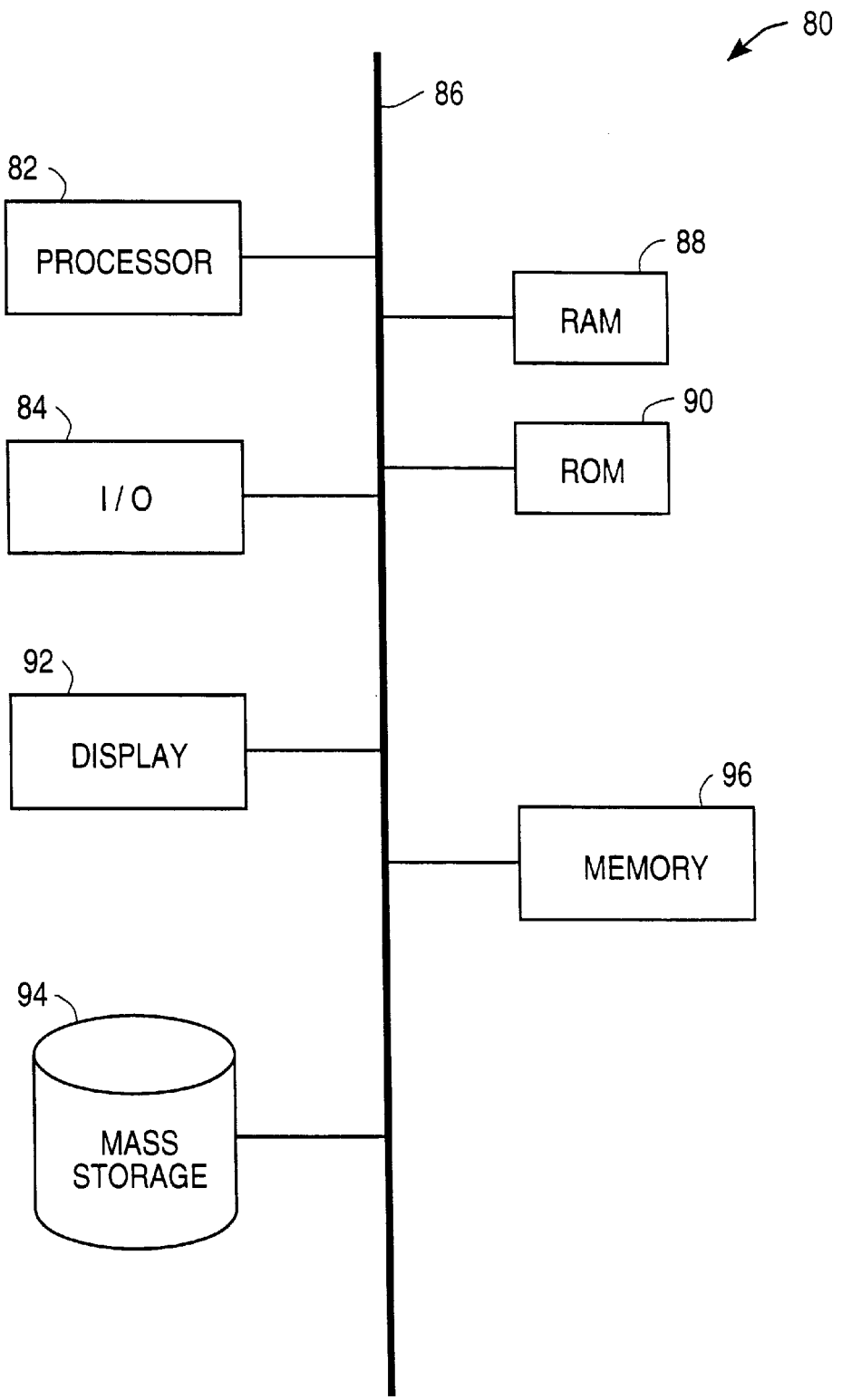
FIG. 1 shows an architecture that may be used to implement the apparatus and methods defined by the present invention.

A detailed description of a preferred embodiment of the present invention is disclosed herein. It should be understood, however, that the disclosed embodiment is merely exemplary of the invention, which may be embodied in various forms and functions. Therefore, the details disclosed herein are not to be interpreted as limiting, but merely as the basis for teaching one embodiment of the invention.

It should be understood that, as used herein, the meaning of the term "interface" is not limited to a graphical user interface. Rather, the term, as used herein, is intended to broadly refer to an interface between a user and other computer system components, as well as between such components and other applications. Such an interface may include a graphical user interface as well as software and hardware components internal to the system that do not directly interact with the user.

OVERVIEW

The Integrated Disease Information System, described in detail below, assists a user in overcoming four principle hurdles in the intervention development process: 1) drug, device, regimen, or test (hereafter collectively referred to as "interventions") discovery; 2) clinical trial design; 3) pharmacoeconomic analysis; and 4) disease progression analysis in support of practitioner and patient education, and product commercialization. These functions are critical steps in the process of bringing a new product to market.

Intervention discovery addresses the issue of identifying key manipulation points in the biology of a disease that will halt or alter its progression for the purpose of developing a proposed test, device, regimen, drug, or other therapeutic regimen. A clinical trial answers the question of whether the proposed intervention has an effect on a selected disease process. The answer to this question may result in a qualified "yes," in which the intervention has varied levels of efficacy for different types of patients. Pharmacoeconomic analysis compares the proposed intervention to current standard practice for treating the disease or testing for risk factors in order to determine whether there is any advantage to the new intervention in terms of improved disease progression and/or cost and patient quality of life. Pharmacoeconomic evaluation in accordance with the present invention uses expert knowledge to evaluate a proposed intervention in relation to existing products or procedures to determine outcomes for medical providers, patients, and insurance providers. Disease progression analysis draws on data to project the course of the disease over time for different combinations of patient risk factors and/or various therapeutic regimens. This analysis helps practitioners and patients understand the best use of the new intervention for the patient. The Integrated Disease Information System disclosed herein includes a set of tools that support target discovery, clinical trial design, pharmacoeconomic analysis, and disease progression analysis.

INTEGRATED DISEASE INFORMATION SYSTEM ARCHITECTURE

Figure 2:
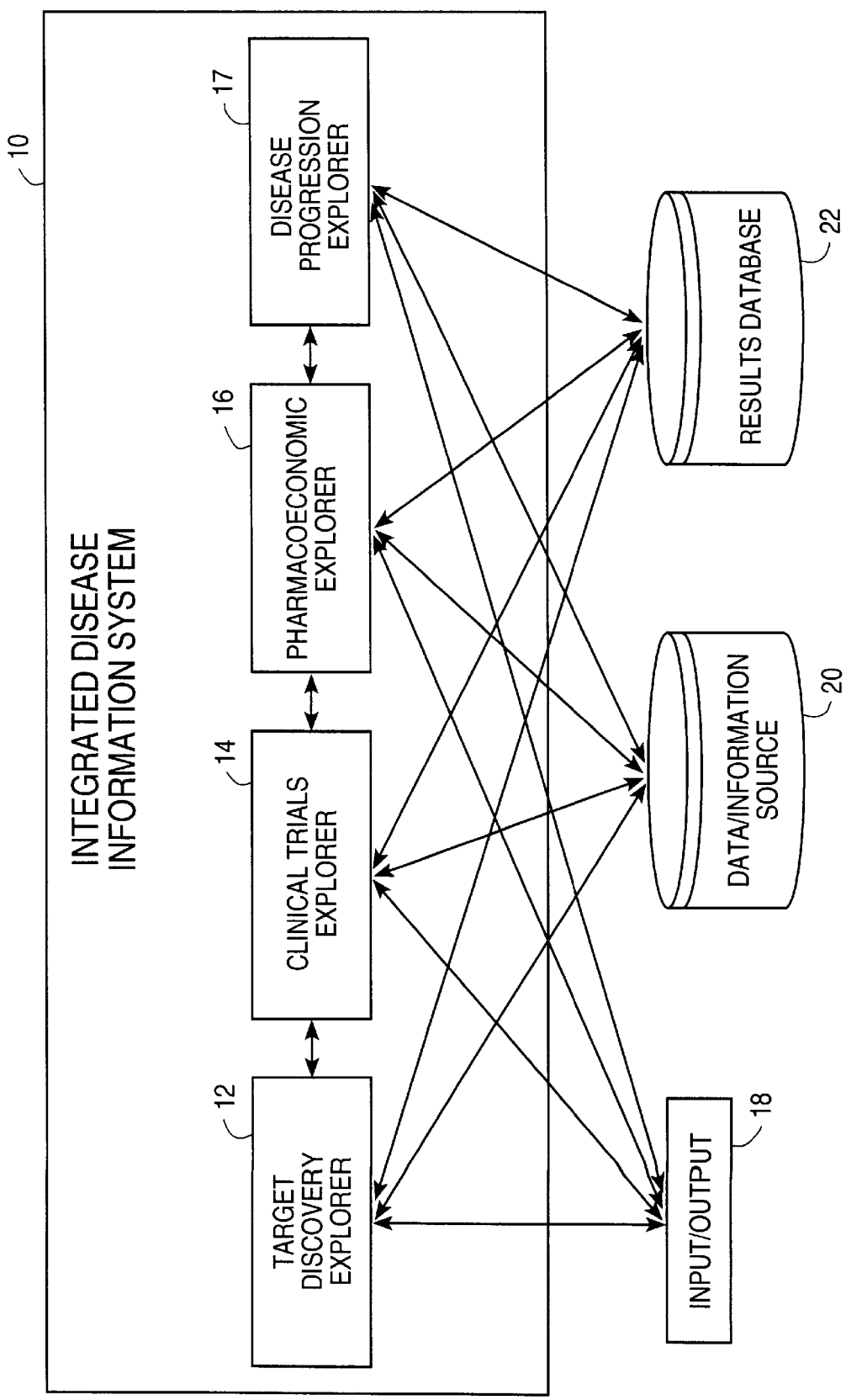
FIG. 2 is a block diagram showing the Integrated Disease Information System in accordance with the present invention.

FIG. 2 is a block diagram showing the Integrated Disease Information System 10 in accordance with the present invention. The Integrated Disease Information System integrates data received from Input/Output 18, Data/Information Source 20, and Results Database 22 to provide reliably appraised data of a desired biological system. Integrated Disease Information System 10 is comprised of four system components: Target Discovery Explorer 12, Clinical Trials Explorer 14, Pharmacoeconomic (PE) Explorer 16, and Disease Progression Explorer 17. These system components communicate with each other. They exchange data and other information, as indicated by the bidirectional arrows. The particular implementation of communication between software components will vary considerably depending on the software and hardware utilized with specific applications of the present invention.

Target Discovery Explorer 12 processes data and information from Data/Information Source 20 and Input/Output 18 to support discovery of a potential intervention. It stores the results of the analysis in Results Database 22, making it available to Clinical Trials Explorer 14 for analysis. Alternatively, it could send the results directly to Clinical Trials Explorer 14. Clinical Trials Explorer 14, using the data developed by Target Discovery Explorer 12 and additional data as necessary and available, develops data to compare the proposed intervention in patients with different attributes and risk factors under different intervention regimens. The proposed intervention is compared to results achieved through no therapy (placebo) or alternative interventions and across different patient risk factor profiles. The patient information developed by Target Discovery Explorer 12 and Clinical Trials Explorer 14 is made available to PE Explorer 16, either directly or via Results Database 22, to develop further data and assess differences between a proposed intervention and current standard treatments or testing practices. The information developed by Target Discovery Explorer 12, Clinical Trials Explorer 14, and PE Explorer 16 is transferred to Disease Progression Explorer 17 to project the course of the disease across time on an appropriate graphical representation for various patient risk attributes and alternative interventions.

It should be understood that a person is involved in each step of the process provided by the present invention. The system does not function entirely by itself; that is, decisions regarding a variety of parameters are input by an individual and the system uses the parameters to generate and display data and information to facilitate the decision making process of the individual. The user interacts with each software component to select variables of interest for analysis. The Explorers convert the user's input into an appropriate query of the data source(s) and retrieve the results of the query. The user then selects how to view the retrieved information from a set of predefined options. These options are specific to each Explorer and support the user in the corresponding task. Each Explorer manipulates and integrates the data and displays it to the user in the selected fashion. The user makes conceptual judgments regarding substantive issues and provides parameters to the system to retrieve, compare, and analyze the results. Users can select variables and views any number of times in support of their decision making task. One of the benefits the invention provides is a fully integrated system for extracting, manipulating, and analyzing data from various sources in support of each of the steps of intervention development.

It is also contemplated that Explorers 12, 14, 16, and 17 could communicate data and information by buffering it in either Data/Information Source 20 or Results Database 22 as well as directly. Each Explorer develops a particular type of data that can in turn be used by a system user or another Explorer. Each Explorer can also obtain the data necessary for operation from an appropriate data source in addition to or instead of from another Explorer. It should also be kept in mind that FIG. 2 is intended to show a broad overview of the Integrated Disease Information System and that the specifics of the system may be varied without departing from the spirit of the present invention.

FIG. 1 shows an example computer architecture on which the Integrated Disease Information System 10 may be implemented. The Integrated Disease Information System may be implemented on any standard computing platform that includes a processor 82, input/output device 18, display device 92, random access memory 88, and memory storage 96. It is implemented as a program that runs on standard system software, including an operating system. It can be implemented using a variety of standard computer languages, development tools, database tools, and graphical user interface development tools as needed to implement the functions disclosed herein.

The components of Integrated Disease Information System 10 communicate with Input/Output 18. Input/Output 18 may include, but is not limited to, video displays, mice, modems, keyboards, light pens, joysticks, and communication adapters. Input/Output 18 represents any device capable of exchanging information between a user and Integrated Disease Information System 10. Each of Target Discovery Explorer 12, Clinical Trials Explorer 14, PE Explorer 16, and Disease Progression Explorer 17 receives information from and sends information to Input/Output 18.

The components of Integrated Disease Information System 10 also communicate with Data/Information Source 20. Data/Information Source 20 (discussed in detail below) stores the data and information used by Target Discovery Explorer 12, Clinical Trials Explorer 14, PE Explorer 16, and Disease Progression Explorer 17 in creating and analyzing biological data and information. Data/Information Source 20 stores "source" data and information. "Source" data and information are collected by the user of the system or another outside source. This data may include, but is not limited to, experimental data, standard clinical trial data, practice-based data, expert opinion/knowledge, simulation results, or other sources of relevant data and/or information.

Finally, the components of Integrated Disease Information System 10 communicate with Results Database 22. Results Database 22 (discussed in detail below) stores "developed" data and information. "Developed" data and information are created by the components of Integrated Disease Information System 10 as the components receive, analyze, and generate data and information. It should be noted, however, that intermediate, "developed" data could also be buffered or stored, in whole or in part, by Data/Information Source 20. The data and information developed by Integrated Disease Information System 10 and stored in Results Database 22 is that which the user requested the system to generate.

Integrated Disease Information System 10 may be implemented with a programming language like C++, or by using available graphical user interface and application design software packages. For example, Integrated Disease Information System 10 could be implemented using Microsoft Visual Basic® and Microsoft Access®. The principle interactive components of the software are the user interfaces, which display the results of Target Discovery Explorer 12, Clinical Trials Explorer 14, PE Explorer 16, and Disease Progression Explorer 17, as well as provide a window into Data/Information Source 20 and Results Database 22. These and other features are discussed in detail below.

Integrated Disease Information System 10 is shown for illustrative purposes only as comprising, in a unitary manner, Target Discovery Explorer 12, Clinical Trials Explorer 14, PE Explorer 16, and Disease Progression Explorer 17. It is also contemplated, however, that each of the components could stand alone, individually occupying the position now occupied by Integrated Disease Information System 10. That is, one Explorer does not necessarily require the others, but certain capabilities are provided by a system in which each of the components shown interacts and exchanges information with other components. For example, a system could include Data/Information Source 20 containing information typically generated by Target Discovery Explorer 12 as well as additional information as necessary and available. Such a system would support a stand alone Clinical Trials Explorer 14 which interacts with Input/Output 18, Data/Information Source 20, and Results Database 22.

Figure 32:
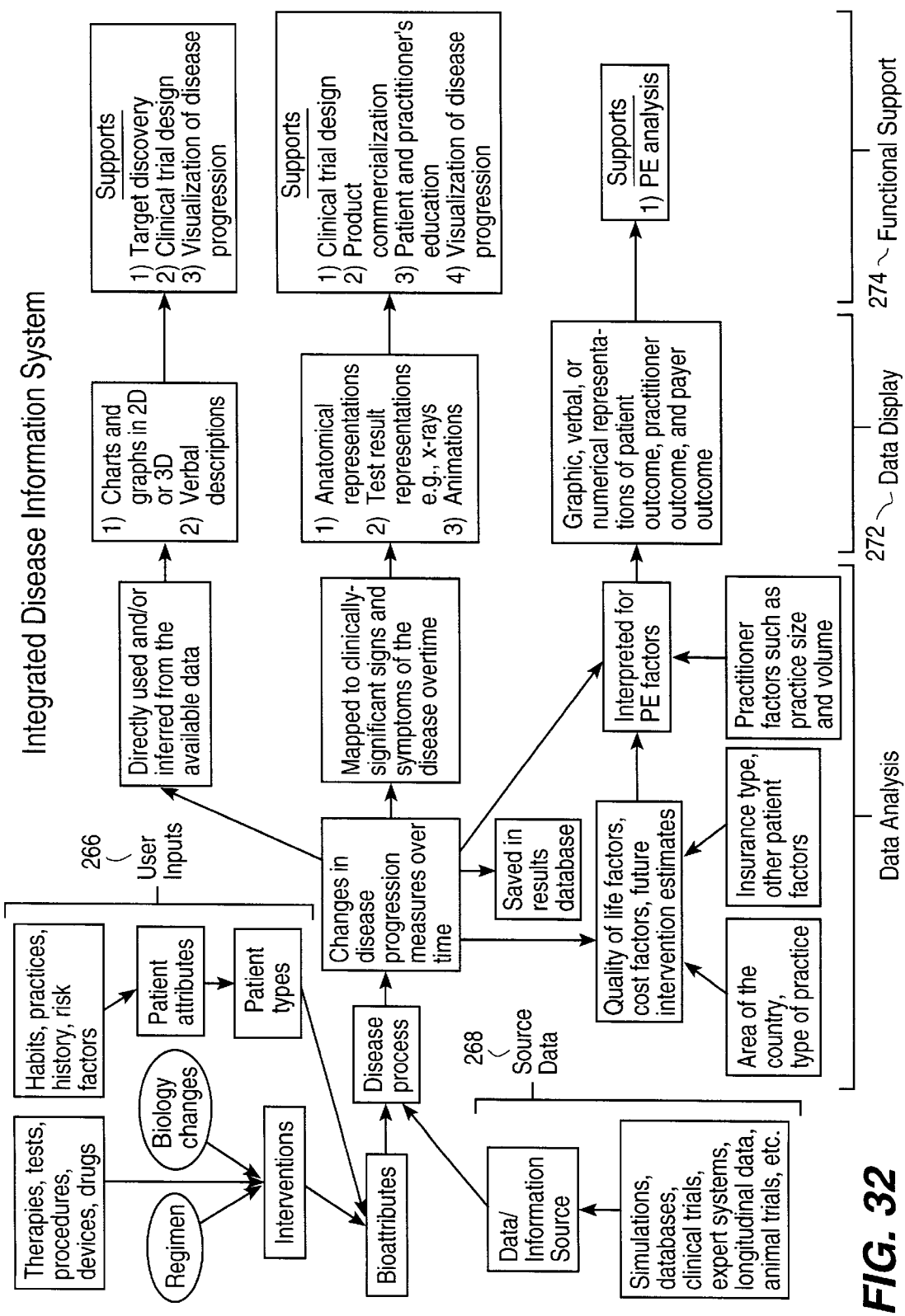
FIG. 32 depicts the functional layout of Integrated Disease Information System 10.

FIG. 32 depicts the functional layout of Integrated Disease Information System 10. Essentially, Integrated Disease Information System 10 receives input 266 from the user, queries 268 a data source in response to the user input, analyzes 270 the data retrieved from the data source, and displays 272 the data to the user in a variety of formats in order to support 274 the user's high level functional requirements. The user inputs biologic parameters of the biological process or system under consideration, patient attributes, and attributes of a proposed intervention that may alter disease progression in the patient, given the patient's attributes. Integrated Disease Information System 10 translates this information into an appropriate query of the source data stored in Data/Information Source 20, submits the query, and retrieves the results. The source data contains information about the disease process under study in one or more of a variety of electronic formats. The retrieved data depict disease progression over time on the relevant disease progression measures. Integrated Disease Information System 10 analyzes the retrieved data in a number of ways. The retrieved data may be manipulated to infer disease progression in the patient, mapped to clinically-significant signs and symptoms of the disease, and/or interpreted to estimate the pharmacoeconomic benefit of the proposed intervention. After Integrated Disease Information System 10 analyzes the data, it formats the data for presentation in a user-selected format. The available formats span a wide variety of options that are suited to supporting the user's functional needs. Different presentation formats support different functional requirements and the formats available are specific to each Explorer. Overall, Integrated Disease Information System 10 supports the four principle functions in intervention development: target discovery, clinical trial design, pharmacoeconomic analysis, and patient and practitioner education in support of product commercialization.

OVERVIEW OF OPERATION

Figure 3:
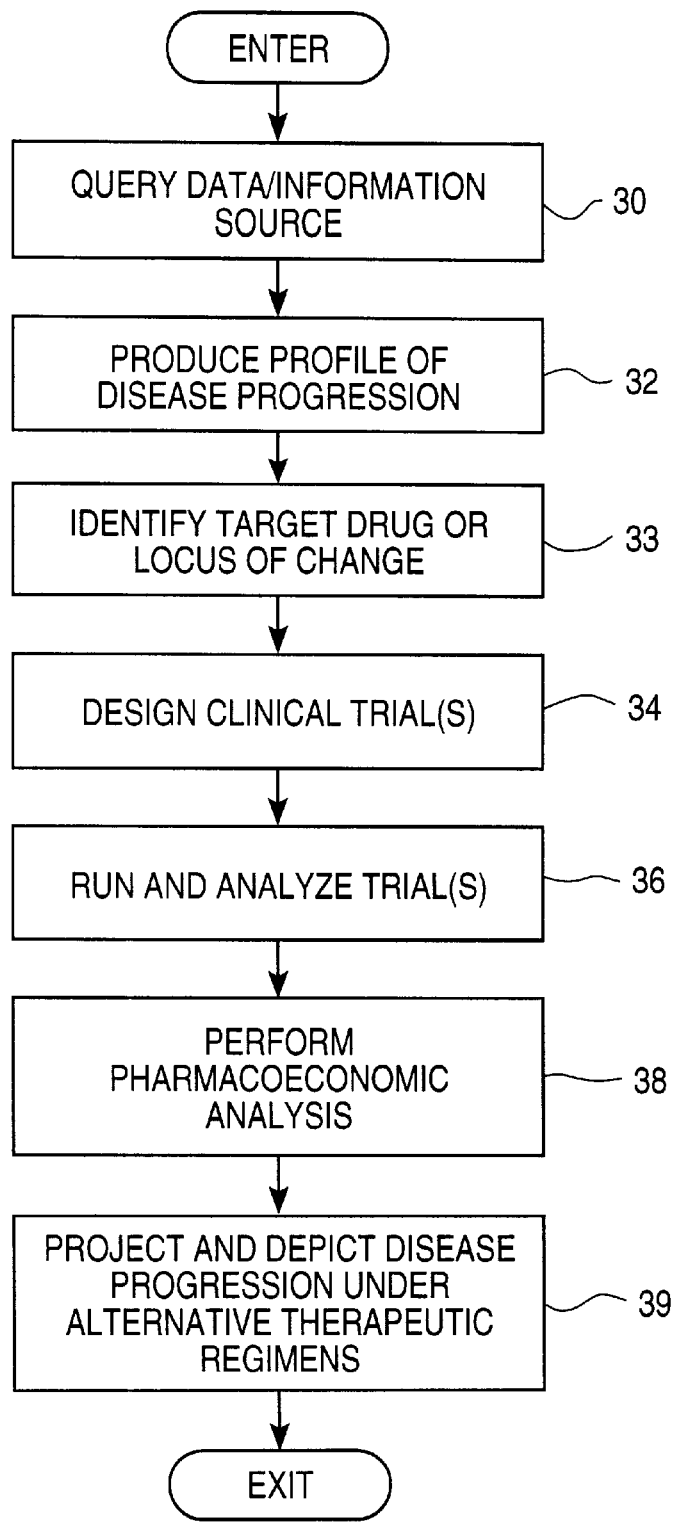
FIG. 3 is a flow chart showing the sequence of events that advantageously utilizes the disclosed Integrated Disease Information System.

FIG. 3 is a flow chart showing a scenario of events advantageously utilizing Integrated Disease Information System 10. Based on the user's input of various biological parameter values related to the disease process and patient type data, Integrated Disease Information System 10 queries 30 Data/Information Source 20 to produce 32 an estimate of disease progression. The estimate of disease progression is a model of the disease outcome over time within the supplied biological parameters. This model reflects the average course of disease progression in a given patient type (i.e., patients sharing common attributes) under the conditions specified by the user. Once the estimate of disease progression has been established, a user continues to interact with Integrated Disease Information System 10 to identify 33 target leverage points in the disease biology that alter the course of disease progression.

This first process of the Integrated Disease Information System 10, implemented by Target Discovery Explorer 12, provides a user with methods of altering biological parameters in the disease process to identify a proposed intervention. For example, if directed by the user to do so, Target Discovery Explorer 12 queries 30 Data/Information Source 20 and develops information showing dynamic changes in the progression of a disease if a certain cytokine (i.e., protein produced and released by cells that signals other cells) or set of cytokines is blocked. This assists a user in gathering information about combinations of biological changes that might yield a good disease prognosis. An alternative method for using Target Discovery Explorer 12 to identify an appropriate intervention is to start with the known effects of an intervention on human biology. The user then enters the known biological effects of various interventions into Target Discovery Explorer 12, which then queries 30 the data source to see which intervention provides an efficacious disease progression. Target Discovery Explorer 12 may alternatively assist a user in understanding markers of accelerated disease that would reliably screen patients for the disease. These approaches to using Target Discovery Explorer 12 help a user generate hypotheses about potential interventions for a given disease.

It should be kept in mind that the data and information in Data/Information Source 20 reflects the analyses being performed by the components of Integrated Disease Information System 10 (discussed in more detail below). For example, Data/Information Source 20 may include a simulation model of biological processes or other processes related to the analyses performed by the components of Integrated Disease Information System 10. Such a simulation model would receive particular model parameters from the user or system, and run several simulations to derive an estimate of disease progression based on different input parameters representing different patient types. Data/Information Source 20 may include any and all available sources of data to support the analyses performed by the different Explorers.

Once an intervention has been identified 33 by the user with the assistance of Target Discovery Explorer 12, Integrated Disease Information System 10 helps the user design 34 an appropriate clinical trial or trials via Clinical Trials Explorer 14. Clinical Trials Explorer 14 uses the locus of change information (i.e., the biological changes that yield efficacious disease progression) and/or intervention information to simulate clinical trials to search for patient attributes that might impact the intervention effect, either weakening or strengthening it. For example, a user might hypothesize that an intervention, while effective in the general population, will have limited effect on types of patients, such as those with diabetes mellitus. Clinical Trials Explorer 14 receives user input regarding a proposed intervention and particular patient types, and uses the input to simulate 36 and test a variety of patient types by querying Data/Information Source 20 to evaluate the disease progression for patients receiving the experimental intervention compared to patients receiving a placebo, or an alternative intervention, for each relevant patient type. Clinical Trials Explorer 14 provides the user with information about ranges of possible intervention effects, including patient types for which the intervention might have no effect or result in a poor effect, i.e., more rapid disease progression.

Clinical Trials Explorer 14 then sends the results of the clinical trial simulation(s) to Results Database 22 or directly to PE Explorer 16 for the next step, pharmacoeconomic analysis. Pharmacoeconomic analysis 38 compares a proposed intervention to current standard practice(s) for each patient type. Based on expert rules collected and implemented as part of PE Explorer 16 during development of Integrated Disease Information System 10, pharmacoeconomic analysis evaluates the outcome for a particular type of patient, with a particular version of the proposed intervention, in terms of cost and quality of life, and yields an evaluation of overall patient satisfaction. Pharmacoeconomic analysis also evaluates outcomes for the medical practitioner (i.e., the provider) and the insurance carrier (i.e., the payer), using rules supplied by human experts in the disease domain under investigation and implemented in PE Explorer 16 code.

Disease Progression Explorer 17 receives the data and information developed by Target Discovery Explorer 12, Clinical Trials Explorer 14, PE Explorer 16, and/or other data sources either directly or via Results Database 22, or perhaps Data/Information Source 20, to produce an estimate of disease progression. A medical practitioner can input information about the patient attributes, such as patient history, risk factors, and intervention options, and Disease Progression Explorer 17 graphically projects 40 the course of the disease for the patient under various scenarios. A textual explanation of the basis and meaning for the projection is provided to clarify the results for the practitioner and patient and to support practitioner and patient education.

In summary, the preferred embodiment of the Integrated Disease Information System, in accordance with the present invention, includes four distinct components: Target Discovery Explorer 12, Clinical Trials Explorer 14, PE Explorer 16, and Disease Progression Explorer 17. Input/Output 18 receives input from a user, Data/Information Source 20, Results Database 22, and each Explorer; and displays results to the user in the form of graphical and textual information. Data supplied by Data/Information Source 20 and Results Database 22 is also analyzed by the four components of Integrated Disease Information System 10. Target Discovery Explorer 12 helps the user identify a potential intervention. Clinical Trials Explorer 14 supports analysis of the results of the proposed intervention across patient types. PE Explorer 16 compares the benefits of the proposed intervention to current standard practice. Finally, Disease Progression Explorer 17 projects the course of the disease across time in an effort to educate the patient and practitioner to the relative merit of alternative intervention regimens. The results of these analyses are stored in Results Database 22. The following sections discuss these components of the invention in detail.

EXPLORER ARCHITECTURE

Figure 4:
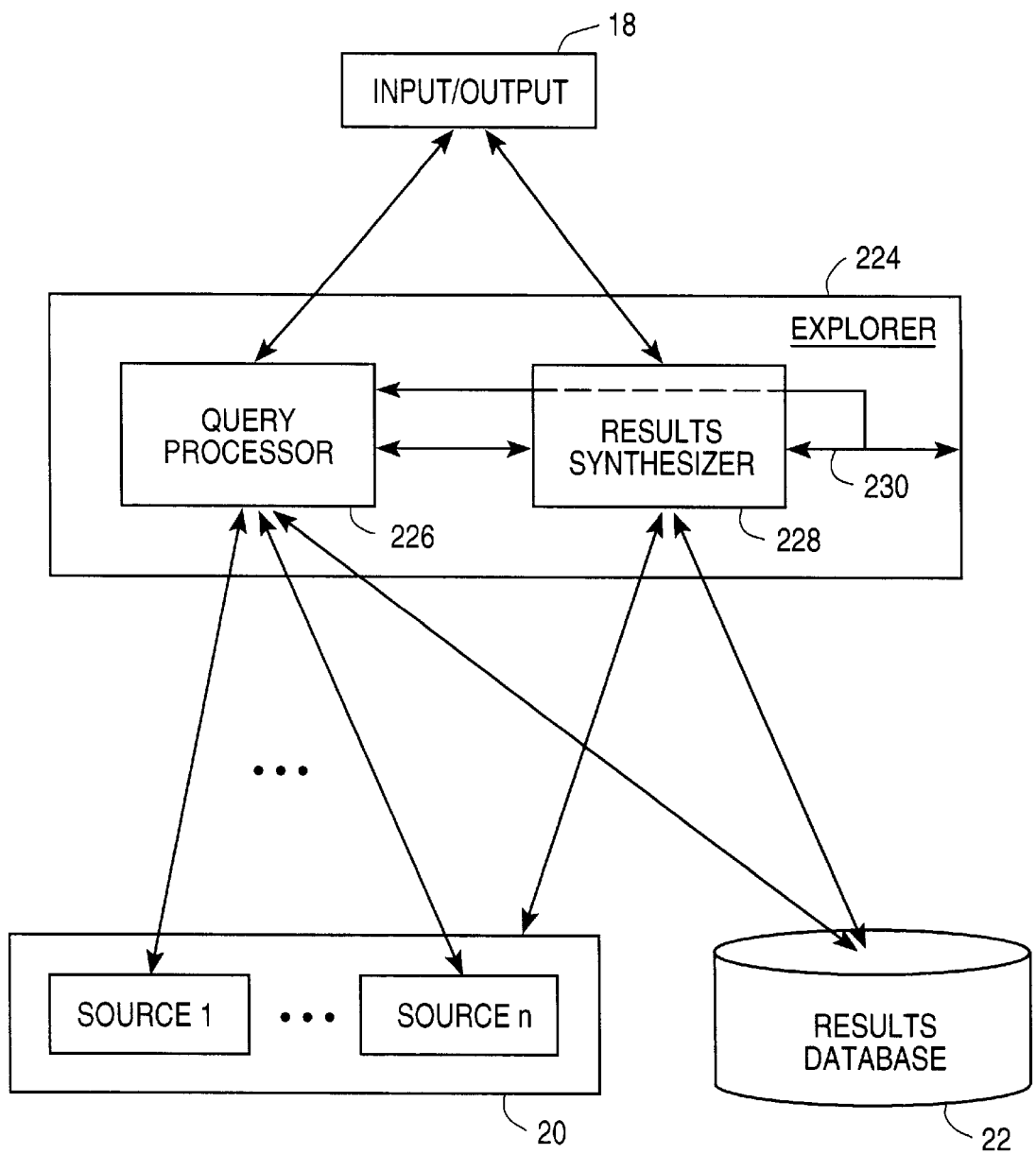
FIG. 4 is a block diagram showing a typical Explorer architecture.

FIG. 4 is a block diagram showing the architecture of a typical explorer. Each Explorer 224 is primarily comprised of Query Processor 226 and Results Synthesizer 228. Each of Query Processor 226 and Results Synthesizer 228 may communicate with other Explorers via Communication Path 230. Alternatively, each of Query Processor 226 and Results Synthesizer 228 may communicate with other Explorers by selectively buffering data and/or information in Data/Information Source 20 or Results Database 22.

Query Processor 226 interacts with a user to receive a variety of data and/or information related to an Explorer. Query Processor 226 receives user input and translates it into one or more queries of Data/Information Source 20 and/or Results Database 22. The number and nature of the queries depends on the sources of data/information in Data/Information Source 20. For example, if Source 1 is a relational database, a relational query would be formed. If Source n is a simulation model, the model would be run with the input from the user required to set up the parameter values for the simulation. If the data/information from the user is not in the proper form for directly formulating a query for Data/Information Source 20, Query Processor 226 infers a query to match as closely as possible the format and content of the Source being queried. The details of how this is accomplished depend on the implementation and the characteristics of the data source. In general, in order to do this, the software code for Query Processor 226 contains algorithms for translating the user's input into a query language appropriate for the data source. A query is generated dynamically by the code and the query is submitted to the data/information source. Queries may also include or use data and information from another Explorer, receiving data/information via 230, and/or retrieving data/information from Results Database 22.

In order to perform its functions, Query Processor 226 includes four software components: user interface, query generation, query submission, and results collection. User input is accomplished through the user interface. The interface is designed and constructed such that all necessary information for a query is collected from the user. The query generation component dynamically constructs a query from the collected information in the form required by the data source. Methods of constructing queries dynamically for a variety of types of data sources are well known in the art. The query submission component sends the query to the appropriate data source and directs the data source to conduct the relevant search. Finally, results collection component receives and stores the results of the query returned by the data source.

Once Query Processor 226 receives the requested data and/or information from Data/Information Source 20, the data and/or information are sent to Results Synthesizer 228 for further processing. Results Synthesizer 228 is responsible for synthesizing the results from the data source(s) into a presentation to the user in the format requested by the user from the options available in the particular Results Synthesizer 228. Results Synthesizer 228 has two software components: a data analysis component and a presentation component. The data analysis component manipulates the data in a manner specific to each Explorer and these analyses are described in the following sections. The presentation component is again specific to the Explorer and includes one or more methods of displaying the data to the user in a format that supports the user's decision making process.

DISEASE EXAMPLE

An example from osteoporosis illustrates one possible use of the system disclosed herein. Osteoporosis is a life long disease process but most often becomes clinically evident in post-menopausal women. The cause of osteoporosis can be traced to changes in the bone remodeling process that result from decreased estrogen, decreased mechanical loading on the bone, and a variety of other factors that combine to reduce the density of the bone and increase the likelihood of bone fractures. Treatments of the condition include estrogen replacement or bisphosphonate therapy.

Bone is a living structure that undergoes constant remodeling throughout the life of an individual. The principle cells involved in bone remodeling are osteoblasts, that build bone, and osteoclasts, that break it down. The action of these two cells is tightly coupled in a normal individual to maintain healthy bone, including optimal remodeling rates and bone mineral density levels. Any uncoupling of the action of these two cell types can cause suboptimal bone mineral density and weaken the bone, making fracture more likely.

Estrogen is related to osteoclast activity, such that decreases in estrogen increase bone breakdown rates, leading to weakened bone. Estrogen supplements reestablish more optimal bone remodeling patterns and can be started at menopause to prevent osteoporosis. However, estrogen supplements have decided drawbacks, including increased risk of breast and uterine cancer. These insights have emerged through years of studying estrogen supplements. Alternatively, bisphosphonate therapy can be used for patients who have contraindications for estrogen replacement therapy, e.g., a family history of breast cancer. However, bisphosphonate therapy is only prescribed once the disease is clinically evident. Clearly, a therapy that has fewer potential side effects and can be used to prevent the disease would be desirable.

Integrated Disease Information System 10 could help a user discover and validate an intervention for osteoporosis in a systematic fashion. Target Discovery Explorer 12 enables the user to identify a locus in the biology of bone remodeling or more generally in the osteoporosis process that would retard bone density loss. Once the target is identified, Clinical Trial Explorer 14 enables the user to test a proposed intervention that affects that target in different patient types to identify those patients for whom the proposed intervention would be most effective. PE Explorer 16 enables the user to compare the effectiveness of the proposed intervention against estrogen replacement and bisphosphonate therapy for patients, practitioners, and payers. Finally, Disease Progression Explorer 17 assists in describing the clinical benefit of the new intervention (e.g., reduced fracture risk) to patients and practitioners in order to facilitate commercialization of the new intervention.

This osteoporosis disease example will be discussed in further detail to elucidate the functions of each Explorer in the following sections.

DATA MODEL

Each of the Explorers supports the user's decision making process at a particular stage of the target development process. The data developed by one Explorer to support the user's decision making can then be used by another Explorer. Table 1 lists the type of decision support and developed data provided by each Explorer.

TABLE 1

Explorer Data Relationships

| Explorer | Decision Support | Developed Data |
|---|---|---|
| Target Discovery | Supports finding a biological target for a potential intervention that influences the disease in a positive manner. | Produces data relating any proposed intervention to measures of disease progression that show the effect of the intervention. |
| Clinical Trials | Supports the design of a clinical trial for the experimental target. | Produces data relating the response of patient types to the proposed intervention showing which have good outcomes and which have no change or poor disease progression. |
| Pharmacoeconomic | Supports an understanding of the merit of the proposed intervention in relation to existing practices. | Produces data pertaining to patient satisfaction, practitioner satisfaction, and relative cost information for payer evaluation. |
| Disease Progression | Supports patient and practitioner visualization and understanding of the clinical impact of using a new intervention on the disease progression over time. | Produces data relating patient risk factors for the disease to clinically relevant signs and symptoms. |

The Explorers work together to provide an integrated approach to the target development process. Target Discovery Explorer 12 helps the user discover which changes in a biological process (e.g., the strength of the immune response, the rate of bone remodeling, the strength of the signals between cells) most affect the progression of the disease or are good markers of disease. This directs the user to potential agents, such as drugs, other therapeutic procedures, or testing procedures, that could serve to reduce or measure disease progression. Clinical Trials Explorer 14 then helps the user discover which patient types will respond best to the proposed intervention. Pharmacoeconomic Explorer 16 helps the user decide whether the economics of using the proposed intervention exceeds the use of existing products. Disease Progression Explorer 17 depicts the relationship of the proposed intervention to the clinical manifestation of the disease progression in an effort to improve patient and practitioner education in support of product commercialization.

The organization of the data used by the Explorers may be in a variety of forms, such as relational databases, expert systems, simulation models, clinical trials, and/or expert opinion. Integrated Disease Information System 10 can be implemented to interface to a wide variety of electronic formats containing information with the appropriate characteristics, and all of the data/information does not need to be in a single data source. Each of the Explorers requires similar types of data, however the data needed for each is at a different level of granularity. The source of the data for any given Explorer may be outside the Integrated Disease Information System or it could be developed by one or more of the other Explorers. Table 2 describes the type of data used by each Explorer.

TABLE 2

Explorer Data Types

| Explorer | Data Type |
|---|---|
| Target Discovery | Data that links changes in biology, e.g., changes in cytokine output by a cell type or changes in patient attributes, to changes in disease progression, as measured by selected disease progression measures. These data are at a very low level of granularity, describing how the cell types involved in the disease process function, what they produce, and how they affect the disease progression at the cellular on up to the clinical level. |
| Clinical Trials | Data that links patient attributes, intervention effects, and disease progression, including data that describes how a proposed intervention affects the course of the disease. These data are also at a low level of granularity, describing how interventions affect the disease at the cellular level and how that ultimately affects the disease progression over time. |
| Pharmacoeconomic | Data that describes a disease progression for a particular type of patient on different types of interventions: the standard practice for that patient and the proposed intervention; and data about the cost of therapy, how cost is influenced by insurance coverage, and practitioner needs and preferences for therapy/test prescriptions. These data are at a high level of granularity, describing how different patient types respond to different interventions at the level of disease signs and symptoms and the resulting quality of life |
| Disease Progression | Data that links patient attributes, intervention effects, and disease progression to clinically relevant outcomes of the disease, for example changes in fracture rates in osteoporosis. These data are at several levels of granularity and must be sufficient to educate both patients and practitioners about the disease process and the key attributes that will influence it for the given patient. |

If the data for any given Explorer is not available, the first task in development is to collect or generate it. For example, in order to obtain the needed data that links changes in biology to changes in disease progression, a survey of the open literature may be conducted, data from a laboratory research program may be obtained, and/or a set of experts may provide their knowledge about the basic disease biology. Finally, a simulation model may be built from the basic biology knowledge and then used to generate the necessary data.

Target Discovery Explorer 12 uses data that links changes in the biology of a disease to the disease progression. Continuing the osteoporosis example, this knowledge would be available from disparate sources and might be of the following raw form:

TABLE 3

Example of Raw Data for Target Discovery Explorer

| Research Report #1: | Blocking IL-1 and TNFα by 10% reduces bone density loss in mice by 40% |

TABLE 3-continued

Example of Raw Data for Target Discovery Explorer

| | |
|---|---|
| Research Report #2: | Blocking TNFα alone does not reduce bone density loss in mice |
| Research Report #3: | IL-6 knockout mice show no bone density changes after ovariectomy |
| Research Report #4: | IL-6 receptor antagonists reduce osteoclast activity in vitro |
| Expert Opinion #1: | Blocking TNFα and moderately augmenting the growth factors will reduce bone density loss by 25% |
| Simulation Result: | Blocking mast cell degranulation reduces IL-4 thereby reducing bone loss by 10% |

Data such as these are made available to the Target Discovery Explorer 12 in an electronic format. These data are made available in an underlying data format that has the following informational characteristics:
1) a set of attributes, including:
   a) patient attributes, e.g., smoking/nonsmoking; pre vs. post menopausal
   b) biology attributes, e.g., level of mast cell production of IL-4; number of osteoblast precursors
   c) intervention attributes, e.g., nonsteroidal anti-inflammatory drug effects on $PGE_2$ production by monocytes; intervention delivery schedule
   coupled with
2) a set of disease progression measures provided at specified points in time over a specified duration of analysis
   b) changes in cellular behavior, e.g., changes in the rate of mast cell degranulation
   c) changes in intermediate disease progression measures, e.g., changes in bone mineral density or parathyroid gland functioning
   d) changes in clinically observable disease progression measures, e.g., risk of fracture over the lifecycle.

Measures of disease progression span a variety of levels of granularity in relation to the disease biology. Some changes associated with disease progression are measured at the cellular level or sub-cellular level and derive from changes in the behavior of individual cells and groups of cells of the same type. Disease progression is also measured by changes in the aggregate behavior of multiple cell types within the local environment specific to the disease, e.g., in the bone. Up another level, disease progression is measured by systemic changes in organ systems and throughout the human body. For example, in osteoporosis, systemic changes occur in bone mineral density and, under certain circumstances, in the circulating level of parathyroid hormone produced by the parathyroid gland. This level generally maps to the presenting signs and symptoms of the disease from a practitioner's perspective. Finally, disease progression is measured in clinically observable or clinically-relevant ways that directly affect and alert the patient, such as the bone fractures, humped back, and reductions in the patient's height that occur in osteoporosis.

Proposed interventions can affect one or more of these levels of disease progression measures, ideally affecting them all. For example, estrogen supplements affect the behavior of osteocytes, primarily, and osteoblasts, secondarily. This modulates the bone remodeling rate and the breakdown in bone, reducing bone mineral density loss and ultimately preventing fractures. Alternatively, fluoride therapy for osteoporosis has advantageous effects on bone mineral density but, particularly once the disease is underway, does not have corresponding effects on fracture risk.

Clinical Trials Explorer 14 uses data that links patient attributes, intervention attributes, and disease progression. Again, the data may be available in the open literature, from a laboratory research program, from a clinical trial of a new intervention, from an expert system, or from a simulation model of the disease. The data format is very similar to that used by Target Discovery Explorer 12, however it includes an additional temporal element tied to the biology or intervention variations that allows explicit definition of timing and duration of these variations. Intervention regimens may have an effect for the period of use but no long term effect. In fact, there may be a rebound effect after intervention withdrawal. Thus, the biological attributes are also evaluated across a temporal dimension, and the attribute variations, therefore, include time information so that the effect of changing the attribute for some defined duration may be assessed.

Data coupling attribute variations and disease progression measures across a defined period of time are thus used by Clinical Trials Explorer 14. For example, suppose a therapy suppresses mast cell IL-4 production but would only be prescribed for a period of one year following menopause. The resulting disease progression measures would then illustrate the effects of altering this attribute, mast cell IL-4 production, at the appropriate time for the appropriate duration on the disease progression before, during, and for several years after this short-term therapy versus other potential durations of treatment. The most natural sources for these data are a simulation model, a long term program of research, or a longitudinal clinical trial so that consistent data over specified time frames are available.

Pharmacoeconomic Explorer 16 uses data that describe disease progression for a variety of patients using various, different interventions, including the proposed intervention. These data may be based on a clinical trial, practice records, insurance records, expert knowledge, or a simulation model. The data used by Pharmacoeconomic Explorer 16 are at a higher level of granularity: patient and intervention attributes coupled with disease progression measures at the intermediate and clinical level. These data are available either from an independent data source or from the synthesis performed by the Clinical Trials Explorer 14. The Pharmacoeconomic Explorer 16 does not require data about the underlying biology of the disease; it just uses the level of clinical disease progression after a pre-specified number of years. It also uses information about the relative costs of interventions, the coverage of different insurance programs for various interventions, the preferences of practitioners for methods and procedures, the standard intervention(s) for a given patient type, and how a patient moves between categories of disease states as their disease progresses or regresses.

Finally, Disease Progression Explorer 17 potentially uses any of the data used by the other Explorers. Disease Progression Explorer 17 is an education tool for patients and practitioners to support product commercialization. As such, it uses data about intervention effects across time, such as that used and synthesized by Clinical Trials Explorer 14, to support both patient and practitioner understanding of intervention effects on disease progression over time. It also uses data about the underlying biological effects of interventions, such as that used and synthesized by Target Discovery Explorer 12, to support practitioner, and possibly patient, education. And it uses information about the relative costs and merits of various intervention regimens, such as that used by Pharmacoeconomic Explorer 16, to support patient education and decision making.

DATA/INFORMATION SOURCE

Figure 31:
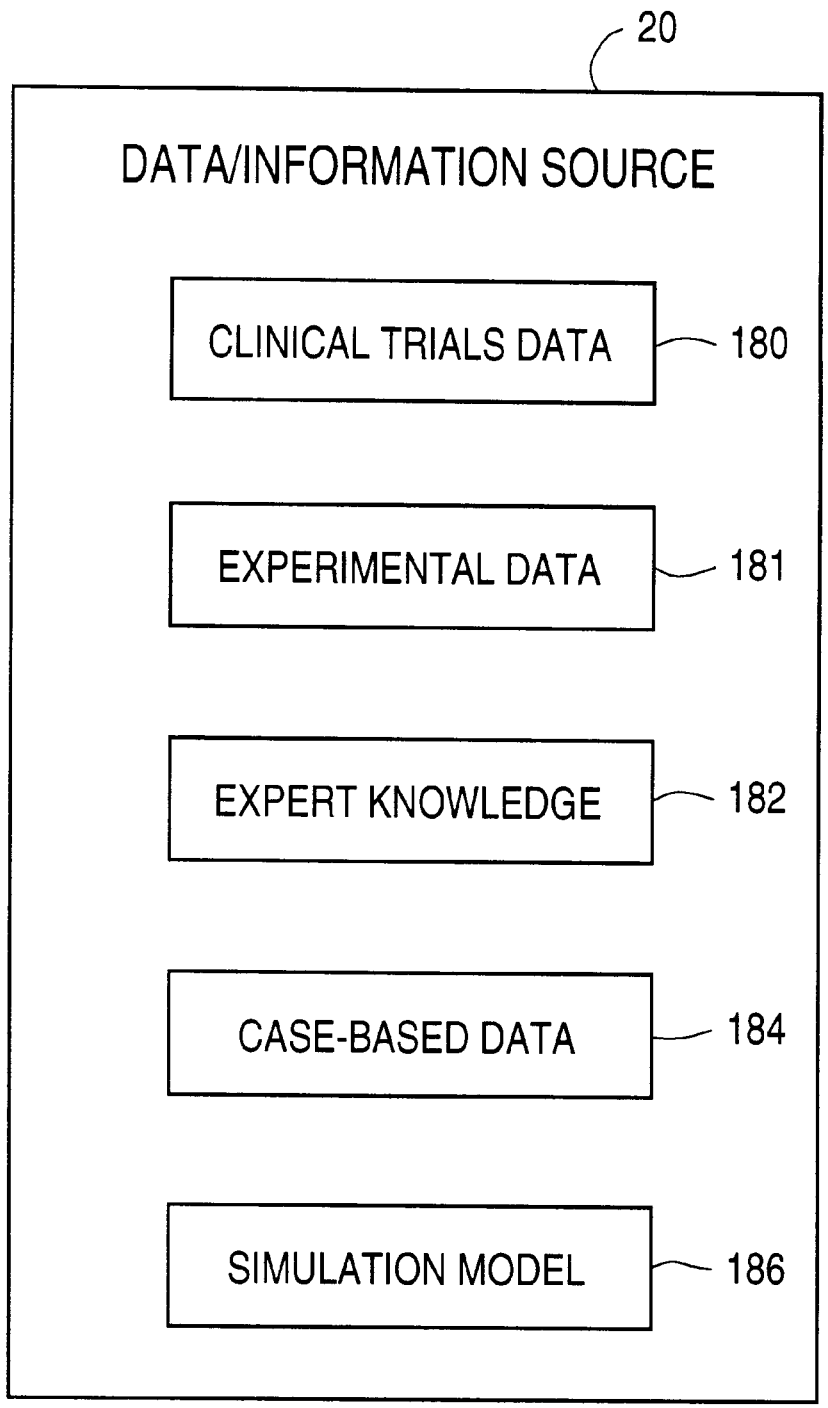
FIG. 31 is a block diagram showing possible components of the Data/Information Source.

FIG. 31 is a block diagram showing possible components of Data/Information Source 20. Data/Information Source 20 is accessible via the user-friendly graphical user interfaces provided by the Explorers, as discussed below, for data entry, querying, and reporting. The particular method of querying the Data/Information Source 20 used by the Explorers depends on the format of the data or information. For example, where Data/Information Source 20 includes an SQL database, submitting a query to the SQL database involves constructing the query using correct SQL syntax. In this embodiment, the software includes a representation of the structure of the database, i.e., the tables and relationships between the tables, that allows the code to generate the appropriate queries to retrieve information from the database. Where Data/Information Source 20 includes an expert system implemented in a rule-based tool, such as CLIPS or PROLOG, an Explorer launches the expert system tool and exchanges information with it either dynamically or through a data structure, such as a file or database. Where Data/Information Source 20 includes a simulation model, the system 10 launches the simulation code of the model and sends the simulation model the appropriate information.

Information flow in Integrated Disease Information System 10 occurs dynamically through a facility like Dynamic Data Exchange, Dynamic Link Libraries or Visual Basic Controls under Microsoft Windows™, or through shared files or a shared database such as the Results Database 22.

Integrated Disease Information System 10 organizes data/information provided to and received from objects that appear on the screen so that the other components of the system using the information can interpret the data/information correctly The structures used to ensure this vary widely depending on the particular implementation. Factors that may affect this include the sources of available data and the software language/tool used for implementation. For example, data/information may be temporarily stored in arrays, lists, streams, or custom structures defined in the implementation.

As shown in FIG. 31, Data/Information Source 20 may include, but is not limited to, Clinical Trials Data 180, Experimental Data 181, Expert Knowledge 182, Case-Based Data 184, and/or a Simulation Model(s) 186. Each of these may be used by one or more of the Explorers shown in FIG. 2 and described above. It should also be kept in mind that Target Discovery Explorer 12, Clinical Trials Explorer 14, PE Explorer 16, and Disease Progression Explorer 17 may exchange information directly with each other depending on the implementation.

Examples of sources for Data/Information Source 20 include, but are not limited to, expert knowledge bases, historical databases, clinical trials, and/or computer models. A single Data/Information Source 20 may include multiple types of information therein. Integrated Disease Information System 10 is connected to Data/Information Source 20, which stores data collected independently of Integrated Disease Information System 10. The following list describes each type of source data:

1) Clinical Trials Data 180 may include, for example, disease progression for all patients in a clinical trial, including the patient attributes, and reflects the formal methodology used in that trial.
2) Laboratory results include data collected in a research program on the target disease.
3) Experimental Data 181 may include, for example, results obtained by using animal models to study the biological system, or other similar types of studies.
4) Expert Knowledge 182 may be, for example, in the form of an expert system or knowledge base.
5) Case-Based Data 184 may include, for example, historical information about individual instances collected in a relatively informal manner over time, perhaps years. This data is most likely collected about patients in private practices. On the other hand, it may be formally collected in long-term longitudinal studies.
6) Finally, a Simulation Model 186 of the disease process may supply the data based on a simulation of the disease over time. The level of detail in the disease simulation model varies depending on the needs of the implementation.

RESULTS DATABASE

The components of Integrated Disease Information System 10 are also connected to Results Database 22. This database stores the final analyses of Target Discovery Explorer 12, Clinical Trials Explorer 14, PE Explorer 16, and Disease Progression Explorer 17 for subsequent viewing and further manipulation by the system or the user. It should be kept in mind that some of the information generated by the components of Integrated Disease Information System 10, including the final analyses, may also be directly transferred to other components, e.g., Input/Output 18, Data/Information Source 20, and/or other Explorers.

The format of Results Database 22 stores the synthesized data from all of the Explorers and supplies data that can be used by each of the Explorers in their analyses. Therefore, a record in the database is of the following conceptual form:

a) patient attributes, e.g., the patient history and patient risk factors for the disease;
b) intervention attributes, including the standard and proposed intervention regimens;
c) disease progression for both regimens at specified points in time (e.g., monthly, yearly, etc.); disease progression includes data from subcellular level changes up through disease signs and symptoms;
d) costs of the standard and proposed interventions for the patient and payer;
e) outcomes for the pharmacoeconomic analysis of the patient, practitioner, and payer, including estimated future therapy requirements, quality of life analyses, and practice-based analyses for the standard and proposed interventions;
f) disease progression measures and mappings to the clinically-based graphical anatomical representations.

Results Database 22 is the repository of all data synthesized by the Explorers and is accessible to each Explorer to support the analysis process. Once data has been synthesized and evaluated by an Explorer and stored in Results Database 22, it is available to the user at any future point. Based on a request from the user to any Explorer, the Explorer accesses Results Database 22, retrieves the results of the stored analysis, and simply presents the results to the user in the presentation format appropriate to that Explorer. In this way, the Explorers do not need to recompute various estimates over and over again, and the results are available to the other Explorers.

TARGET DISCOVERY EXPLORER

The first step in the scientific process is hypothesis formation. It is generally considered the hardest, least rigorous, and least reliable part of science because it is essentially the formulation of an insight that leads to a hypothesis that is then validated or refuted experimentally. Hypothesis formation requires exploration, analysis, and synthesis of very large, complex, highly multivariate and multidimensional data. Target discovery is hypothesis formation; it asks the question, "what changes in the biology of a disease will reduce the severity of the disease," or, in the case of a medical test, "what biological marker is a valid and reliable indicator of disease progression."

Target discovery is the process of finding a target locus in the biology of a disease process that is causally related to disease severity or that serves as a marker of the disease or of disease progression. In order to discover a proposed intervention that affects or measures the disease, a researcher normally evaluates numerous hypotheses about the underlying biology of a disease to find a target that affects or is indicative of disease progression. Even in large, well established research laboratories, the process may be rather haphazard, relying on the researchers' intuition, hunches, and best guesses. The more data available, the better the guesses may be, but the process is still typically ad hoc, enormously difficult, time consuming, and subject to error. In addition, the data available to support target discovery are likely to be extremely multivariate in nature, conflicting, uncertain, partial, and difficult to interpret. Furthermore, the data pertain to a complex process that proceeds over time with large amounts of self-regulating feedback.

The process of target discovery involves the classic scientific method of hypothesis formation, operationalization and testing, and theory refinement. Target discovery is principally hypothesis formation and, as such, has a number of defining characteristics. First and foremost, hypothesis formation requires data. Scientific advances are based on years of research and voluminous amounts of data. A second characteristic of hypothesis formation is mental imagery. Researchers often rely on mental images of a phenomenon in order to formulate a hypothesis. Target Discovery Explorer 12 supports hypothesis formation in the biological domain by providing a tool that supports systematic generation and exploration of a large body of data to identify targets and potential interventions, and a tool that supports visualization of that data and the relationships between various disease progression measures and biologic parameters, and other types of data.

Figure 5:
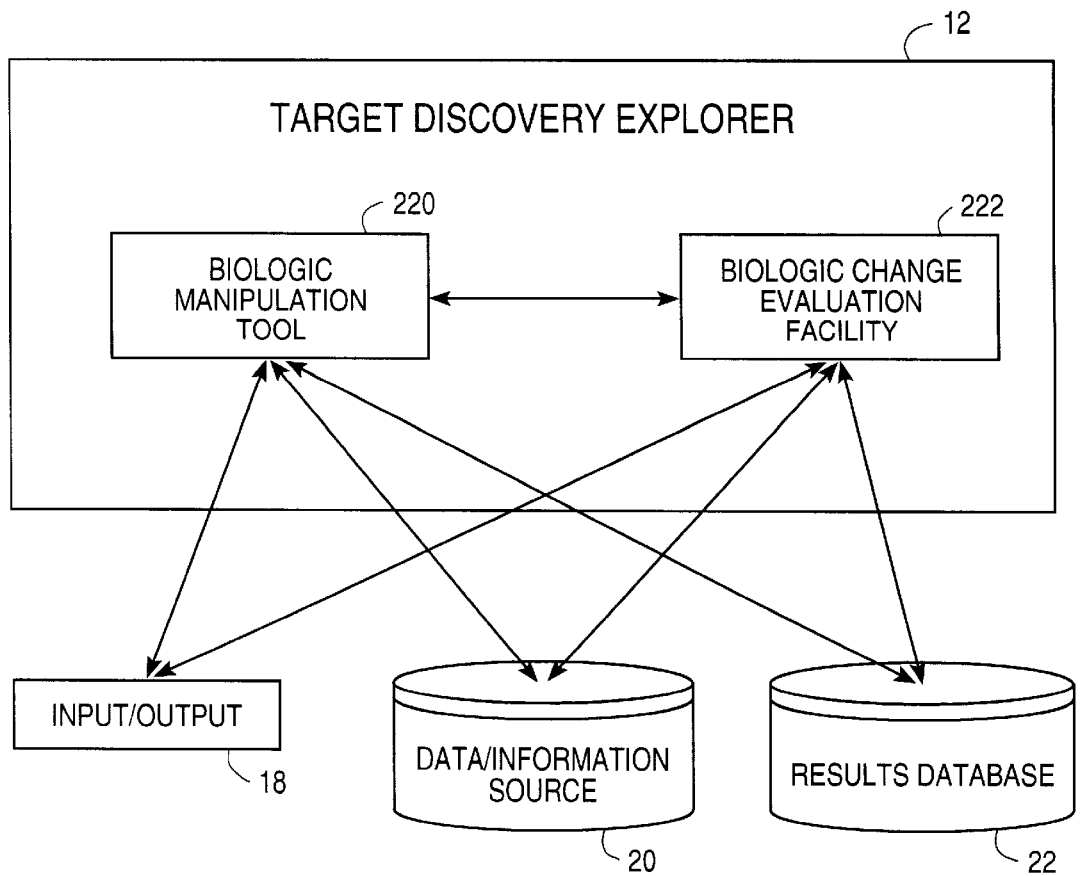
FIG. 5 shows a block diagram of the Target Discovery Explorer.

In addition, Target Discovery Explorer 12 imposes a methodology on the hypothesis formation process. Experimentation as an overarching paradigm for testing hypotheses is an approach familiar to all researchers. Thus, Target Discovery Explorer 12 uses an experimental approach to help a researcher identify possible biological targets for intervention. FIG. 5 shows a block diagram of Target Discovery Explorer 12. Target Discovery Explorer 12 characterizes the target discovery process as one that consists of information gathering and analysis. Information gathering is performed by the Biologic Manipulation Tool 220 and analysis is performed by the Biologic Change Evaluation Facility 222. Furthermore, information gathering is conceptualized as an experimental process, in which the researcher can design factorial studies in order to systematically collect a large set of data containing information about the underlying biology of a disease.

Target Discovery Explorer 12 includes two components: Biologic Manipulation Tool 220 and Biologic Change Evaluation Facility 222. As shown in FIG. 5, Biologic Manipulation Tool 220 and Biologic Change Evaluation Facility 222 communicate with Input/Output 18, Data/Information Source 20, and Results Database 22. Biologic Manipulation Tool 220 allows a user to qualitatively and quantitatively change parameters of biological systems to determine the impact of such changes on selected disease progression measures. For example, biologic data that may be modified include the level of insulin-like growth factor (IGF), IL-1, and IL-4. Correspondingly, disease progression measures for osteoporosis include the bone remodeling rate, the overall bone mineral density, the number of mast cells in the region, or the amount of parathyroid hormone output by the endocrine system. Biologic Change Evaluation Facility 222 supports visualization of the resulting data to help the researcher identify good intervention options. Biologic Manipulation Tool 220 is an instance of Query Processor 226, and Biologic Change Evaluation Facility 222 is an instance of Results Synthesizer 228. They are designed to support the collection, exploration, analysis, and synthesis of the highly complex, multidimensional biological data needed to support target discovery.

Biologic Manipulation Tool

With the Biologic Manipulation Tool 220, a user can change parameters defining the way cells in the biology respond, for example, by altering or eliminating the production of various cytokines. Alternatively, the user can change a biologic process by reducing the value of parameters defining the chemical signals that drive the process. The changes input by the user are generally selected in one of two different ways. In the first way, users input changes to the biology that they think may reduce disease progression. In this way, they find which biologic parameters are most influential in disease progression. From this information, they then may propose potential interventions. Alternatively, users may input biologic changes that are associated with the known biologic effects of existing interventions. In this way, they determine which known interventions provide positive alterations in disease progression.

Once the user has input the parameter changes into Biologic Manipulation Tool 220, the tool queries Data/Information Source 20 and retrieves or interpolates disease progression measures based on the user input. These disease progression measures describe how the input changes in the biology affect the disease progression. Results Database 22 maintains the results of these analyses for use by the Biologic Change Evaluation Facility 222. Biologic Change Evaluation Facility 222 assists the user in assessing the effects of the biologic manipulations on the progression of the disease. It displays the results of the queries in a variety of formats depending on the user's needs. The results can be displayed at a variety of levels from low-level basic biology to actual clinical symptoms, depending on the available data and the needs of the user.

Figure 6:
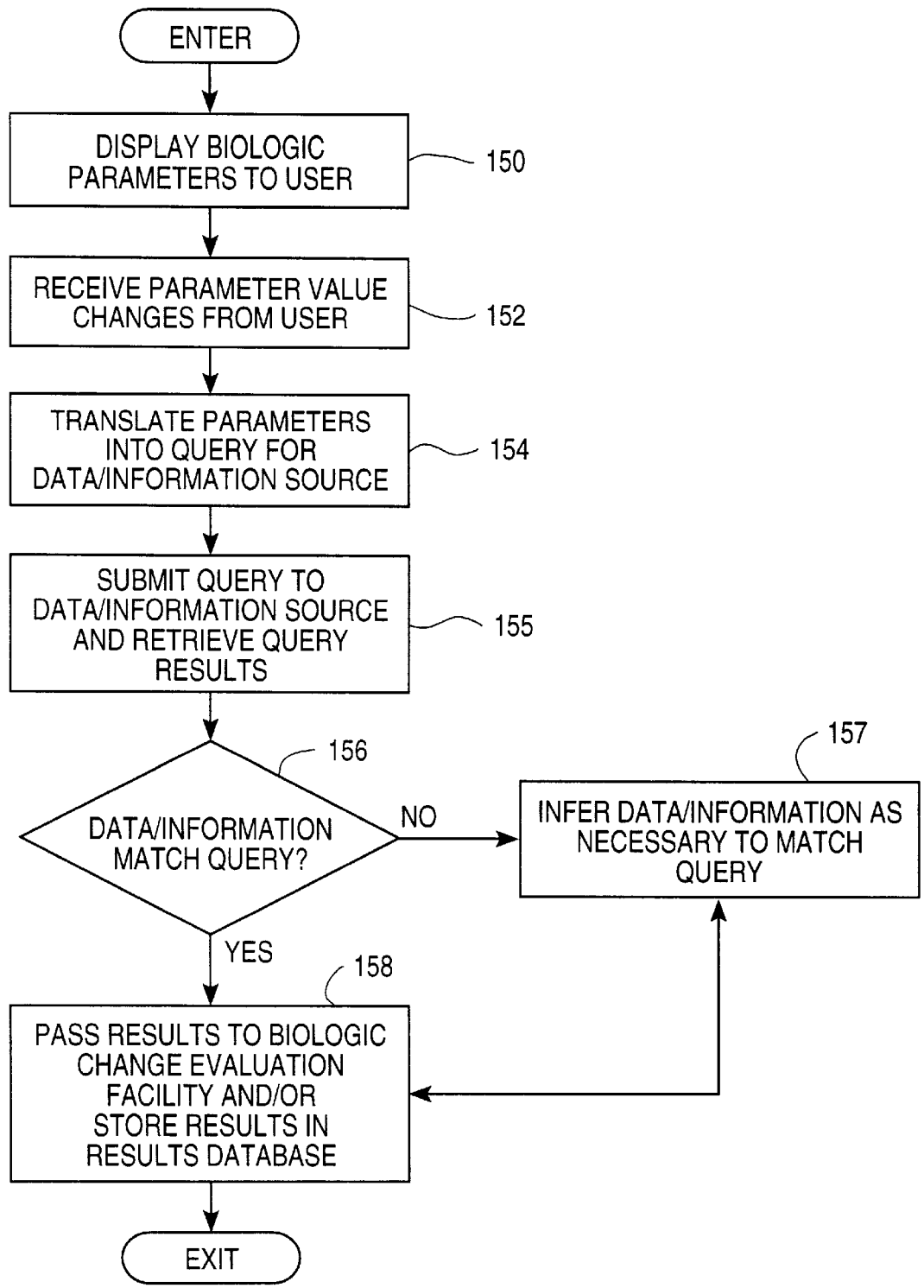
FIG. 6 shows a flow chart of processing performed by the Biologic Manipulation Tool.

FIG. 6 shows a flow chart of the processing performed by Biologic Manipulation Tool 220. This tool first presents 150 parameters relating to the biology of interest to the user via a user interface. The user interface allows the user to change 152 the input parameters to tailor the type of information developed by Biologic Manipulation Tool 220. The changed and unchanged parameter values are translated 154 into a query for Data/Information Source 20. The particular form of the query reflects the type(s) of data and information stored in Data/Information Source 20.

The query is formed using a query generation component of Biologic Manipulation Tool 220 that is specifically written to interface to the existing data source. If the data source is an SQL database, then an SQL query is composed programmatically from the user's input. If the data source is a simulation, then a set of simulation parameter values are passed to the simulation through a mechanism specific to the implementation (e.g., dynamically through Dynamic Data Exchange under Windows 95™ or perhaps through an electronic file that can be read by the simulation) and the simulation is run. Similar logic applies to other potential data sources.

Thus, Biologic Manipulation Tool 220 submits 155 the query to Data/Information Source 20, and the query retrieves data and information about a disease process related to the parameters of interest input by the user.. Upon receiving the data and information from the query, Biologic Manipulation Tool 220 determines 156 whether the retrieved results match the original request for data/information by the user. If the results do not match, the results are inferred 157, to the extent necessary, from the retrieved data to match the request as closely as possible (discussed in greater detail below). Finally, Biologic Manipulation Tool 220 passes 158 the query results to Biologic Change Evaluation Facility 220 and/or Results Database 22.

As mentioned, in the case of an inexact match, Biologic Manipulation Tool 220 retrieves all closely related cases and infers the outcome associated with the user's parameter selections. Retrieving closely related cases involves knowledge about the disease under investigation and the data source itself. This knowledge can be implemented in the form of rules, or other comparable knowledge representation techniques, and is used by Biologic Manipulation Tool 220 to determine, for instance, that parameter values are closely related if they are within 50% of the user supplied value. A query to the data source then retrieves all cases within the parameter boundaries. This knowledge may also be directly encoded in the structure of the data source. Closely related cases may be in the same table in a relational database. Finally, a learning algorithm, neural net, or case-based reasoning technique could be employed to automatically define closely related cases.

Once the closely related cases have been retrieved, Biologic Manipulation Tool 220 uses expert knowledge to combine the data in the closely related cases to infer the disease progression for the user-specified parameters. The inferred disease progression information is formed from expert knowledge, implemented as software code in the form of rules or other comparable method for inexact reasoning, about how cases should be aggregated or how interpolation should be performed, and the results of the analysis are stored in Results Database 22.

The process of receiving user input parameters, searching Data/Information Source 20 for information related to the parameters, developing data about disease progression, and storing the results may be repeated by the user one or more times. After one or more iterations of developing relationships in the form of biologic changes and corresponding changes in disease progression under a variety of parameters, Results Database 22 contains a series of records of biologic changes and the resulting disease progression. This information is then used by Biologic Change Evaluation Facility 222.

Figure 7:
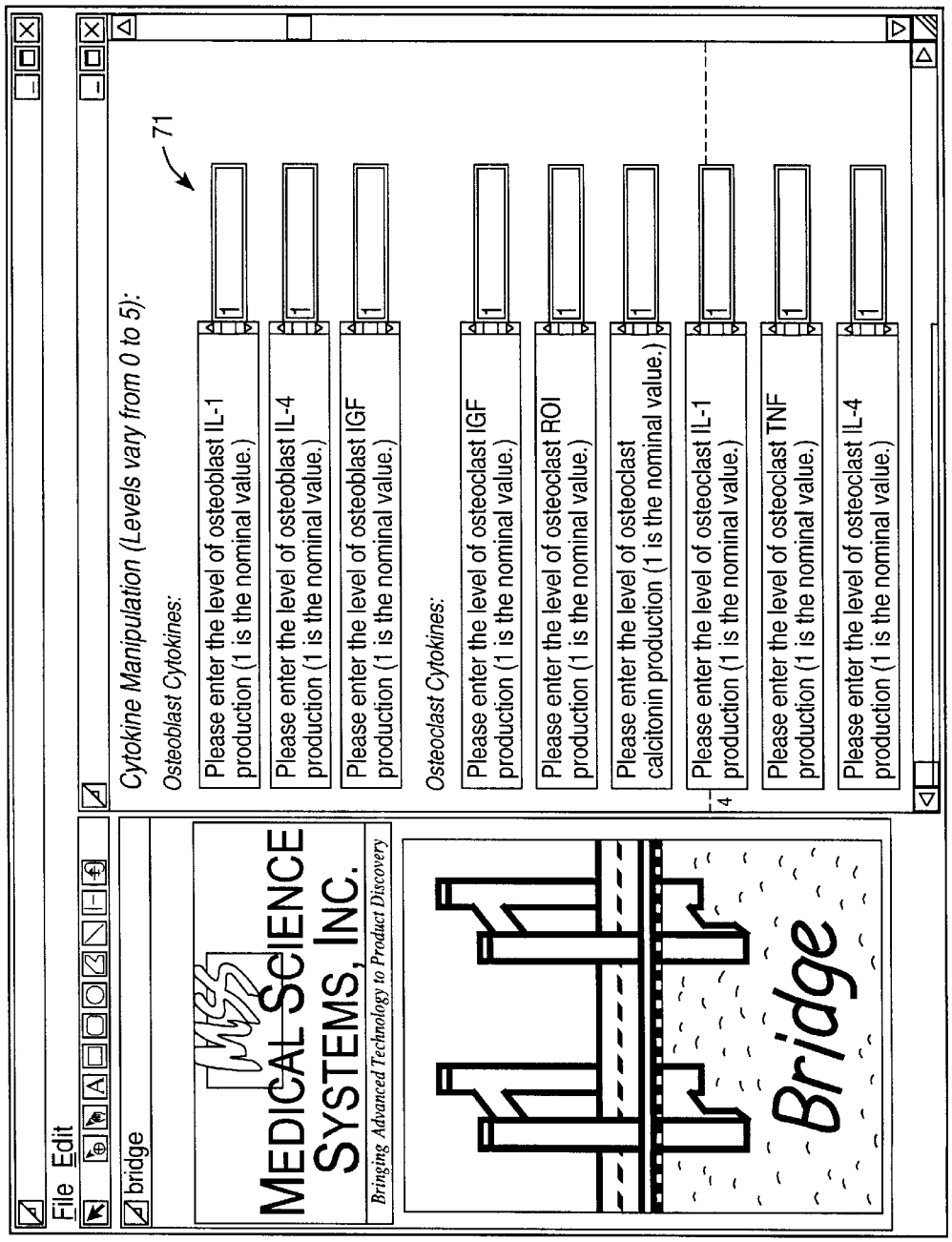
FIG. 7 shows a sample user interface for the Biologic Manipulation Tool.

FIG. 7 shows an example interface to Biologic Manipulation Tool 220. In general, a user interface for this tool reflects the underlying biology being studied. This user interface allows a user to alter parameters used by Biologic Manipulation Tool 220 in developing data about a disease process. In the example user interface of FIG. 7, a user can manipulate biologic parameters 71, defining levels of cytokine production for various cells, specifically osteoblasts and osteoclasts. Biologic Manipulation Tool 220 uses these parameters 71 to form a query of Data/Information Source 20 to obtain disease progression measures for osteoporosis. The resulting disease progression measures allows the user to examine how increased or decreased production of cytokines affects the disease progression of osteoporosis.

The screen shown in FIG. 7 depicts the first two steps of the Biologic Manipulation Tool 220 process (see FIG. 6). The user interface of FIG. 7 displays parameters 71 that can be manipulated by the user. A user is able to enter changes to default values established by the biology of the disease process. After the user makes changes, Biologic Manipulation Tool 220 translates the parameter values into an appropriate query for Data/Information Source 20, queries the source, and retrieves the results of the query.

Biologic Change Evaluation Facility

The second component of Target Discovery Explorer 12, Biologic Change Evaluation Facility 222, culls and processes the disease progression data generated by Biologic Manipulation Tool 220 about how the disease progression changes, and displays relationships between the manipulations in the biology and resulting changes in biologic attributes, such as measures of the disease progression, to the user. Some changes in the biology may affect one or more disease progression measures, but not others. Some changes in the biology may actually worsen the disease progression as assessed by disease progression measures. Biologic Change Evaluation Facility 222 allows a user to repeatedly query Results Database 22 to find the combination of biologic changes that yields the most positive effect on all disease progression measures. As such, Biologic Change Evaluation Facility 222 is a data visualization and analysis tool for viewing and exploring highly multivariate and multidimensional data. Ultimately, by effectively using Target Discovery Explorer 12, the user is able to design or find a potential intervention that provides the optimal change in the biology resulting in the most positive alteration in disease progression.

Figure 8:
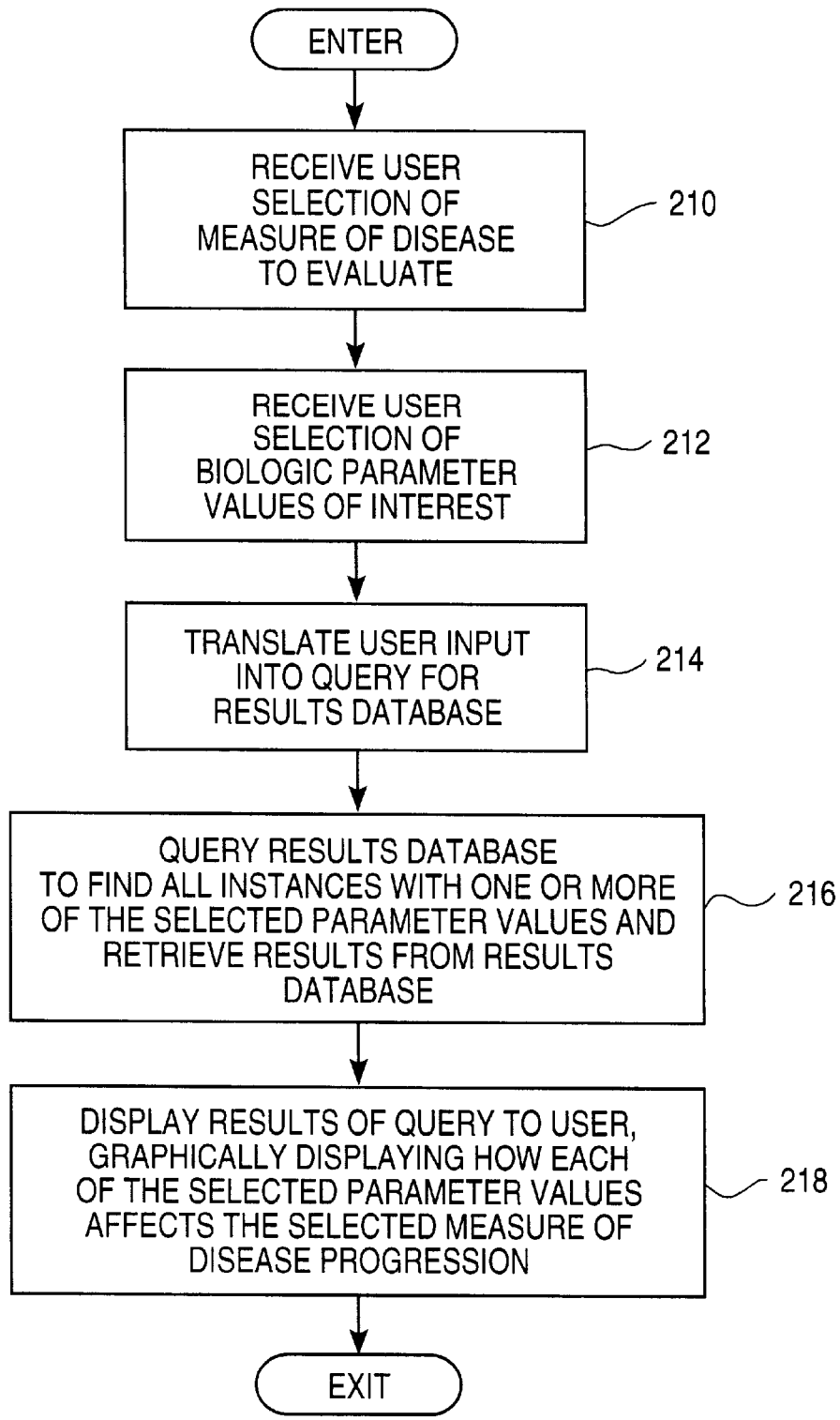
FIG. 8 is a flow chart of processing performed by the Biologic Change Evaluation Facility.

FIG. 8 is a flow chart showing the processing performed by Biologic Change Evaluation Facility 222. This facility first receives 210, 212 user selections of measures of disease progression to be evaluated and the values of biologic parameter(s) of interest. This information is translated 214 into a query of Results Database 22 and the results are returned 216 to Biologic Change Evaluation Facility 222. Finally, the results of the query are displayed 218 graphically to the user. The graphical display shows how each selected parameter value affects the disease progression measures. For example, the user may be interested in seeing how the level of interleukin-1 (IL-1) affects bone mineral density changes. Biologic Change Evaluation Facility 222, under user direction, creates a graph plotting IL-1 level against bone density loss. Or, if the user specifies only interest in IL-1 levels of, perhaps, 50% and 80% the normal value, Biologic Change Evaluation Facility creates a table of the average bone density loss for 50% and 80% of normal IL-1 levels. The user specifies the format of the report and Biologic Change Evaluation Facility 222 queries Results Database 22 and produces the report.

In general, the potential methods of displaying the query results fall into three categories: graphical, numerical/ statistical, or animation. Graphical displays plot actual values or category counts to produce line or bar graphs. Numerical/statistical displays exhibit descriptive statistics such as means and standard deviations. Finally, animation is used to show how relationships change overtime. For example, in osteoporosis, a user might select an animated display to evaluate the increasing risk of microfractures in the spine across the lifespan of an individual. The user selects the format of the display based on his/her needs.

Figure 9:
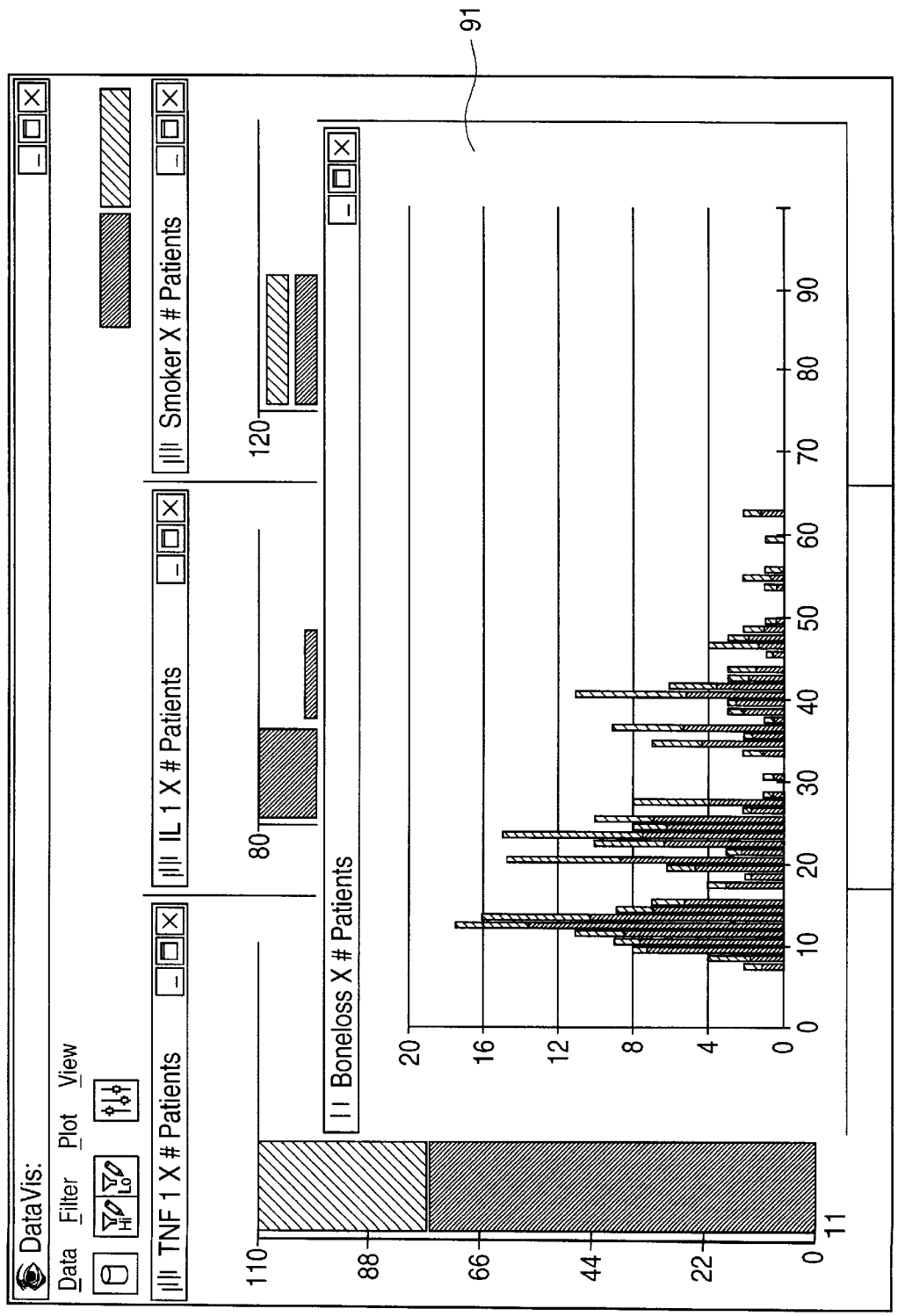
FIG. 9 shows an example user interface for the Biologic Change Evaluation Facility.

FIG. 9 shows one user interface for Biologic Change Evaluation Facility 222. In general, the facility includes a variety of user interfaces, each providing a different view, or method of analysis, of the information developed by the facility, for showing the relationships in between changes in various biologic parameters and disease progression measures. In the example in FIG. 9, a user graphically views the results of changes in the disease biology on one measure of disease progression as developed by Biologic Change Evaluation Facility 222. In the example interface shown, the graph 91 shows that changes to tumor necrosis factor (TNF) and IL-1, input by the user to Biologic Manipulation Tool 220, produce poor disease progression as measured by bone mineral density loss. This is reflected in the highlighted, high-end bone loss values.

In relation to osteoporosis, Target Discovery Explorer 12 can help a user develop information about various proposed interventions. In this example, Target Discovery Explorer 12 accesses Data/Information Source 20, which contains data and information from a clinical trial, laboratory research program, physician's practice, expert judgment, and/or a simulation of bone remodeling. It processes these data under instruction of the user. The processing results in a synthesis of disease progression information from which the user may judge that particular leverage points in the biology appear to have the desired or optimum results. This synthesis assists the user in determining whether or not changes in some chemical controls of the bone remodeling process would be effective as a proposed intervention.

For example, assume that Data/Information Source 20 for Target Discovery Explorer 12 includes a simulation model of bone remodeling. The user inputs parameters to Biologic Manipulation Tool 220, which systematically alters the levels of chemical parameters in the model, such as insulin-like growth factor (IGF), IL-1, and interleukin-4 (IL-4). These levels could be tuned independently under the direction of the user or Biologic Manipulation Tool 220. The model is then run to establish the results of the changes on the bone remodeling rate and overall bone density over a defined period of time. More specifically, the user might input parameters that result in the simulation model causing osteoblasts to produce twice the normal level of IGF and one quarter of the normal levels of IL-1 and IL-4. The simulation is run to project the bone density and remodeling rates that result from these changes, the data are collected every month for 10 years, and the resulting disease measure projections are saved in Results Database 22. Alternatively or additionally, Data/Information Source 20 may include a database of laboratory research results that is queried to find the results of these changes in laboratory experiments on bone.

Once a series of runs has been executed with different user and system input values and the output results written to Results Database 22, Biologic Change Evaluation Facility 222 enables the user to mine Results Database 22 for relationships between biological changes and disease progression measures to find the set of changes that produce optimal disease outcomes. In this example, Biologic Change Evaluation Facility 222 queries Results Database 22 at the request of the user to find, for example, the range of IGF production (say 95–150% of normal levels) coupled with the range of IL-1 and IL-4 production (say 50–100% of normal levels) yielding increased bone mineral density when estrogen is at post-menopausal levels.

After identifying a biological target, the user can simulate the effect of known interventions with Target Discovery Explorer 12 to identify a proposed intervention. To do so, the user inputs the known effects of an extant intervention on the production of, for instance, IGF, IL-1, IL-4 and other chemical signals until a regimen consisting of one or more interventions is found that maintains these chemicals within their ideal range.

In summary, Target Discovery Explorer 12 assists the user in identifying potential leverage points for a potential intervention by providing a mechanism that supports the generation, exploration, analysis, and visualization of complex multidimensional, multivariate data to find important patterns in the data. Once a proposed intervention is identified, it can be output to Clinical Trials Explorer 14 to test the intervention in one or more simulated clinical trials, ultimately supporting the user's design of an actual clinical trial. The proposed intervention can also be analyzed for consumer benefit by PE Explorer 16. Finally, Disease Progression Explorer 17 can help educate the patient and practitioner on the merit of the resulting intervention.

CLINICAL TRIALS EXPLORER

The second step in the scientific process is hypothesis testing. Once a hypothesis has been formed, the implications of that hypothesis are examined in one or more rigorous, formal studies. Clinical trials involve hypothesis testing and their design and execution is the second step in the target development process. The hypotheses tested in clinical trials center around determining whether or not 1) the proposed intervention is effective in human populations, 2) there are patient conditions that limit or alter the effectiveness of the proposed intervention, and 3) the timing and/or therapeutic levels of the proposed intervention affect the disease outcome. Clinical trials ask the questions, "Does the proposed intervention affect the biology such that disease progression is halted or reduced?" and/or "What patient and intervention attributes modify the expected impact of the intervention and why?"

Clinical trials are very time consuming and costly and thus the design of a clinical trial is carefully evaluated prior to conducting the trial. The design process relies on an integrated and comprehensive understanding of the disease biology and of the hypothesized locus of the effect of the proposed intervention. It also requires an understanding of the appropriate regimen for delivering the intervention. For example, some interventions may affect a disease process in a single exposure to the patient. Others may need to be delivered for the duration of the disease or the duration of the patient's life. In the osteoporosis example, estrogen replacement therapy often begins at menopause and continues for the life of the patient. A therapeutic regimen for the common cold would have quite different characteristics. Clinical trials are designed to answer questions of the efficacy of the proposed intervention, the optimal regimen for delivering the intervention, and what the effects are for different patient types.

Clinical Trials Explorer 14 provides support for clinical efficacy analysis. Efficacy analysis performed by Clinical Trials Explorer 14 provides the following exemplary outputs: 1) the impact of a proposed intervention on a disease progression for a given patient type; 2) which patient types have the best outcomes and which patient types have the worst; and 3) the optimal intervention regimen across time for a given patient type. Other similar questions may also be addressed, while remaining within the spirit of the present invention. These questions are extremely difficult to answer using traditional laboratory/testing practices due to the need to analyze so many different variables, thus these practices are unable to scale up to real world usage conditions. Clinical Trials Explorer 14 provides a testbed for answering these questions in which the user can explore the limits of efficacy of a proposed intervention under a wide variety of usage conditions and with respect to a large number of different combinations of patient attributes, prior to actual implementation of the clinical trials themselves. In this manner, the user can design a clinical trial that is specifically evaluates the efficacy of an intervention with respect to specific patient attributes and other preselected criteria. This ability pre-assess the outcomes of clinical trials for particular combinations of variables is a tremendous advantage over conventional approaches, which often require multiple clinical trials at great expense to the intervention developer merely to understand the impact of a wide variety of these variables on disease progression.

Figure 10:
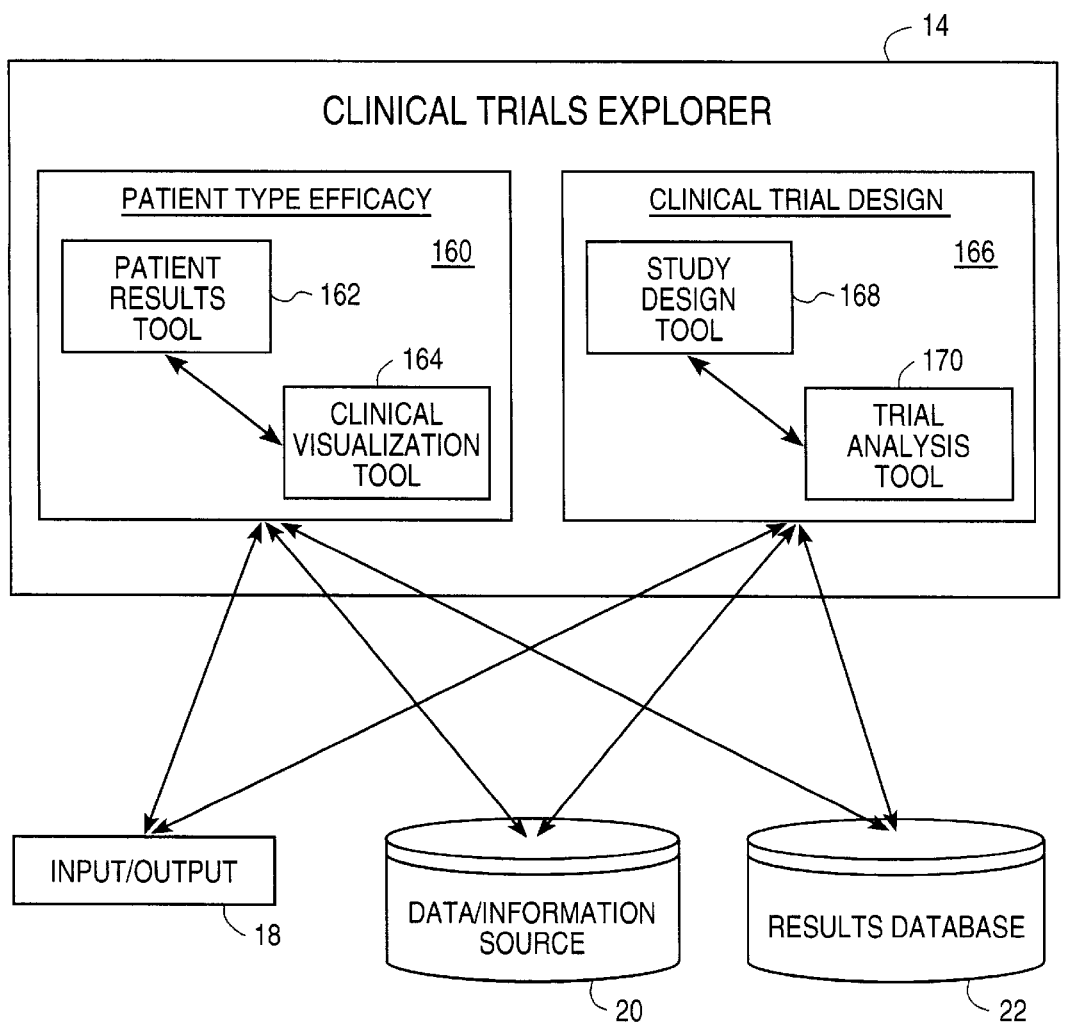
FIG. 10 is a block diagram showing the Clinical Trials Explorer.

As shown in FIG. 10, the primary components of Clinical Trials Explorer 14 are Patient Type Efficacy Module 160 and Clinical Trial Design Module 166. Patient Type Efficacy Module 160 is composed of Patient Results Tool 162, a combined instance of Query Processor 226 and Results Synthesizer 228, and Clinical Visualization Tool 164, an instance of Results Synthesizer 228. Clinical Trial Design Module 166 is composed of Study Design Tool 168, an instance of Query Processor 226, and Trial Analysis Tool 170, an instance of Results Synthesizer 228. It should be noted that while FIG. 10 shows the components of Clinical Trials Explorer 14 interacting only with Input/Output 18, Data/Information Source 20, and Results Database 22, Clinical Trials Explorer 14 could also be embodied in a system such as that shown in FIG. 2, without departing from the spirit of the present invention.

The two primary components of Clinical Trials Explorer 14, Patient Type Efficacy Module 160 and Clinical Trial Design Module 166, represent the two major functions of this Explorer: 1) to provide easily interpreted information about how a disease will progress in a single patient type given a specific intervention, and 2) to provide an easy way to compare such results across patient types and intervention approaches in order to identify the best patient disease outcomes to include in the design of a clinical trial. The following sections describe these two major components in further detail.

Patient Type Efficacy Module

Figure 11:
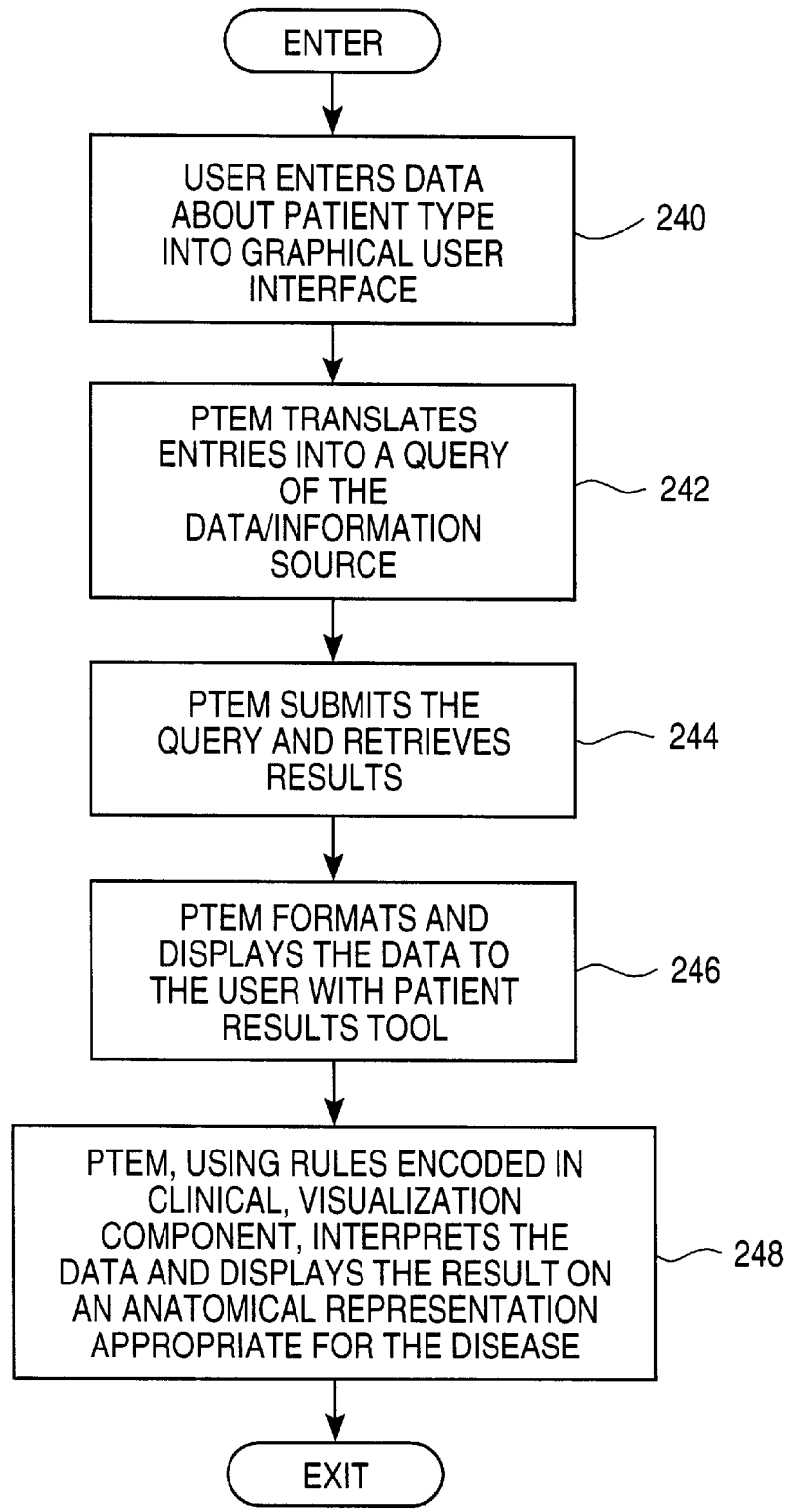
FIG. 11 shows a flow chart of the overall processing of the Patient Type Efficacy Module.

FIG. 11 shows a flow chart of the overall processing of Patient Type Efficacy Module (PTEM) 160. PTEM is a facility for examining proposed interventions for a single type or class of patient. This facility is used to understand the rationale and/or predict the disease progression for a specific patient. The user enters the patient attributes and the intervention regimen, and PTEM queries Data/Information Source 20 to retrieve the disease progression for this type of patient on the specific regimen. Finally, PTEM formats and displays the results to the user.

PTEM includes Patient Results Tool 162 and Clinical Visualization Tool 164. PTEM develops information about disease progression measures at a variety of levels, from the cellular level up to the presenting signs and symptoms of the disease, for a particular patient type under varying conditions as defined by user input. To do this, Patient Results Tool 162 dynamically constructs a query or series of queries of Data/Information Source 20 based on the user's input parameters and then retrieves the results of the query. Then Patient Results Tool 162 displays the disease progression over time for the given patient type and intervention regimen in the user selected format. As shown in FIG. 11, the user first enters 240 data about the patient type and intervention regimen into the graphical user interface. Patient Results Tool 162 then translates 242 these entries into a query of Data/Information Source 20, submits the query and retrieves the results 244, and synthesizes and formats the data/information in a tabular or graph format for display 246 to the user. Output to the user also includes the patient attributes, including risk factors, as well as any intervention regimen information.

Upon user request, Clinical Visualization Tool 164 interprets the results obtained by Patient Results Tool 162 using expert knowledge supplied by experts to show how the disease progression might appear clinically to a practitioner. The expert knowledge is translated into an expert knowledge base 182 and is used to map the disease progression data found by Patent Results Tool 162 to a depiction of the clinical manifestation of the disease, such as an anatomic representation. In the osteoporosis example, expert knowledge may indicate that a one standard deviation decrease in bone mineral density leads to a 2-fold increase in fracture risk. This would be translated into postural changes resulting from micro-fractures in the spinal column, leading to the clinical manifestation of slight spinal curvature. Thus, for example, the Patient Results Tool 162 may plot a bar graph in 2 or 3 dimensions of bone mineral density for a patient type under various regimens, and then the Clinical Visualization Tool 164 interprets this data using expert knowledge to display a graphic of spinal curvature over time. In this way, expert knowledge is leveraged to project the disease progression onto an appropriate clinical representation of the patient signs and symptoms of the disease. This is generally based on an anatomical representation, using Disease Progression Explorer 17 as the mechanism to do the analysis. The anatomical representation may be presented in two or three dimensions, as an animation, or simply as a graph. In the osteoporosis example, a number of bitmap images of spinal columns in various states of curvature are stored, and Clinical Visualization Tool 164 selects and displays the appropriate bitmap image based on the projected disease progression for the patient, and the patient attributes. If the user selects an animated display, the images are presented in a timed series to show how the spine curves over time. Thus as a whole, PTEM 160 receives data from the user about patient attributes and intervention regimens and outputs data as plots, graphs, or mapped into clinical manifestations of the disease on a graphic image.

Figure 12A:
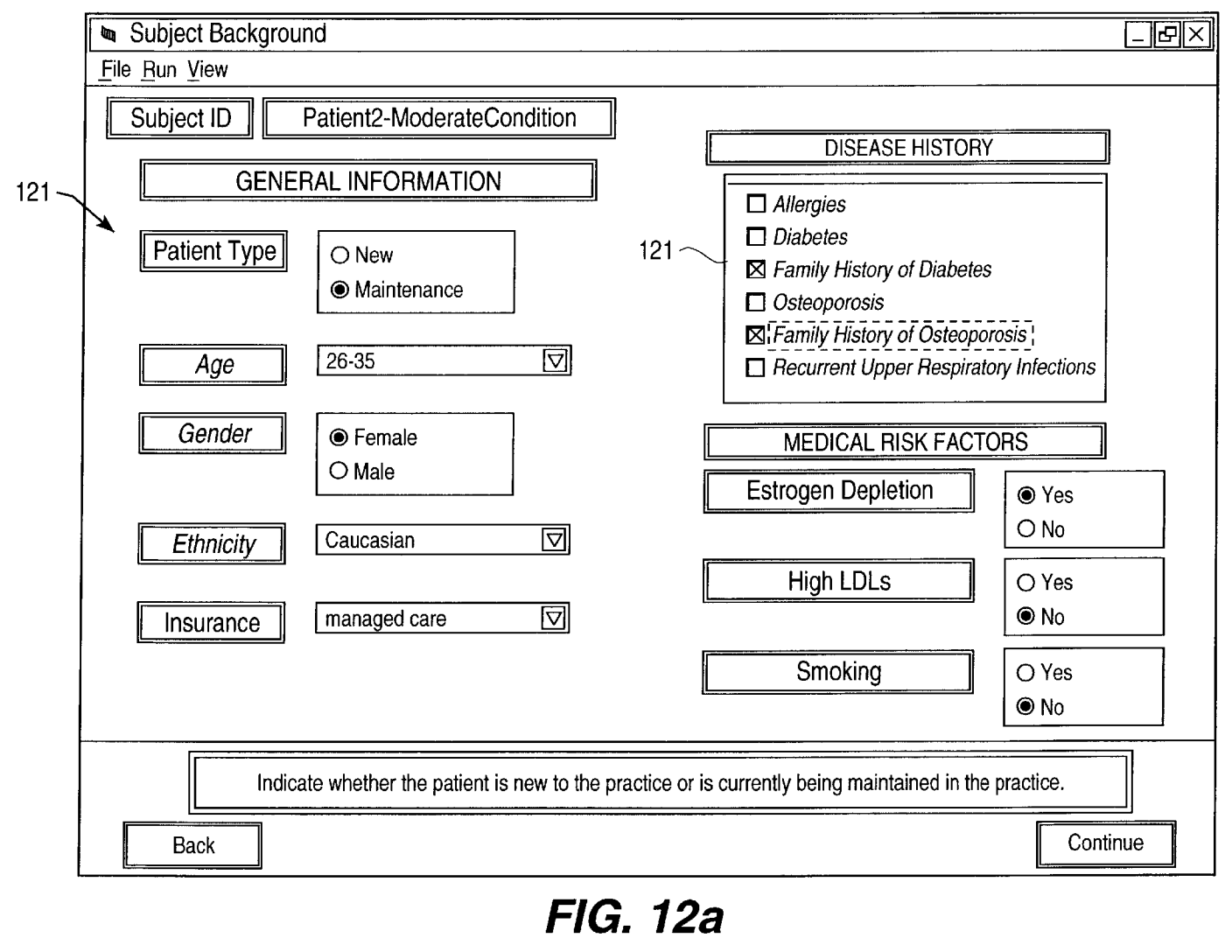

FIG. 12a and FIG. 12b show examples of the graphical input interface for Patient Results Tool 162. As shown in FIG. 12a, this module allows the user to enter data about patient attributes. As can also be seen, the labels and selections for describing a patient are designed to be natural and intuitive. In general, the labels and selections outline information typical of a patient history, and the figure shows one of many possible examples of such an interface. As illustrated in FIG. 12a, the input attributes 121 may include, but are not limited to, general information such as Patient Type, Age, Gender, Ethnicity, and Insurance Coverage; Disease History; and Medical Risk Factors. The input attributes 123 of the proposed intervention regimen under study are shown in FIG. 12b.

Figure 13:
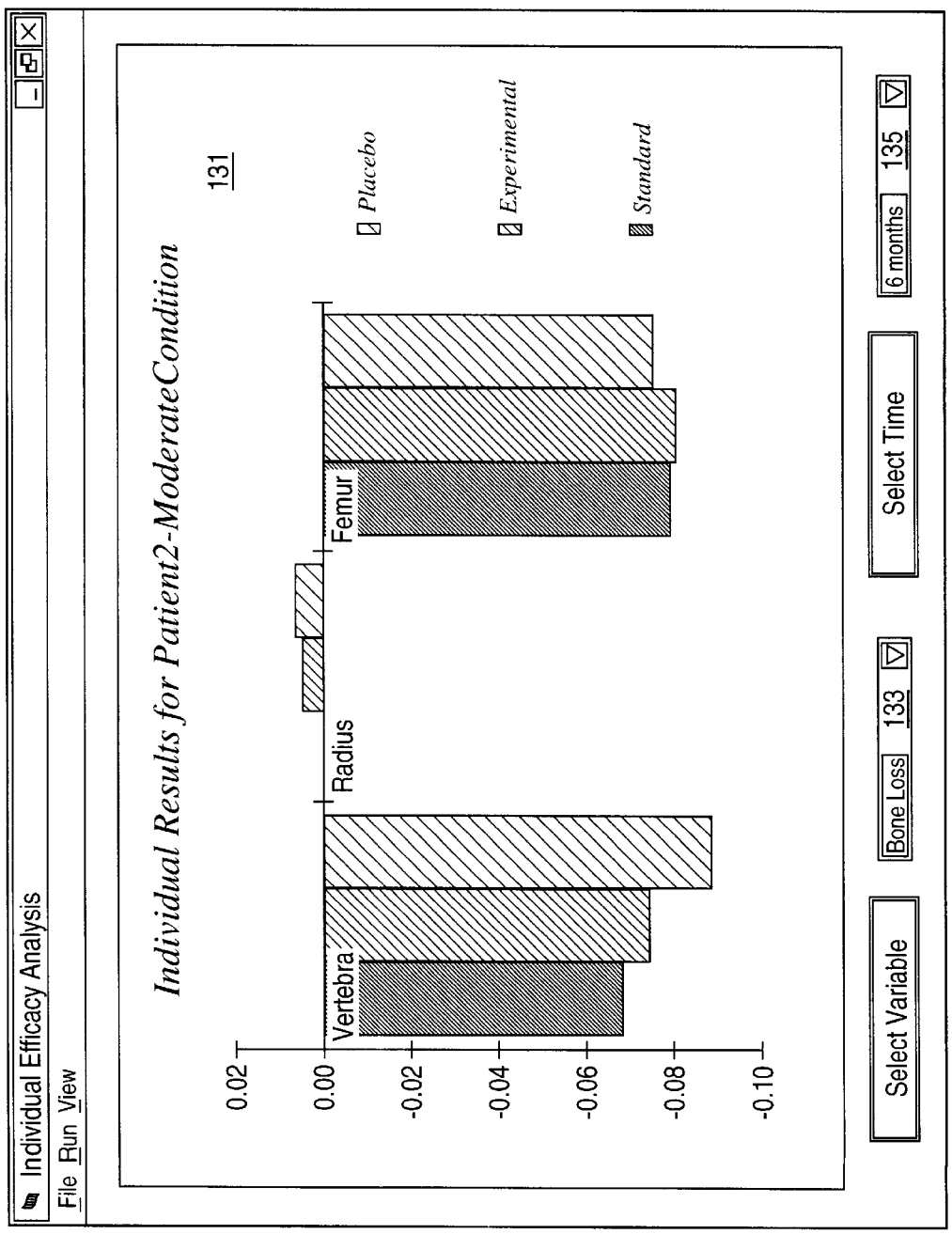
FIG. 13 is an example graphical user interface produced by the Patient Results Tool.

FIG. 13 is an example of a graphical results interface for Patient Results Tool 162. In general, the user interface to this tool shows changes in some disease progression measures for the type of patient under study, as shown in the example of FIG. 13. The graphical interface provides a representation of the disease progression measure for the patient under various intervention conditions. The disease progression measure is generally for one or more clinical attributes that represent key symptoms of the disease. Results for a patient are displayed, for example, under three typical alternative intervention regimens: placebo, experimental intervention (i.e., the proposed intervention), and the current standard method of intervention. The example interface of FIG. 13 shows in a bar chart 131 a disease progression measure of mean bone mineral density changes (i.e., bone loss) based on parameters from the osteoporosis example. The user may select which disease progression measures to view and the time course for changes in the measures by using the user interface buttons 133, 135. The measures and time increments, however, are defined by the data available from Data/Information Source 20.

Figure 14:
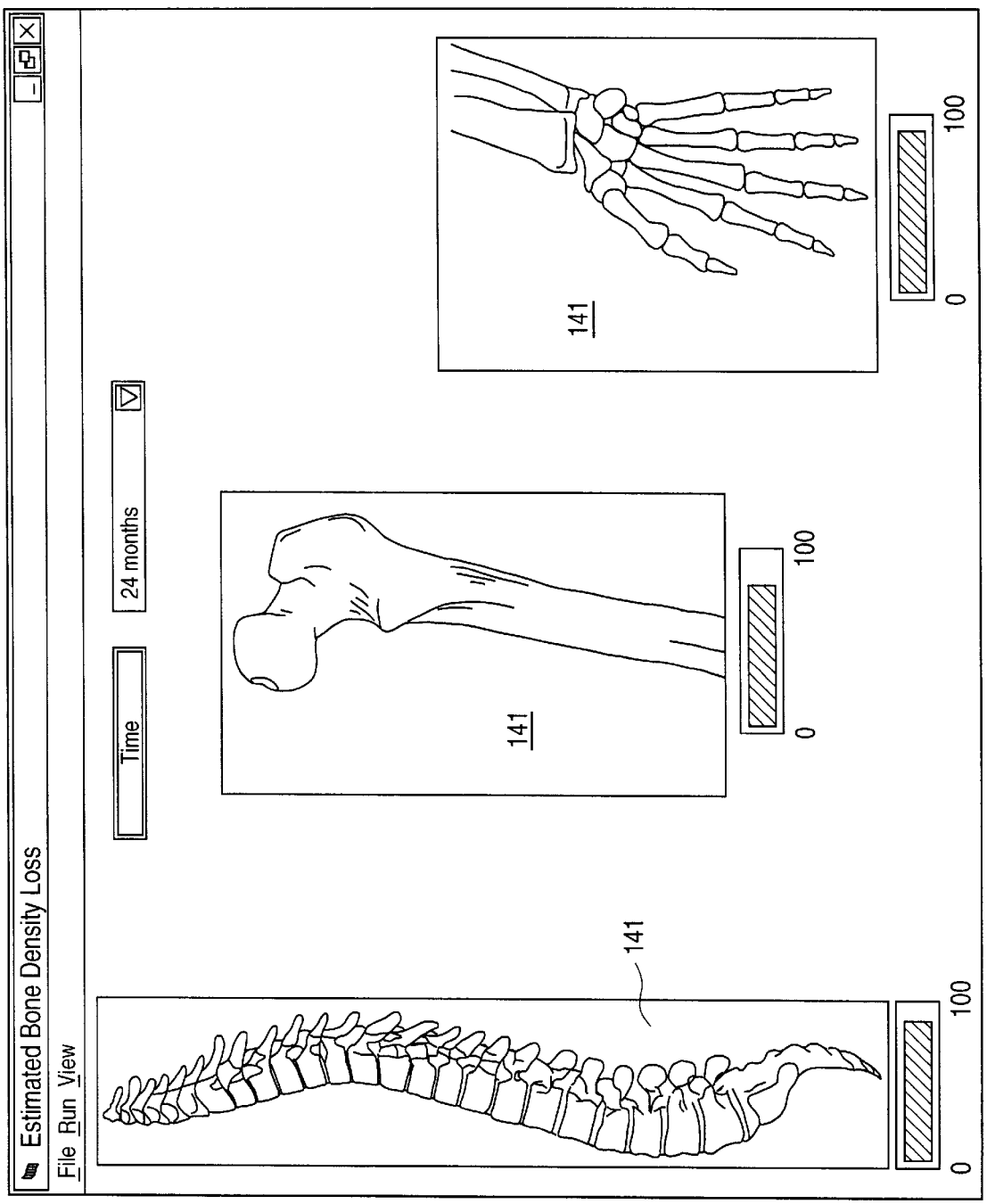
FIG. 14 is an example graphical user interface of the Clinical Visualization Tool.

FIG. 14 is an example graphical user interface for Clinical Visualization Tool 164. This tool uses the initial condition of the patient acquired from the user's input and data gathered from Data/Information Source 20 to infer the likely clinical manifestation of disease progression over time. The process of inferring the clinical manifestation is based on expert knowledge, which is encoded into a knowledge base and implemented as part of Clinical Visualization Tool 164, or stored in Data/Information Source 20. The expert knowledge is encoded as a set of rules and facts or some other method of representation that allows the software to translate disease progression onto the appropriate graphical representation of the clinical state of the disease. The knowledge is appropriate for the disease and the measures of disease progression. For example, as shown in FIG. 14, in a system for analysis of osteoporosis, the progression of osteoporosis is displayed as in various images 141 showing changes in bone density at important loci of the body, such as the vertebra, femur, and radius. Shading and/or animation of the anatomical representation of the area being analyzed may be used to show progression of a disease. FIG. 14 also indicates how disease progression is additionally represented by percentage bar graphs below each anatomically-based representation.

Clinical Trial Design Module

PTEM allows the user to view the disease progression for a single patient type to understand the results for that particular type of patient. Clinical Trial Design Module 166 produces the disease progression results for groups of patient types, such as those types that are included in a potential clinical trial design. A clinical trial is an experiment, therefore Clinical Trial Design Module 166 operationalizes the process of supporting clinical trial design using an experimental paradigm. The user designs a wide variety of potential clinical trials with Clinical Trial Design Module 166, and this module runs the studies by gathering the relevant data from Data/Information Source 20 and presenting the results to the user. In this way, the user evaluates alternative clinical trial designs and/or predicts the outcome of a completed design without having to actually implement the clinical trial itself. The user might also use Clinical Trial Design Module 166 to understand the outcome of a clinical trial that provided unexpected results by running the study in Clinical Trial Design Module 166 to gather information on the biological and patient effects that generated the unexpected result (e.g., biological parameters and/or patient attributes not controlled for in the study). These approaches enable the user to design clinical trials using a bottom-up, data driven approach based on identifying significant relationships in the underlying biologic processes, disease progression measures, and patient attributes. Clinical Trial Design Module 166 comprises Study Design Tool 168 and Trial Analysis Tool 170.

Figure 15A:
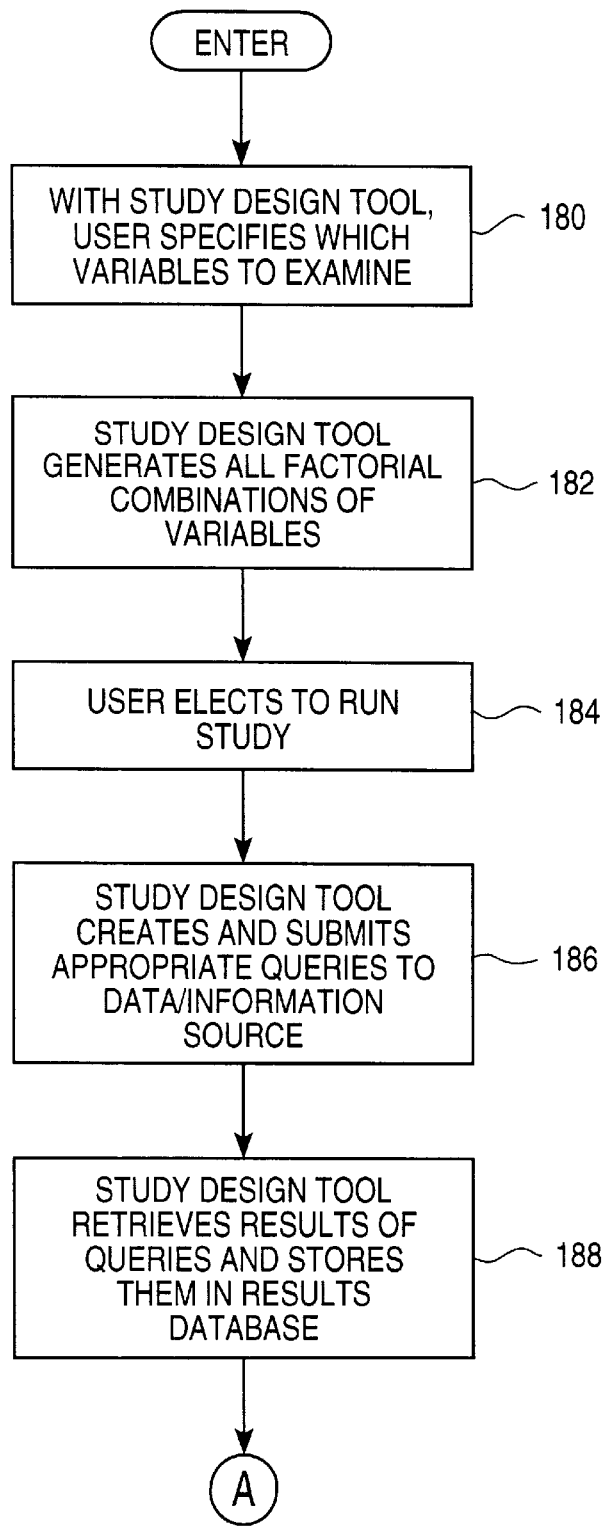
FIG. 15*a* and FIG. 15*b* together form a flow chart showing the processing performed by the Clinical Trial Design Suite.
Figure 15B:
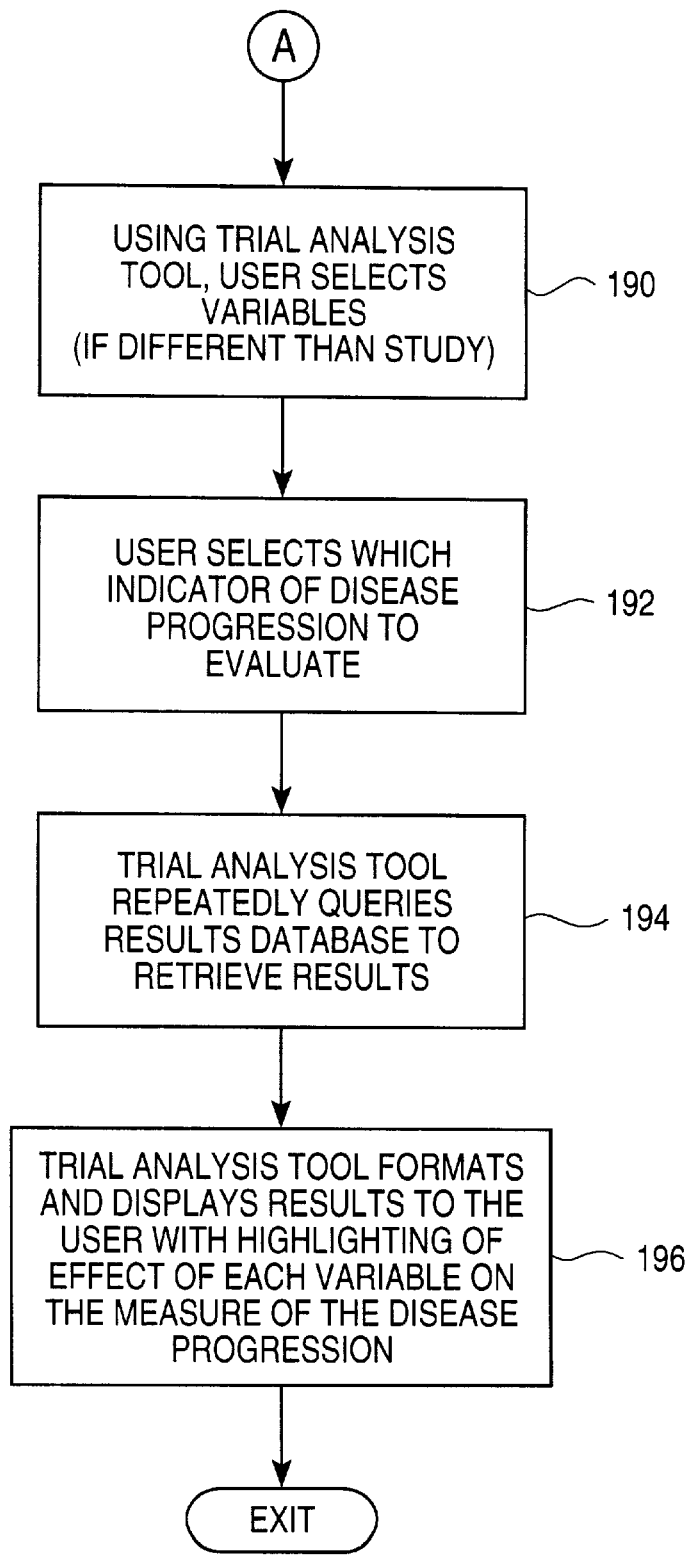

FIG. 15a and FIG. 15b together form a flow chart showing the processing performed by Clinical Trial Design Module 166 and, in particular, the processing performed by its major components, Study Design Tool 168 and Trial Analysis Tool 170. Study Design Tool 168 allows a user to systematically vary patient attributes to obtain the effect of a proposed intervention on different types of patients. Trial Analysis Tool 170 allows the user to view and analyze the results found by Study Design Tool 168 in order to identify patient types in which the intervention has the desired effect and those in which it has a negative or unexpected effect.

FIG. 15a shows the processing performed by Study Design Tool 168. Using Study Design Tool 168, the user specifies 180 the variables for inclusion in the proposed trial design. These variables include patient attributes, intervention attributes, the time course of the study, the regimen for delivering the intervention, and other variables that are of interest in the study design. When specifying which variables to include in the study, the user also specifies the range of the values of those variables to evaluate. For example, the user may be interested in smoking effects but only in terms of the differences between nonsmokers and heavy smokers, thus ignoring intermediate values of smoking. Study Design Tool 168 generates 182 the factorial combination of the variables across the ranges of interest to produce a full factorial study of the combinations of the variables under investigation. If the user wishes to decline certain combinations, that option is available. When the user elects 184 to run the study, Study Design Tool 168 dynamically creates and submits 186 the appropriate queries of Data/Information Source 20. Then Study Design Tool 168 retrieves the results and stores 188 them in Results Database 22.

Figure 16:
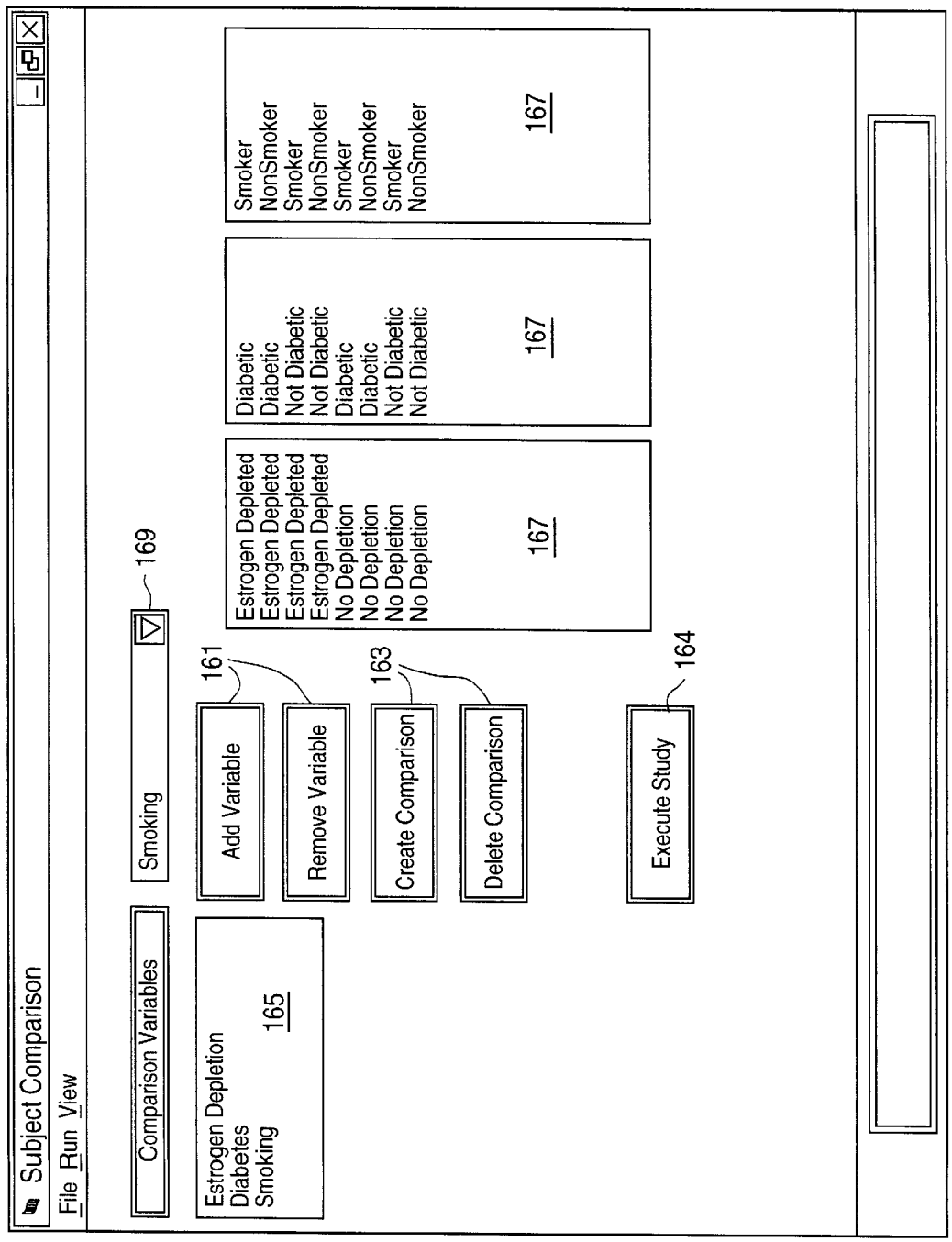
FIG. 16 shows an example graphical user interface for the Study Design Tool.

FIG. 16 shows an example graphical user interface for Study Design Tool 168. User controls 161 provide for selecting patient attributes, intervention attributes, biologic parameters, or other variables of interest for the study; other controls 163 enable creating and selecting factorial combinations. As shown in FIG. 16, patient attributes and other variables are selected from a drop down menu 169. List 165 shows the selected variables for analysis. When a variable is selected, the Study Design Tool 168 lists the factorial combination of all selected variables in the factorial combination list windows 167. The user then elects to run the study for any or all combinations of the variables with the execute button 169. That is, when the user selects the combinations of interest, Study Design Tool 168 repeatedly queries Data/Information Source 20 to retrieve the results of all combinations of patient types included in the study requested. The retrieved results are stored in Results Database 22 for use by Trial Analysis Tool 170.

Figure 17:
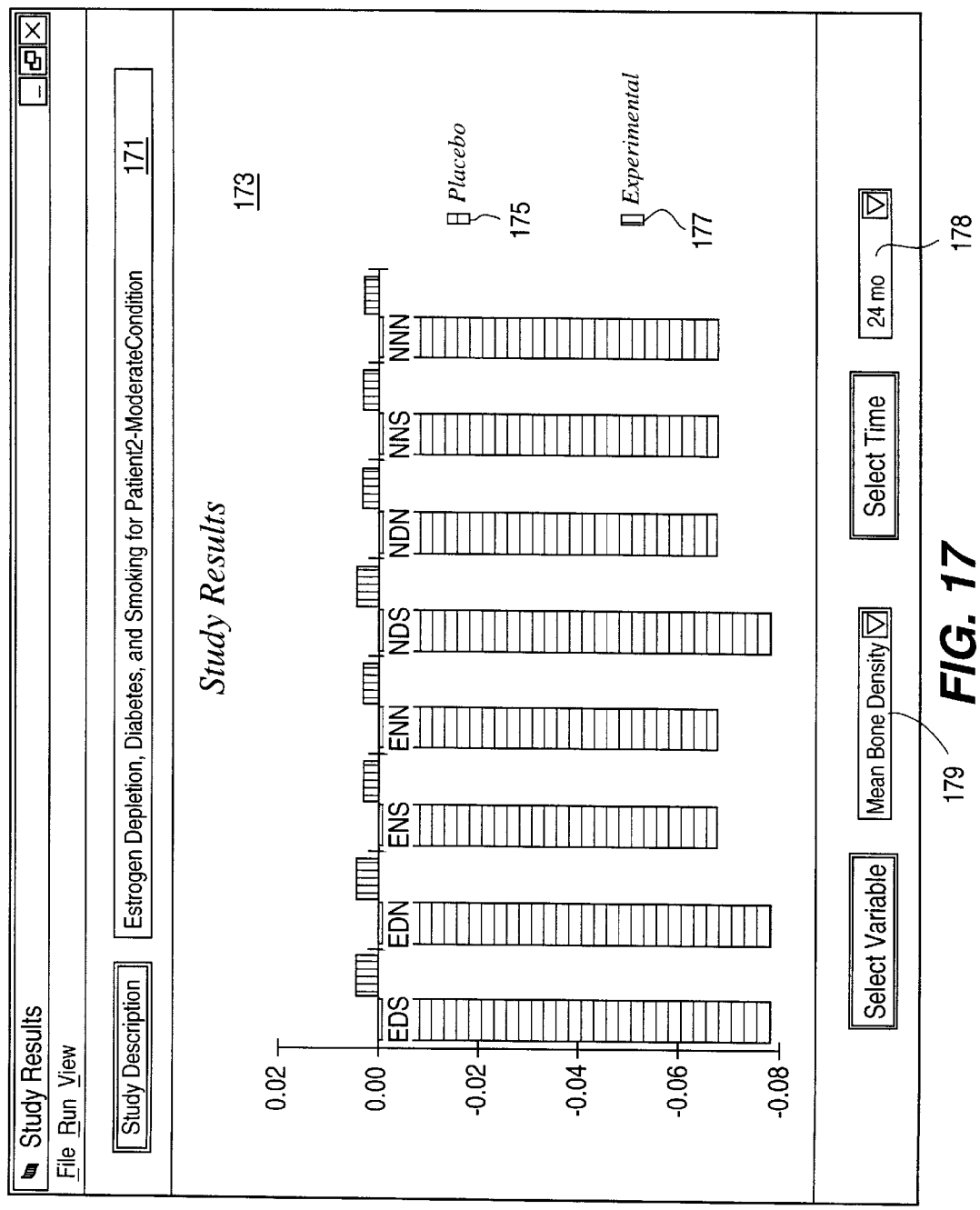
FIG. 17 shows an example user interface showing study results from the Trial Analysis Tool.

Trial Analysis Tool 170 comprises two components: 1) a component that presents the results of an individual study; and 2) a component that allows the user to view results across multiple studies to more fully evaluate the effect of variables of interest on the measures of disease progression. FIG. 17 shows an example graphical user interface for the first component of Trial Analysis Tool 170. This component gathers and displays the results of an individual study graphically for analysis by the user. The information presented by Trial Analysis Tool 170, as exemplified by FIG. 17, is produced by the queries of Data/Information Source 20 made by Study Design Tool 168 for all factorial combinations of the patient attributes or other variables included in the study. In the example shown, the user elected to evaluate all combinations of estrogen depletion, diabetes status, and smoking status, indicated in variable list 171. The screen shows a bar graph 173 depicting the disease progression measure of bone mineral density loss for each factorial combination of these variables, for both a placebo 175 and a proposed intervention 177. The user can view the effect of the proposed intervention on other disease progression measures by selecting the disease progression measure from menu 179, and the time scale from menu 178.

Trial Analysis Tool 170 also provides a means of data visualization and mining of Results Database 22 across different studies. FIG. 15b describes the processing performed by Trial Analysis Tool 170. The user selects 190 the variables under investigation (i.e., patient attributes, intervention attributes, and the like.) and the range of their values for analysis. The user also selects 192 the disease progression measure(s) under consideration. Trial Analysis Tool 170 repeatedly queries 194 Results Database 22 to retrieve the results. The results may be presented 196 in a number of ways, for example 1) the mean value of the disease progression measure(s) for each combination of study variables; 2) the number of database entries with specific values on the disease progression measures for those records that share the defined input variable values, or 3) color-coded relationships between the value of the disease progression measure(s) and input variable values. For example, if the user wishes, the entire range of values on the disease progression measure(s) stored in Results Database 22 are shown. The user may elect to highlight those values that are associated with smokers. This distinguishes the range of observed disease progression for smokers vs. nonsmokers. The user can condition the highlighting on any number of patient or intervention attribute values to find combinations that distinguish good and bad disease progression.

Figure 18:
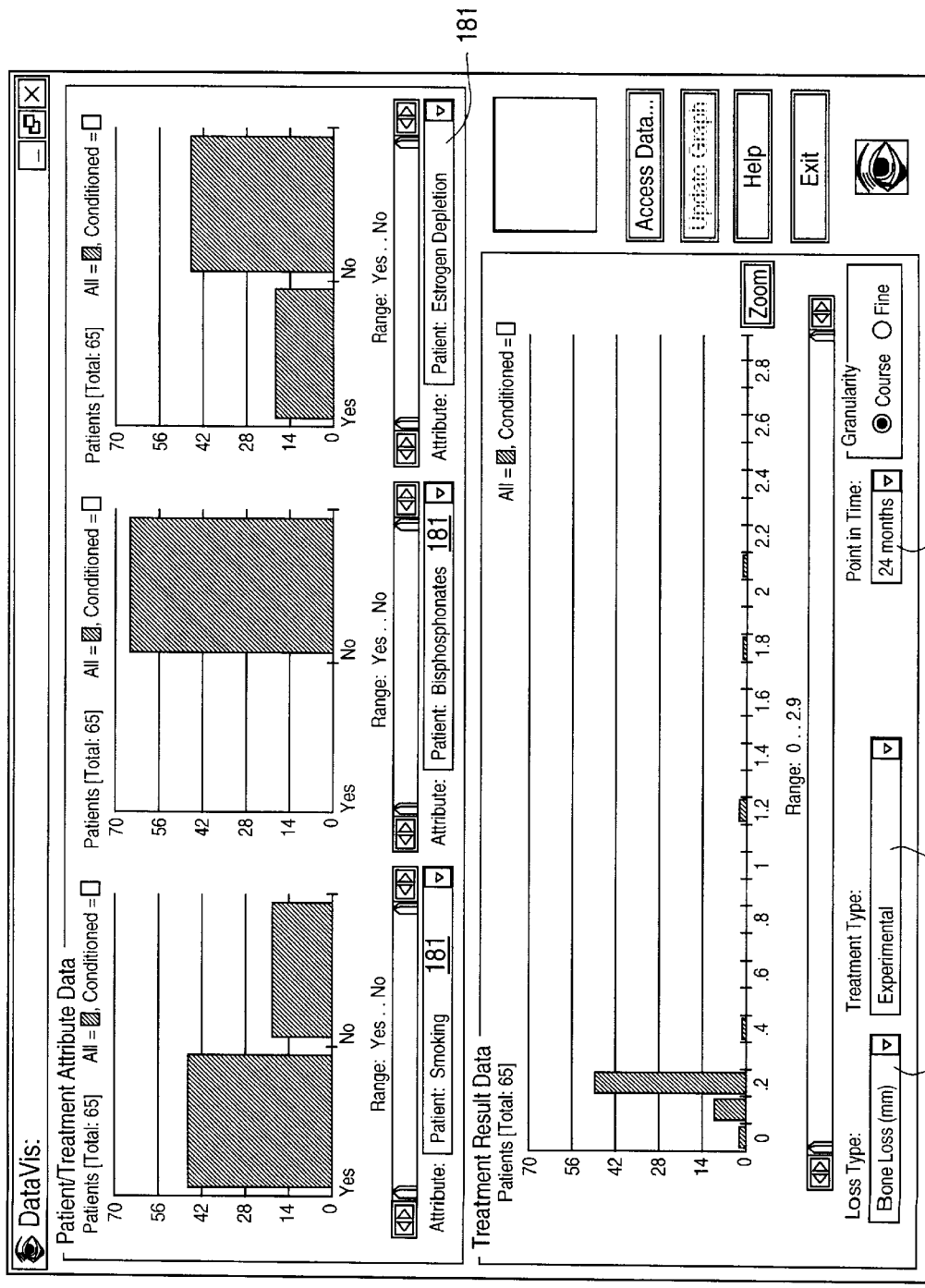
FIG. 18 is a graphic interface generated by the Trial Analysis Tool showing correlations between patient variables and disease outcomes.

As shown in FIG. 18, Trial Analysis Tool 170 uses data stored in Results Database 22 by Study Design Tool 168 to display correlations or relationships between selected ones of the input variables (including patient attributes 181, and intervention attributes 185) and disease progression measures 183, allowing the user to better understand and visualize patterns in the data that inform the clinical trial design process. The user can select various combinations of these inputs from the various drop down menus 181, 183, 185, along with changing the time scale 187. The user may view these relationships in a variety of ways to support this process. Views that highlight the relationships between input variables and disease progression measures help the user answer questions about how specific patient and intervention attributes affect the course of the disease. Views showing the inverse relationship, allowing the user to select a value of a disease progression measure and see the distribution of patient and intervention attributes that resulted in that value, help the user to find out which patient types and/or intervention attributes are associated with better and worse results.

Because of the ability to select and compare any possible combination of variables, Trial Analysis Tool 170 provides an extremely helpful graphical methodology for mining Results Database 22 for correlations between the variables of primary interest and disease progression measures. This process then supports the data-driven analysis design of clinical trials. For example, the user can explore which combinations of patient variables, such as estrogen depletion, smoking history, and diabetes, result in positive outcomes for the proposed intervention for osteoporosis. Perhaps the proposed intervention is very effective in patients with estrogen depletion who do not smoke and do not have diabetes, but is not different from a placebo for those patients who smoke. Trial Analysis Tool 170 provides a very effective interface for exploring and depicting these relationships. The user can then exploit these patterns in the underlying biologic and clinical data directly in the design of clinical trials.

PHARMACOECONOMIC EXPLORER

Pharmacoeconomic Explorer 16 performs pharmacoeconomic analysis to answer user questions about whether a proposed intervention compares favorably to existing standard practice(s) from a cost-benefit perspective. While Target Discovery Explorer 12 and Clinical Trials Explorer 14 provide great insights for the user about the impact of a proposed intervention on a biology or a patient type, these insights do not directly translate into pharmacoeconomic comparisons of cost, quality of life, or projections of future treatment requirements. Pharmacoeconomic Explorer 16 addresses these questions specifically.

Pharmacoeconomic (PE) Explorer 16 embodies an approach to pharmacoeconomic analysis that can be used during the target development process. The approach uses expert knowledge about what factors are important to consider for the given disease/biological system. This expert knowledge is represented in a set of influence diagrams (see for example FIG. 24) that identify the relevant factors and their relationships to one another. Expert knowledge is also used to define the relative weights of the different factors in the influence diagrams.

Pharmacoeconomic analysis, according to the present invention, involves three separate analyses of the merit of the proposed intervention: patient outcome; practitioner outcome and acceptance; and outcome for the payer, i.e., the insurance provider. These analyses are based on the influence diagrams that are constructed from expert knowledge of the factors that influence each group and of the weights for the factors depicted in the influence diagrams. "Outcomes" is intended to mean the comprehensive net result of an analysis of all factors affecting the particular constituent.

The analysis for each group is generally based on standard categories of factors. Patient outcomes depend on costs to the patient, the quality of life of the patient as a result of the intervention, and the overall effect of the intervention on disease progression. Quality of life is an intangible entity that must be defined for each disease area. Other factors affecting the patient may additionally or alternatively be included. Practitioner outcomes depend on the profitability of the proposed intervention for the practice, as well as the clinical outcomes associated with the intervention and the resulting patient satisfaction. Finally, the payer outcomes depend primarily on cost savings to the company. Cost savings are determined by the effect of the proposed intervention on disease progression and the cost of the proposed intervention relative to the standard approaches, including the relative costs of future intervention requirements. Positive intervention effects may yield reduced future intervention requirements, which may contain the cost. Table 4 lists the general factors used in each analysis. This list exemplifies the types of factors considered and is not intended to be comprehensive. The factors considered depend substantially on the disease itself.

TABLE 4

Factors Affecting the Three Outcome Analyses

| Analysis | Factors Affecting the Analysis |
|---|---|
| Patient Outcome | 1) Intervention effect - the impact of the intervention on the disease progression measures<br>2) Cost to the patient - cost of the intervention and estimated cost of future interventions; these are modified by the type of insurance carried by the patient, the type of practice visited, the area of the country in which the service is provided, and the patient's level of compliance with the prescribed intervention regimen<br>3) Quality of life - intervention side effects, lifestyle and self image, required time and effort, the patient's employment status, and others, depending on the disease itself |
| Practitioner Outcome | 1) Profitability - cost to the doctor (e.g., time required to deliver the intervention, price of the materials, etc.), the type of practice, the mix of insurance types carried by patients in the practice, and the practice volume<br>2) Clinical outcomes - good disease progression results keep patients satisfied and in the practice, but out of the office |
| Payer Outcome | 1) Cost savings to the company - on the cost of the intervention and the estimated cost of future interventions, which depends on the effect of the intervention on disease progression |

For example, in osteoporosis, patient outcome is calculated based on the cost of the intervention and quality of life issues that address the side effects of the intervention, such as risk of breast cancer, and the patient's self-image and lifestyle issues, such as reduced risk of fracture and whether the intervention is taken in pill or injectable form. In osteoporosis, high quality of life is associated with few side effects and reduced fracture risk, resulting in enhanced mobility and self-sufficiency. In addition, the value of the side effects of the intervention is based on the regimen in which the medication is delivered (e.g., is it pill form or injection; is it delivered daily or weekly), the risk of breast cancer of the patient, and the urgency with which the treatment is needed.

Once the structure of the influence diagrams, i.e., the factors and their relationships, is defined, weights can be assigned. Weights are determined based on issues such as the relative impact of the factors included in the diagrams and any interactions between them. The impact of each of the factors in the diagram is modified by patient attributes. Expert knowledge determines how each of the factors should be weighted based on the presence or absence of certain patient attributes. For example, patients who have nonexempt employment status are more likely to be concerned about time away from their job than patients with exempt employment status. And in the osteoporosis example, urgent treatment outweighs the side effects associated with receiving an injection. However, if treatment is not urgent, the delivery method is more influential in the overall patient outcome.

Once all aspects of the influence diagrams have been defined, the factors, their relationships, and the relative weights are translated into equations and coded into software to automate the calculation of the various outcomes. The translation into software code involves defining a representation of the relationships, their weights, and the calculations of the outcomes. This can be accomplished through a number of standard data structures and processes, such as conditional branching and case statements.

Figure 19:
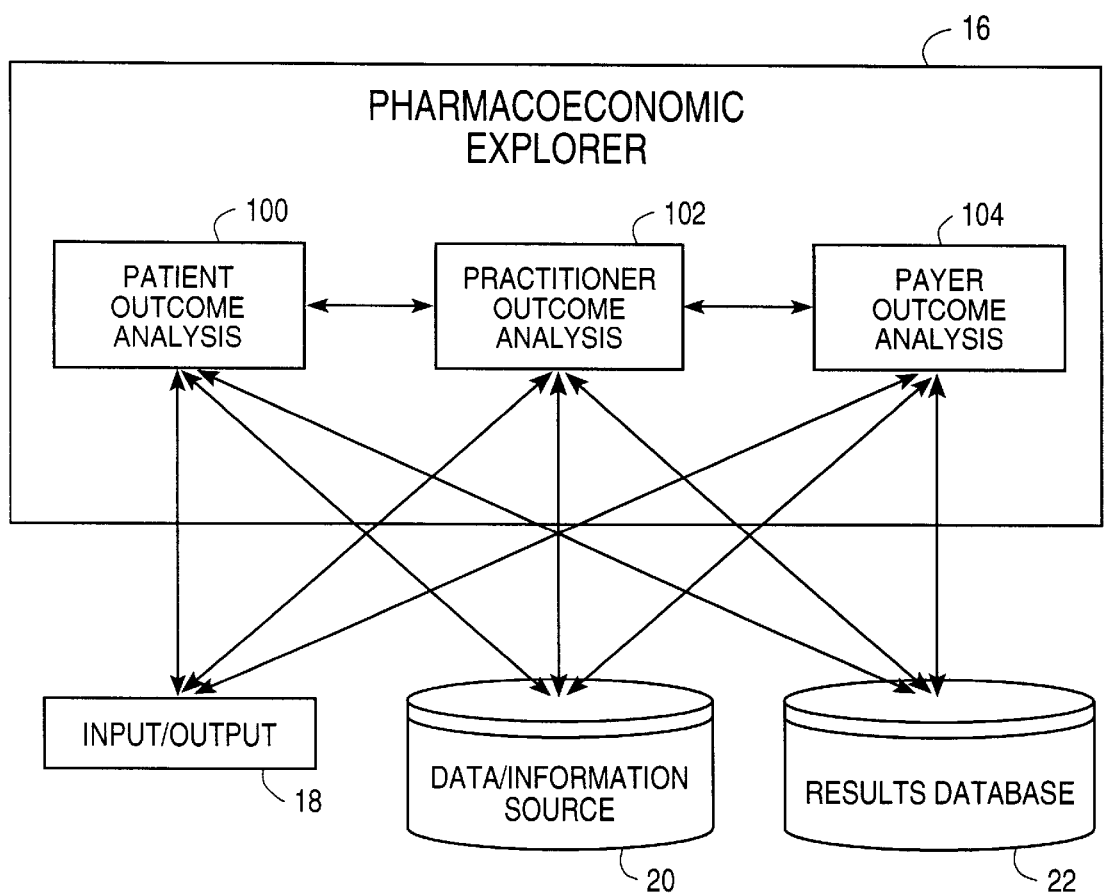
FIG. 19 is a block diagram of the components of the Pharmacoeconomic Explorer.

FIG. 19 is a block diagram of the components of Pharmacoeconomic (PE) Explorer 16. PE Explorer 16 estimates patient, practitioner, and payer outcomes for the proposed intervention and compares these outcomes to the outcomes associated with standard interventions. That is, all three outcomes are calculated twice, once for the proposed intervention and once for at least one standard practice, to yield a comparison. To this end, PE Explorer 16 is composed of three modules: Patient Outcome Analysis 100, Practitioner Outcome Analysis 102, and Payer Outcome Analysis 104. To determine the outcomes, information in addition to the intervention effect on disease progression is collected (via the user and Input/Output 18, Results Database 22 and/or Data/Information Source 20). Each of Patient Outcome Analysis 100, Practitioner Outcome Analysis 102, and Payer Outcome Analysis 104 is a combined Query Processor 226 and Results Synthesizer 228. That is, each of the three main components of PE Explorer 16 generates queries of the appropriate data source and analyzes the returned data.

Patient Outcome Analysis

Figure 20A:
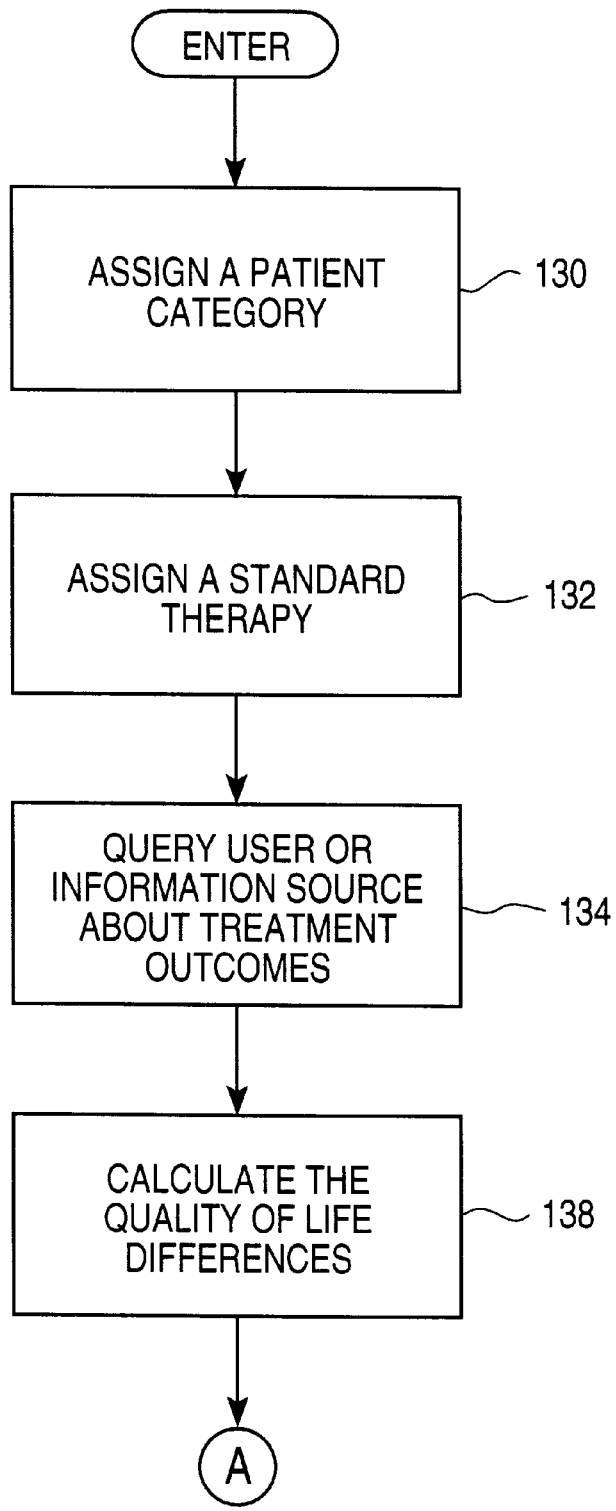
FIG. 20a and FIG. 20b together form a flow chart of the process of producing a pharmacoeconomic analysis.
Figure 20B:
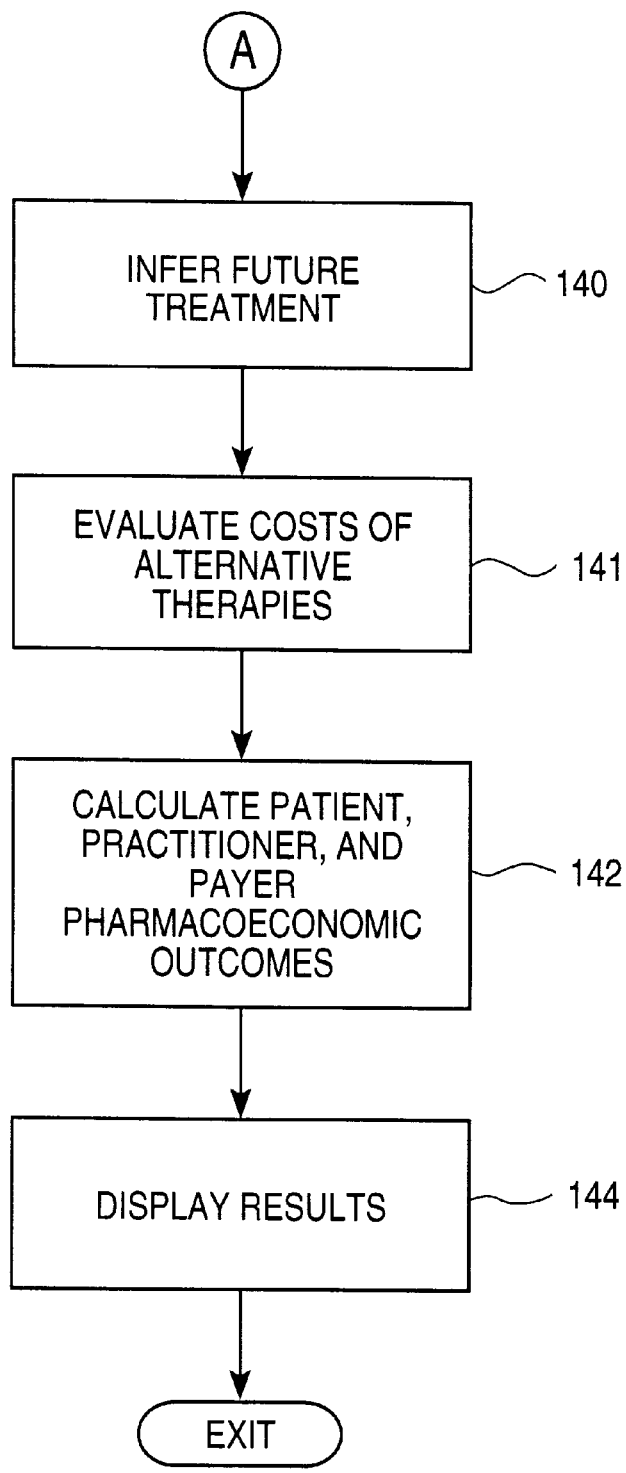

FIG. 20a and FIG. 20b together form a flow chart of the overall processing performed by PE Explorer 16. Calculating outcomes for the different constituents starts with an assessment of the patient's outcome by Patient Outcome Analysis 100. The process of calculating the patient outcome proceeds in sequential steps. PE Explorer 16 collects data in order to calculate the various outcomes. Each step in the flow chart, until step 142, involves collecting or creating data that are used in the calculations in step 142. The calculations in step 142 utilize the software code implementing the influence diagrams to produce outcome evaluations for all three groups. The results are displayed in step 144.

In order to calculate patient outcome, Patient Outcome Analysis 100 first ascertains what the standard intervention is for a patient for comparison against the proposed intervention. To do this, the patient is assigned 130 a disease category based on the presenting signs and symptoms. Patient Outcome Analysis 100 uses expert knowledge of what the disease categories are and what signs and symptoms lead to the placement in each category. This categorization depends on expert knowledge about how patients in the different disease categories are generally treated. For example, the severity of the disease in part determines how aggressively the practitioner will intervene in the disease process. The signs and symptoms for the given patient are provided by the user or retrieved from Data/Information Source 20, and Patient Outcome Analysis 100 determines 132 the patient's disease category. Based on this categorization, Patient Outcome Analysis 100 then determines what a standard intervention is for that patient.

Patient Outcome Analysis 100 then queries 134 Data/Information Source 20 to retrieve the disease progression for the patient over a given time period using a standard intervention and using the proposed intervention. This information determines the patient's status in terms of changes in the signs and symptoms as a result of exposure to the standard intervention and to the proposed intervention. This allows the further assessment of which intervention is likely to provide the fewest side effects, least time and effort on the part of the patient, the best overall outcome, and other factors as represented in the influence diagrams. These factors combine to yield a quality of life calculation for the patient 138 for the alternative interventions.

The amount of disease progression over the given time period under each intervention is also used to estimate 140 the future interventions that the patient would require in the future (i.e., beyond the selected time period). In general, better disease progression from an intervention yields reduced future intervention, which leads to reduced signs and symptoms of the disease, reduced costs and inconvenience, and increased quality of life. Estimating future intervention requirements involves knowledge of how each current intervention alters disease progression in a given patient. This information may be stored in the Data/Information Source 20 or may be available in Results Database 22, depending on the overall configuration and implementation of the system. The estimates may be based on the disease categorization or additional expert information. For example, if the disease progression for a patient results in a movement between disease categories, then the patient also has a change in the level of intervention needed in the future. Such information and data are then used to develop an estimate of the future intervention requirements for a patient. As mentioned, this information also supports the quality of life calculation.

The costs of the current intervention and future intervention requirements for both the standard intervention and the proposed intervention can be calculated and compared based both on the actual cost of the alternative interventions and on the estimated future intervention needed under both the standard intervention and the proposed intervention. Relative costs of interventions are thus compared 141 both in terms of costs accrued during the analysis period and costs of the predicted future intervention requirements for the patient. To compare costs of the alternative interventions, cost data is obtained by directly coding the costs in the system and/or by querying for cost information stored in Data/Information Source 20. The overall cost of intervention is then calculated for both the standard intervention and the proposed intervention over a specified period of time (e.g., six months, two years, twenty years, and so forth) and for the estimated future intervention needed by the patient.

The actual cost to the patient of the alternative interventions depends not only on the market price of the intervention (which may depend on the type of practice the patient is in and the area of the country in which the patient resides), but also on a patient's insurance coverage. The cost computation performed by Patient Outcome Analysis 100 reflects generalities about different types of insurance coverage and the average cost of the different types of procedures. The difference between the patient's direct cost for a proposed intervention and the standard intervention is determined by computing the patient's direct cost for each alternative and subtracting. The cost for an intervention may be calculated based on three variables: the regimen, the patient's level of compliance, and the percentage of the cost likely to be covered by the patient's insurance. For example, suppose a proposed intervention costs approximately $1 per day. These costs are added for the number of days of treatment specified by the user as part of the regimen. This is multiplied by the patient's level of compliance, a percentage from 0 to 1 (or a time dependent function), and then by the percentage of the cost not covered by the patient's insurance program to arrive at the patient's direct cost for the proposed intervention.

Figure 24:
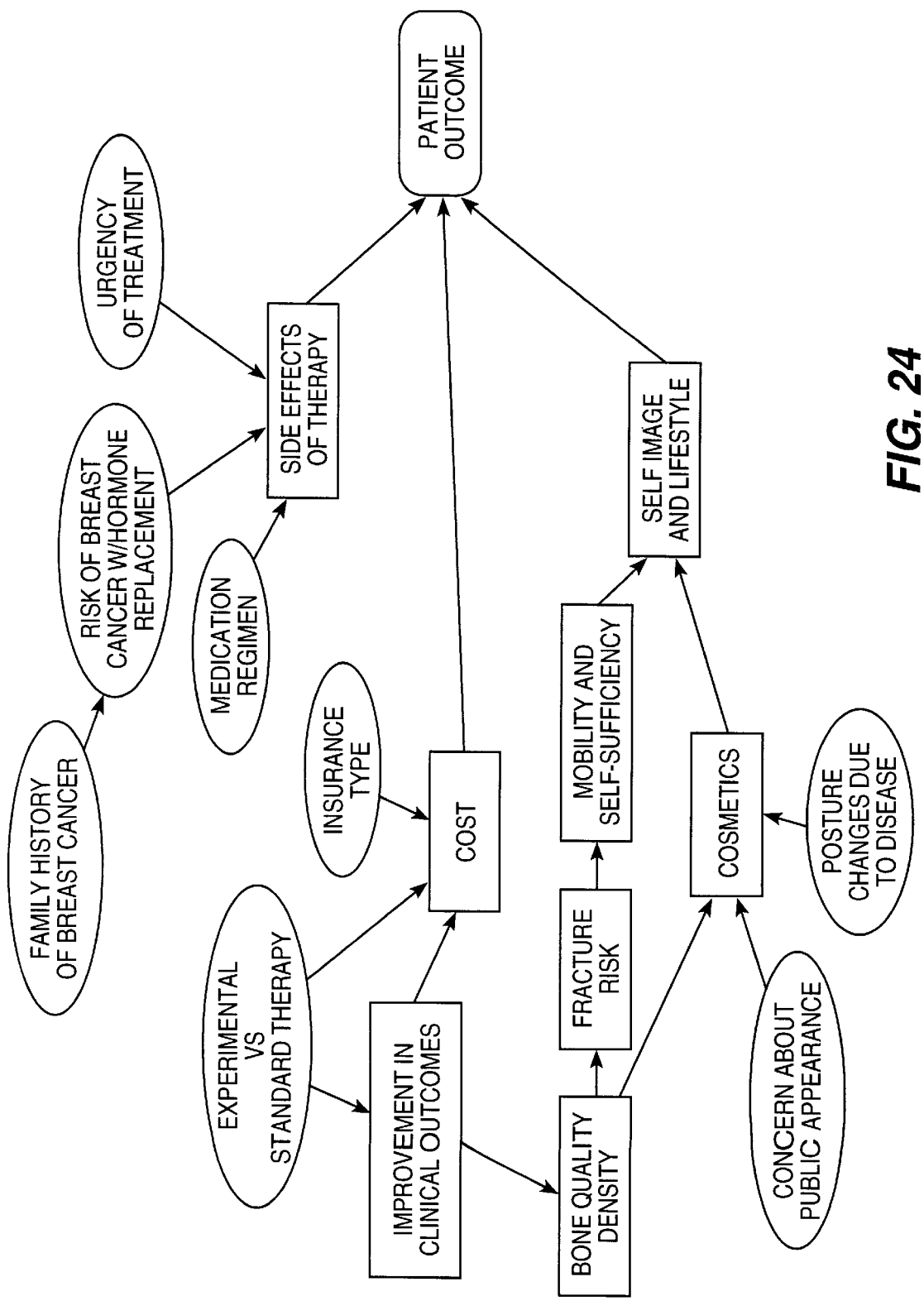
FIG. 24 shows examples of an influence diagram used to analyze information the patient outcome.
Figure 25A:
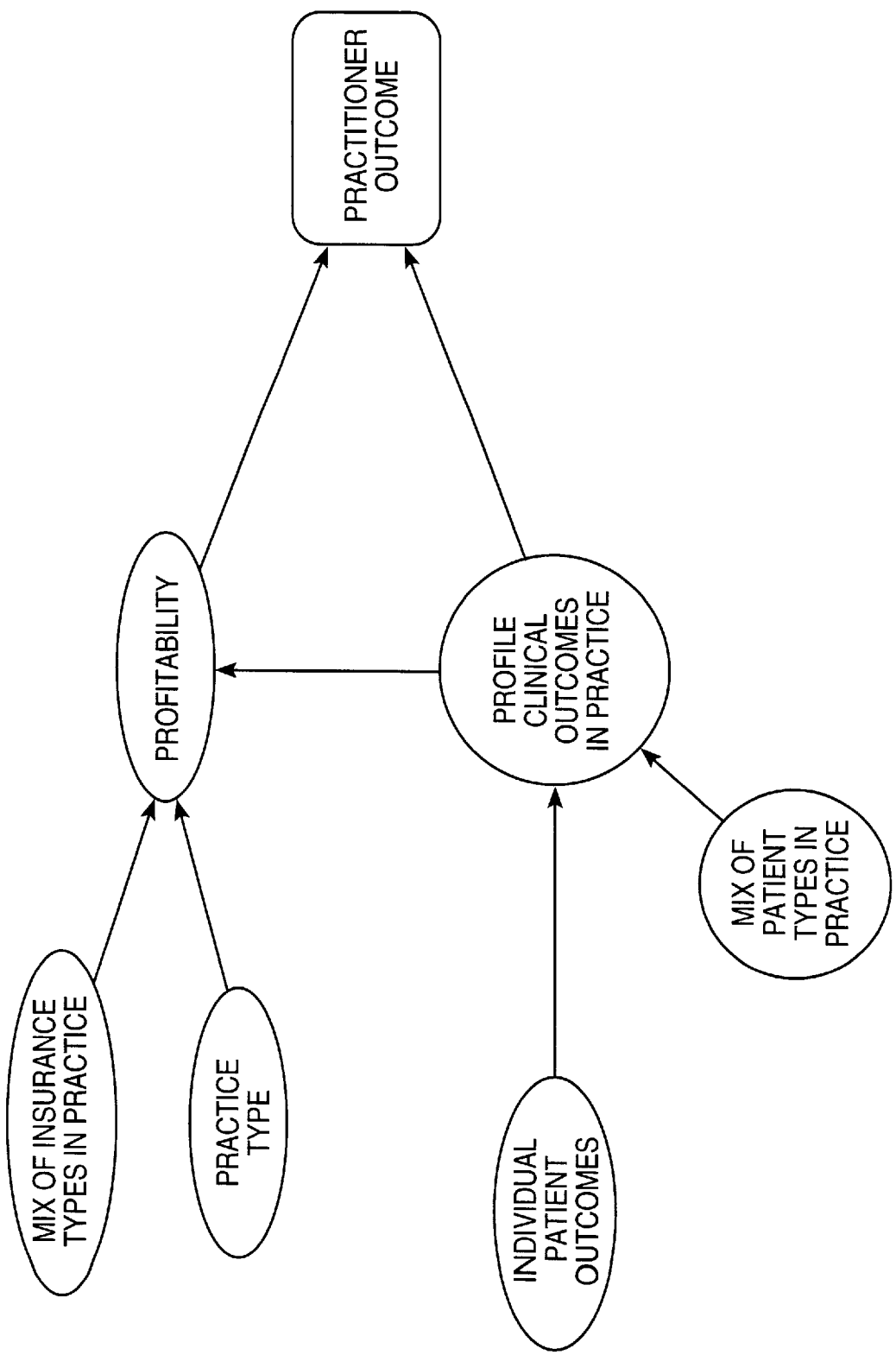
FIG. 25a is an example of an influence diagram used to analyze information the practitioner outcome.
Figure 25B:
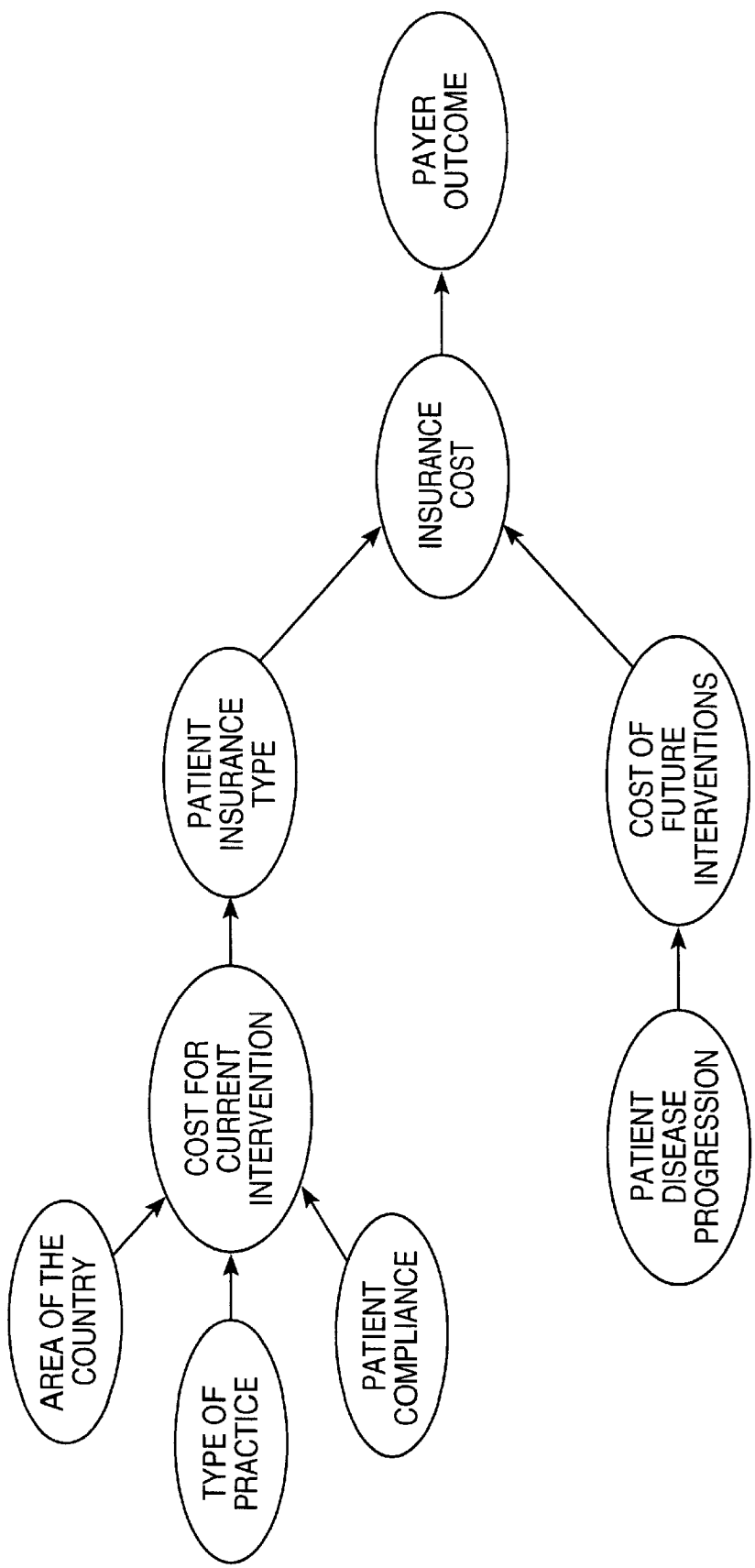
FIG. 25b is an example of an influence diagram used to analyze information the payer outcome.

Patient Outcome Analysis 100 then calculates 142 the patient outcome, practitioner outcome, and payer outcome based on the corresponding influence diagram and the equations created from the factors, relationships and weights as coded into software. FIG. 24, FIG. 25*a*, and FIG. 25*b* are examples of influence diagrams used in analyzing information from Data/Information Source 20 for the osteoporosis example. Patient outcomes are based on a weighted combination of the cost analysis and quality of life variables. Calculating practitioner outcomes depends on patient outcomes, practice volume, and primary insurance coverage of patients in the practice. Finally, payer outcomes depend on the cost of the interventions and the projected future intervention. The general rule is that averted or delayed costs benefit the payer.

Practitioner Outcome Analysis

Once Patient Outcome Analysis 100 has evaluated the patient outcomes, this information is provided to Practitioner Outcome Analysis 102, which determines 142 practitioner outcomes, and to Payer Outcome Analysis 104, which determines 142 payer outcomes. Practitioner Outcome Analysis 102 uses data pertaining to a variety of practitioner attributes, such as the size and type of practice, in addition to the patient outcome. This information may be obtained directly from the user or by querying Data/Information Source 20. The factors and relationships that combine to yield an assessment of the practitioner outcome are represented in the corresponding influence diagram. For example, FIG. 25*a* shows the influence diagram for practitioner outcomes for osteoporosis. In this case, large practices benefit by retaining patients (that is, supplying good patient outcomes) while keeping patients out of the office for treatment time that could be offered to other patients. Calculating practitioner outcomes depends on patient outcomes, practice volume, and primary insurance coverage of patients in the practice.

Payer Outcome Analysis

Finally, Payer Outcome Analysis 104 determines payer outcomes in terms of whether or not the experimental intervention reduces the costs relative to current standard practice(s). Again, this calculation is based on the factors and relationships depicted in the corresponding influence diagram as well as the weights of those factors. FIG. 25*b* shows an example influence diagram that guides the payer outcome calculations in the osteoporosis example. Payer outcomes depend on the cost of the interventions and the projected future intervention. The general rule is that averted or delayed costs benefit the payer. Once the analysis is completed for the patient, practitioner, and payer, PE Explorer 16 displays 144 the results of each analysis to the user.

FIG. 21 provides an example of a user input interface for PE Explorer 16 in support of pharmacoeconomic analysis for the patient and practitioner. In general, this interface is designed to accept input parameters 211 related to certain types of practices and patients within the practice as well as a variety of attributes 213 of the patient, and insurance coverage 217. As shown in the example interface of FIG. 21, the user enters information about the patient and practitioner into the interface. The content of this screen could alternatively be supplied in whole or in part from Data/Information Source 20. In the example shown, the data/information is supplied entirely by the user.

Figure 22:
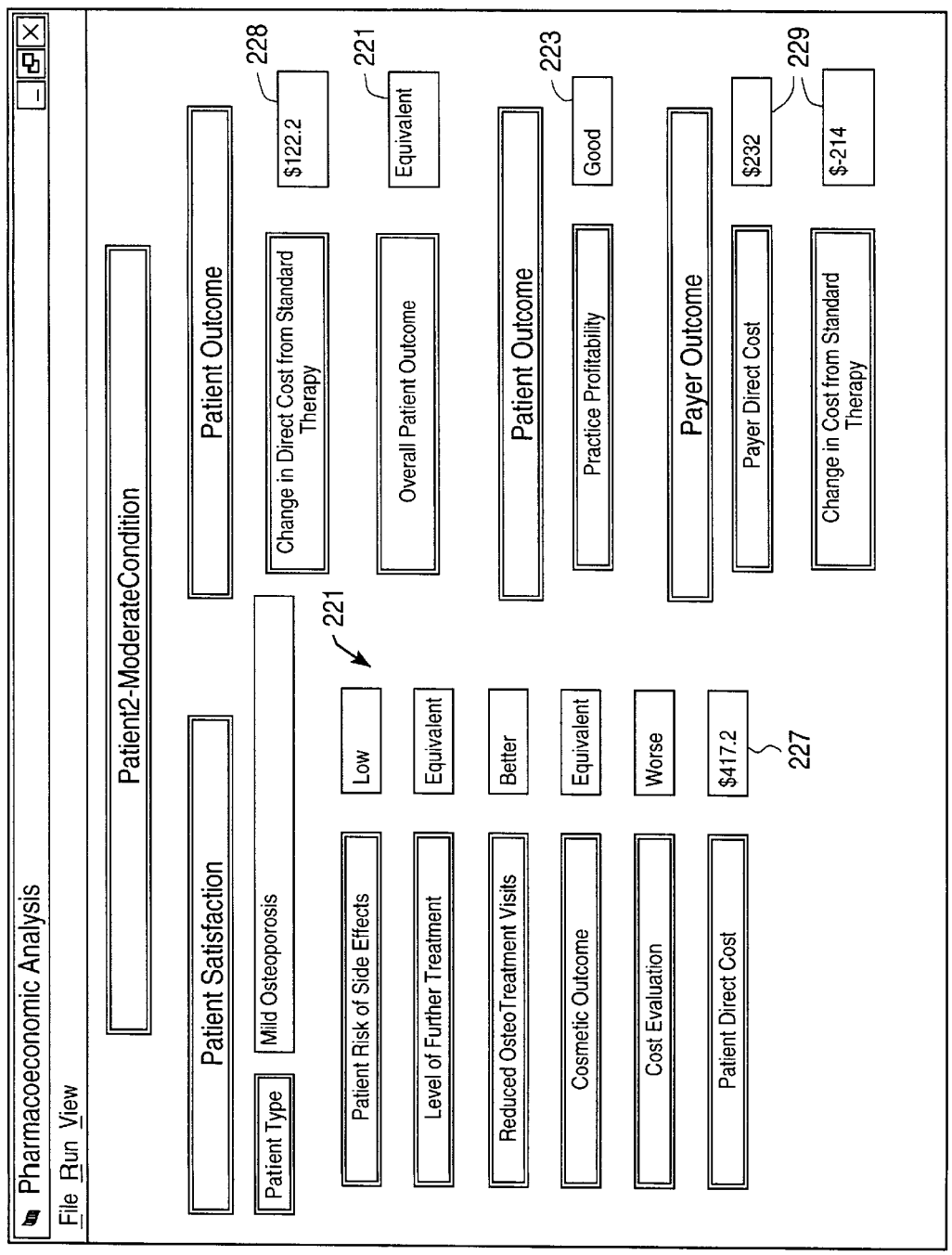
FIG. 22 is an example of the user interface generated by the Pharmacoeconomic Explorer and showing a summary of the pharmacoeconomic analysis for the patient, practitioner, and payer in a report format.

FIG. 22 provides an example of a results interface generated by PE Explorer 16 for pharmacoeconomic analysis for the patient, practitioner, and payer. As shown in the example interface of FIG. 22, patient and practitioner outcomes 221, 223, 229 are displayed in a tabular form using relative evaluations of the differences in outcomes between the proposed and the standard interventions, in either qualitative or quantitative format.

The results of the pharmacoeconomic analysis can additionally or alternatively be displayed as a graphical representation of the influence diagrams that guide the analyses and the associated levels for each of the pharmacoeconomic variables. For example, the influence diagrams upon which the calculations are based can be displayed and color coded to show the relative outcomes for the proposed versus standard intervention. In this manner, the user is able to see graduated differences between the alternative interventions in addition to a final summary of the analysis. In this example of FIG. 22, the patient outcome was equivalent between the standard and proposed interventions. The practitioner and the payer outcomes were both better for the proposed intervention.

Figure 23:
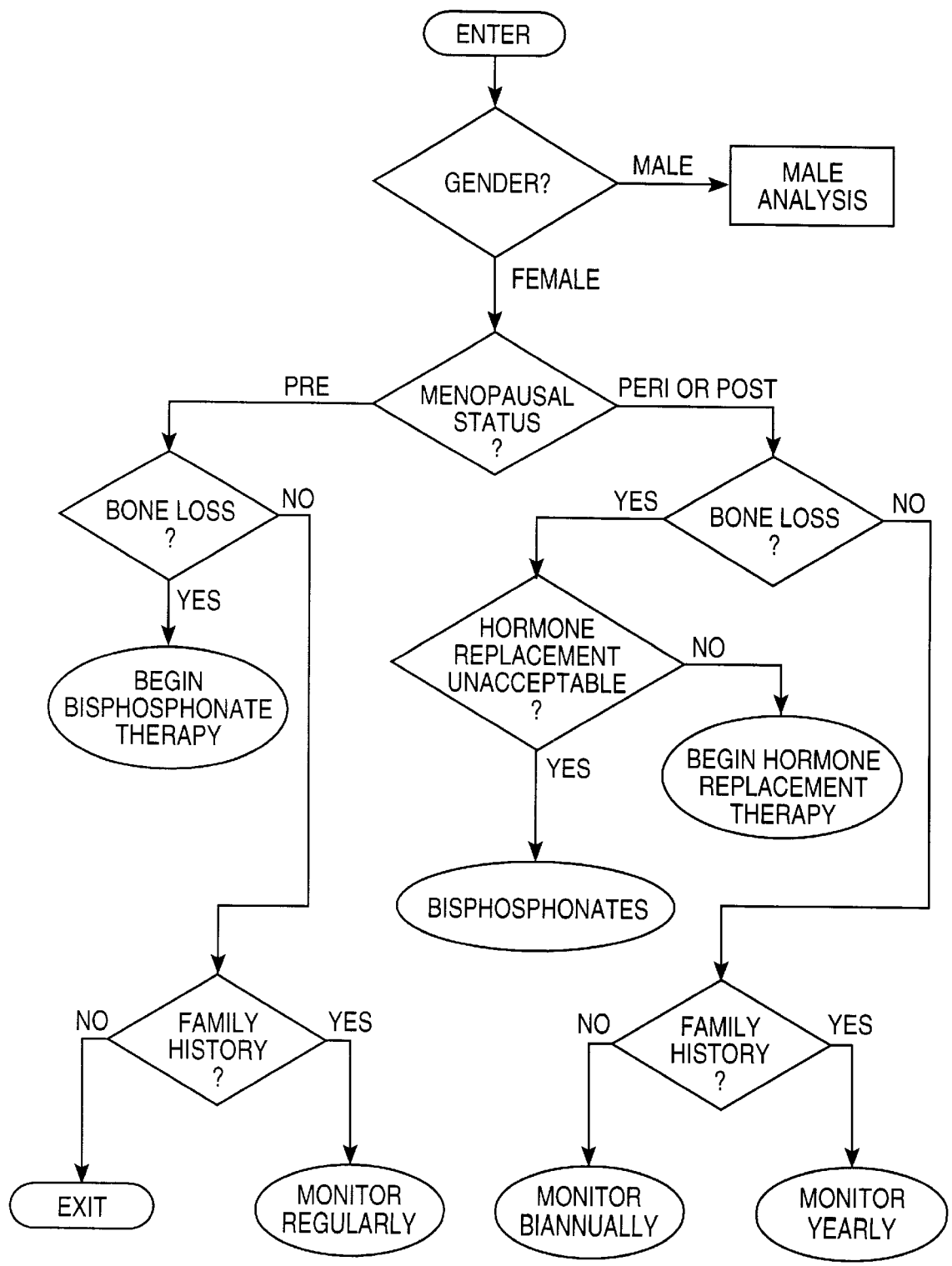
FIG. 23 is a flow chart showing a sequence of analyses designed to determine a categorical designation based on the patient's presenting symptoms and history in order to determine what the standard treatment regimen is for the specified patient.

An example from osteoporosis therapy is illustrative of PE Explorer 16 analysis. In order to determine what the standard intervention regimen is for a patient, the patient is assigned a category designation relative to osteoporosis based on the patient attributes, as shown in FIG. 23. The categorization was developed from experts in the field of osteoporosis. It categorizes patients based on their menopausal status, bone mineral density loss, and treatment history. For example, the information provided about the patient might indicate that she is recently menopausal, has a bone mineral density of 0.8, and has no breast cancer history. This patient would be categorized as a potential candidate for estrogen replacement to reduce future bone mineral density loss.

The standard intervention for this patient would be determined based on whether estrogen replacement is contraindicated. FIG. 23 is a decision tree outlining standard interventions for each of the patient types in the osteoporosis example. The standard intervention for this patient would be estrogen replacement therapy. This intervention is then used in Patient Outcome Analysis 100 to compare the proposed intervention to the standard intervention in terms of both the expected patient disease status, as well as comparative costs and quality of life between the proposed intervention and the standard.

Table 5 shows example costs for standard interventions for osteoporosis. The standard intervention for an asymptomatic woman, i.e., a woman with bone mineral density within the normal range, who does not want to have estrogen replacement therapy would include, for example, X-ray monitoring from a specialist for a total for $400 per year. The standard intervention for a woman for whom estrogen replacement is appropriate is just $180 per year.

TABLE 5

Costs of Standard Osteoporosis Interventions

| Monitoring or Therapy | Primary Practitioner | Specialist |
| --- | --- | --- |
| X-ray monitoring | $200 | $400 |
| Sonic monitoring | $80 | $150 |
| Hormone replacement | $15/mo | $15/mo |
| Bisphosphonates | $50/mo | $50/mo |

In the osteoporosis example, the actual cost for a procedure depends not only on the average cost of the procedure but also on the type of practice in which the procedure is provided. In this example, treatment costs depend on whether the practitioner is a primary practitioner or a specialist, which in turn may depend on the severity of the patient's condition as well as the type of insurance the patient has.

There are many types of insurance plans, each providing varying degrees of coverage. Types of insurance plans include Indemnity Plans, Managed Care Plans, and Capitated Plans. The following are tables of example cost categorizations for osteoporosis and insurance coverage. Table 6 describes the major categories of insurance related to the type of intervention. Each of the principle types of insurance coverage dictates how much the patient pays for each type of intervention and how much the insurer pays.

TABLE 6

Insurance Coverage for Intervention Type in the Osteoporosis Example

| | |
| --- | --- |
| Monitoring | Indemnity Insurance: generally not covered unless the condition is detected, then is covered at the patient's percentage coverage rate.<br>Managed Care: may be covered as prevention; if not will be covered when condition is detected at the patient's co-payment rate. |
| Therapy | Generally covered by all insurance programs either under the patient's prescription program or at co-payment rate. |

The analysis for osteoporosis develops patient costs by calculating variables associated with compliance, the level of insurance coverage, the costs of intervention, and the estimated costs of future interventions. Cost to the payer uses similar types of insurance related data.

In summary, PE Explorer 16 collects input variables for the patient and practitioner, queries the Data/Information Source 20 and Results Database 22, and analyzes the information obtained to evaluate the clinical effectiveness of the proposed intervention for a given patient, practitioner and payer scenario.

DISEASE PROGRESSION EXPLORER

Once a potential intervention has been discovered, submitted to clinical trials, and its pharmacoeconomic value established, the remaining task is to bring the new intervention to the appropriate practitioners and patients. Traditionally, this process involves producing brochures and pamphlets to describe the intervention, the delivery regimen, and the indications and contraindications for its use with patients. It also involves educating the sales force about the intervention and how it affects the underlying disease process so that they can educate practitioners. Seldom is there a major attempt to design educational aids for patients. Nor is there currently available the ability to project disease progressions for individual patients in accordance with their particular attributes, such as history and risk factors. Disease Progression Explorer 17 augments traditional approaches to educating practitioners and the sales force, and it has the beneficial feature of directly including patient education and decision-making support as one of its functions.

Practitioners and patients need to be able to visualize how patient attributes, such as specific risk factors, and the use of alternative interventions are likely to affect the course of disease progression over time and the subsequent decisions concerning disease management. Many also wish to understand how these effects emerge from the underlying biology of the disease. Disease Progression Explorer 17 meets these needs by graphically displaying disease progression for particular patient attributes and time periods from data and information synthesized by the other components of Integrated Disease Information System 10, or from outside sources, and included in either Results Database 22 or Data/Information Source 20. With this tool, practitioners, patients, and the marketing/sales teams better understand the research that has developed the intervention and better understand the effect of the intervention on the disease progression in individual patients over time.

Figure 26:
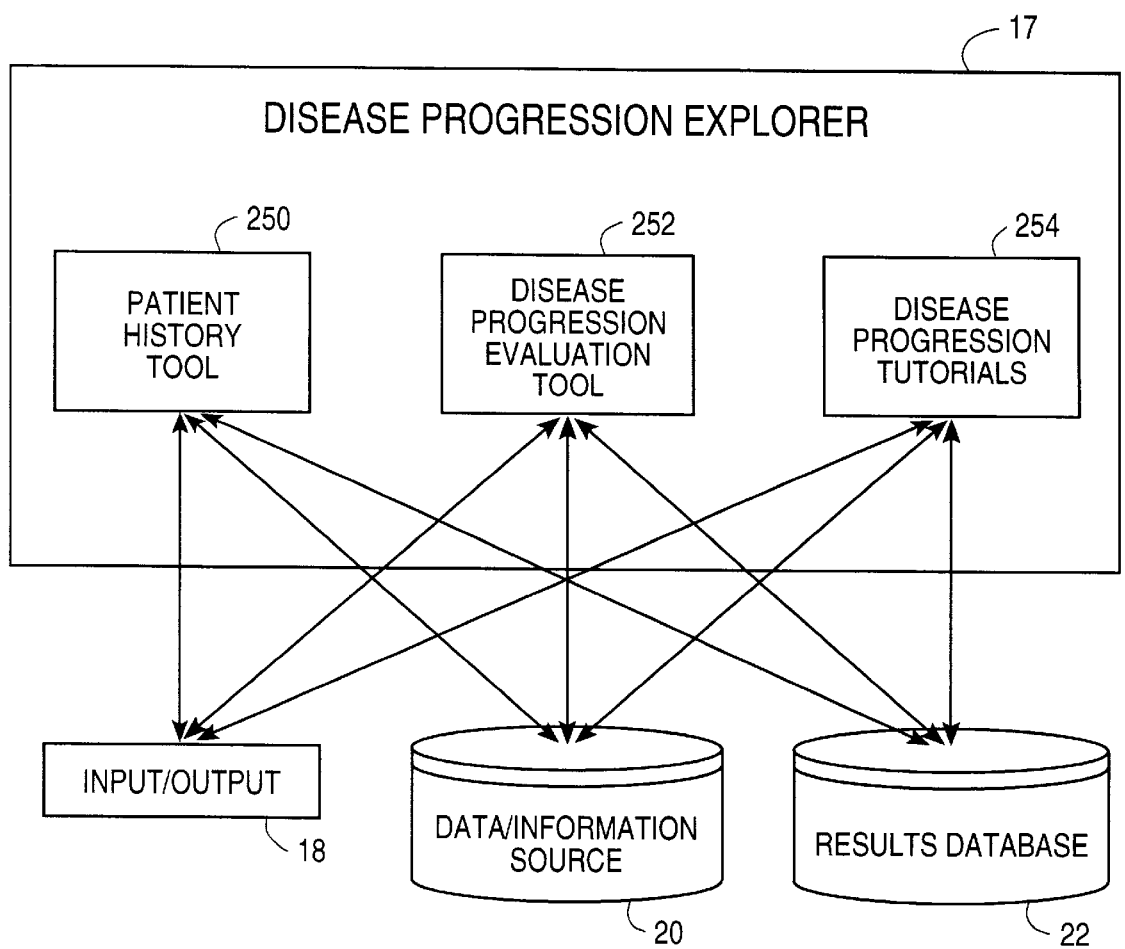
FIG. 26 is a block diagram of the components of the Disease Progression Explorer.

FIG. 26 is a block diagram showing the components of Disease Progression Explorer 17. Disease Progression Explorer 17 comprises three components that enable practitioners and patients to understand and explore projected disease progression over time under various patient risk profiles and/or intervention conditions. This Explorer also has embedded disease progression tutorials explaining both the disease progression itself, and how the disease progression is estimated in order to educate the practitioner and patient on the underlying biology of the disease process and other factors of relevance to the patient and practitioner. Thus, Disease Progression Explorer 17 serves as a marketing/sales aid for a pharmaceutical/medical device company and/or as an educational/decision aid for the practitioner and patient.

Disease Progression Explorer 17 comprises Patient History Tool 250, Disease Progression Evaluation Tool 252, and Disease Progression Tutorials 254. As shown in FIG. 26, Patient History Tool 250, Disease Progression Evaluation Tool 252, and Disease Progression Tutorials 254 interact with Input/Output 18, Data/Information Source 20, and Results Database 22. It should be noted that while FIG. 26 shows the components of Disease Progression Explorer 17 interacting only with Input/Output 18, Data/Information Source 20, and Results Database 22, Disease Progression Explorer 17 could also be embodied in a system such as that shown in FIG. 2 without departing from the spirit of the present invention.

Patient History Tool

Patient History Tool 250 allows a user to specify a patient name and retrieve the patient's attributes from the Results Database 22 or to specify a unique set of patient attributes and query Data/Information Source 20. Patient History Tool 250 is an instance of a Query Processor 226. Results originally generated by the Target Discovery Explorer 12 or Clinical Trials Explorer 14 are retrieved for previously specified patients. Results for new patients are obtained by querying Data/Information Source 20 and synthesizing the information retrieved.

Figure 27:
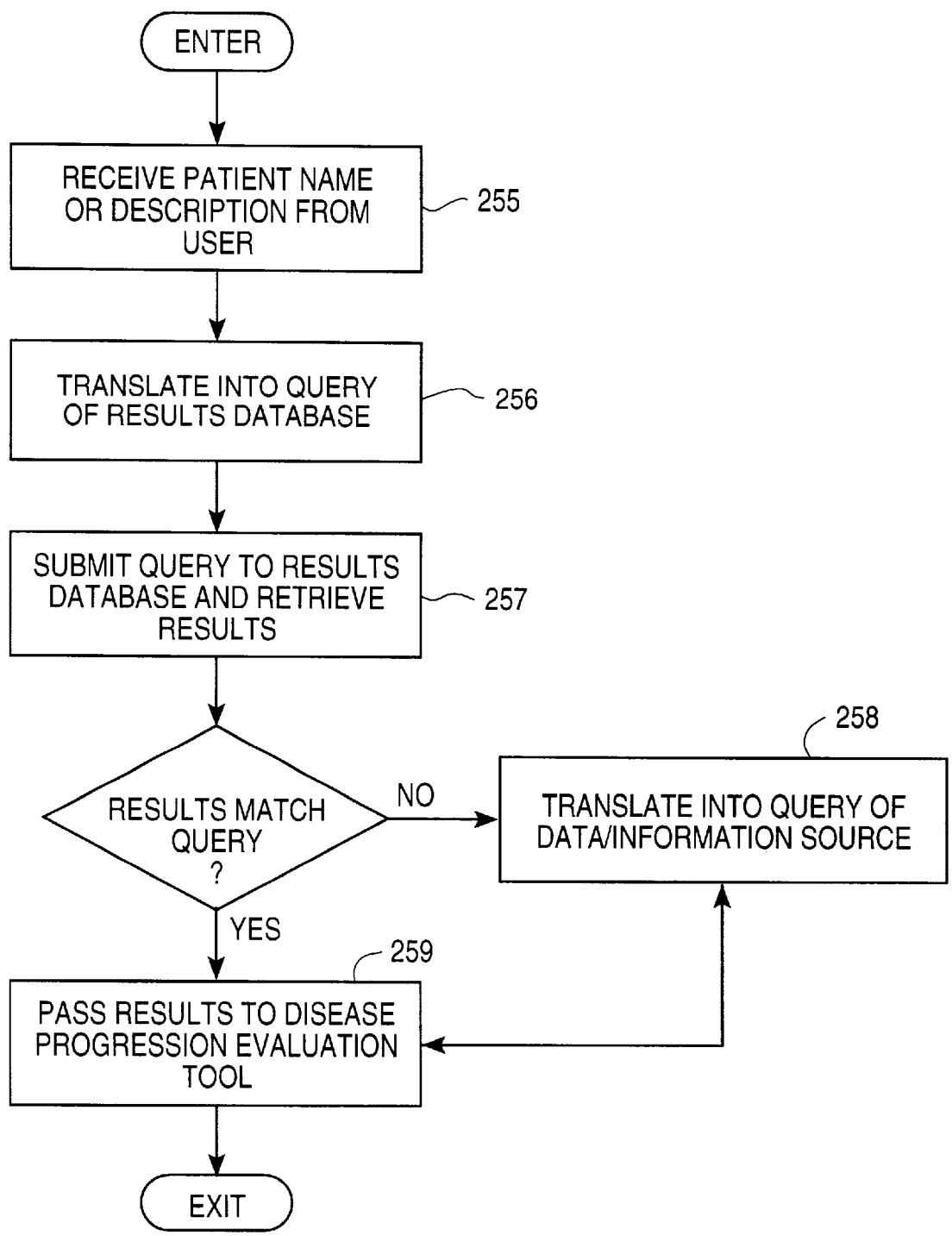
FIG. 27 is a flow chart of the processing of the Patient History Tool.

FIG. 27 shows a flow chart of the processing performed by Patient History Tool 250. The user enters 255 a patient name or patient description, including specific attributes, into the tool along with any interventions of interest. This entry is translated 256 into a query of the Results Database 22. The query is submitted 257 to Results Database 22 and the information is retrieved. The software evaluates the outcome of the query to determine whether the patient's disease progression has been evaluated by the other components of the Integrated Disease Information System 10. If not, Patient History Tool 250 translates 258 the user's input into a query of Data/Information Source 20 to obtain the raw data relevant for the specified patient attributes. The results are passed 259 to Disease Progression Evaluation Tool 252.

Disease Progression Evaluation Tool

Once stored results are retrieved from Results Database 22 and/or Data/Information Source 20, Disease Progression Evaluation Tool 252 infers the progression of the disease for a patient on a set of clinically-relevant disease progression measures over a user-specified period of time. Disease Progression Evaluation Tool 252 is an instance of a Results Synthesizer 228. Disease Progression Evaluation Tool 252 projects the course of the disease from the disease progression measures onto a graphical representation of the clinical parameters, e.g., on an anatomical representation, or in a graphical chart, for easy understanding by practitioners and patients. To make these projections, Disease Progression Evaluation Tool 252, using knowledge provided by experts in the disease area and/or statistical inferencing techniques, synthesizes the data obtained by Patient History Tool 250 onto a projection of the progression of the disease for the given patient across the time period specified by the user. If, for example, Clinical Trials Explorer 14 has evaluated the particular patient for the time period selected by the user, then Patient History Tool 250 retrieves this information and Disease Progression Evaluation Tool 252 maps, or interprets, the disease progression data onto the clinically-relevant representation. If, however, information for the time period selected by the user has not been synthesized or is not available in either of the databases, then Disease Progression Evaluation Tool 252 computes a disease progression based on expert and/or statistical knowledge of how the disease is likely to progress in the given situation, or based on data that is available in Data/Information Source 20 or Results Database 22 that approximates or matches the patient attributes.

Regardless of how the disease progression is determined, either by retrieval or calculation, the disease progression is output on Input/Output 18 in the form of an anatomical representation. To support this mapping, both an appropriate representation and what permutations in the graphics correspond to changes in the major disease progression measures are defined. For example, in osteoporosis, an x-ray type image of bone may convey the clinically significant impact of bone mineral density loss. The image lightens as bone mineral density decreases from the young adult mean. Images, animations, video or other graphical information (including computational routines for dynamically modifying any of these) corresponding to various values of the disease progression measures are created and stored in Data/Source Information 20, along with expert rules that associate various images with different values of the disease progression measures and time periods for disease progression. Different images or video may be used to convey the appropriate information to the practitioner and to the patient because of their different backgrounds and needs. For example, a patient view might be the estimated spinal curvature that results from low bone mineral density rather than an x-ray image. The stored expert knowledge need not be limited to associating disease progression measures with fixed representations; the expert knowledge may also be associated with graphics processing algorithms that, for example, change the shading, coloration, or other attributes of otherwise fixed or animated images, as a function of the computed disease progression measures.

Figure 28:
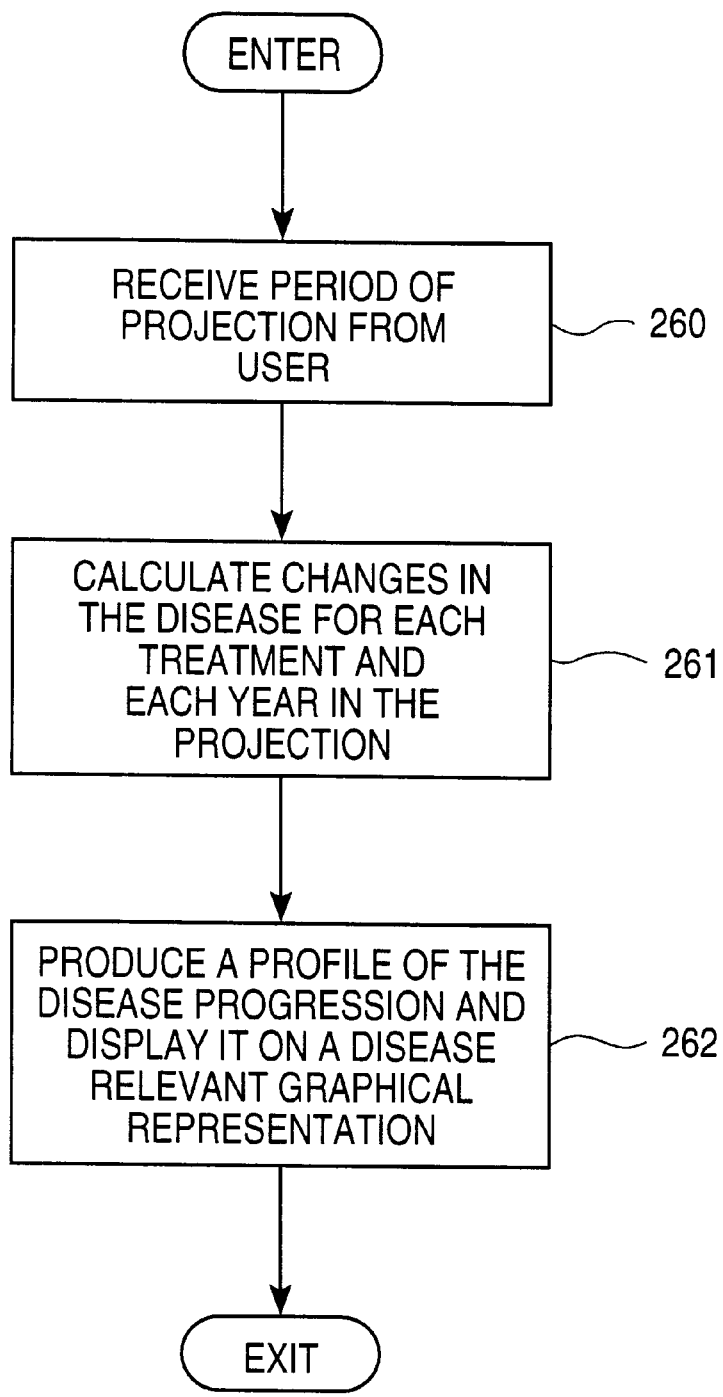
FIG. 28 is a flow chart of the processing of the Disease Progression Evaluation Facility.

FIG. 28 shows a flow chart of the processing performed by Disease Progression Evaluation Tool 252. The user specifies 260 the period over which to project the disease. Disease Progression Evaluation Tool 252 calculates 261 the changes in clinically-relevant disease progression measures based on the data and information received from the Patient History Tool 250 and any additional expert or statistical knowledge available in the software implementation. This information is then used to select 262, using knowledge supplied by experts on the disease, the appropriate graphical representations or graphics transformations representative of the calculated disease progression measures, for example, images of the spinal column configuration in the case of osteoporosis.

Figure 29:
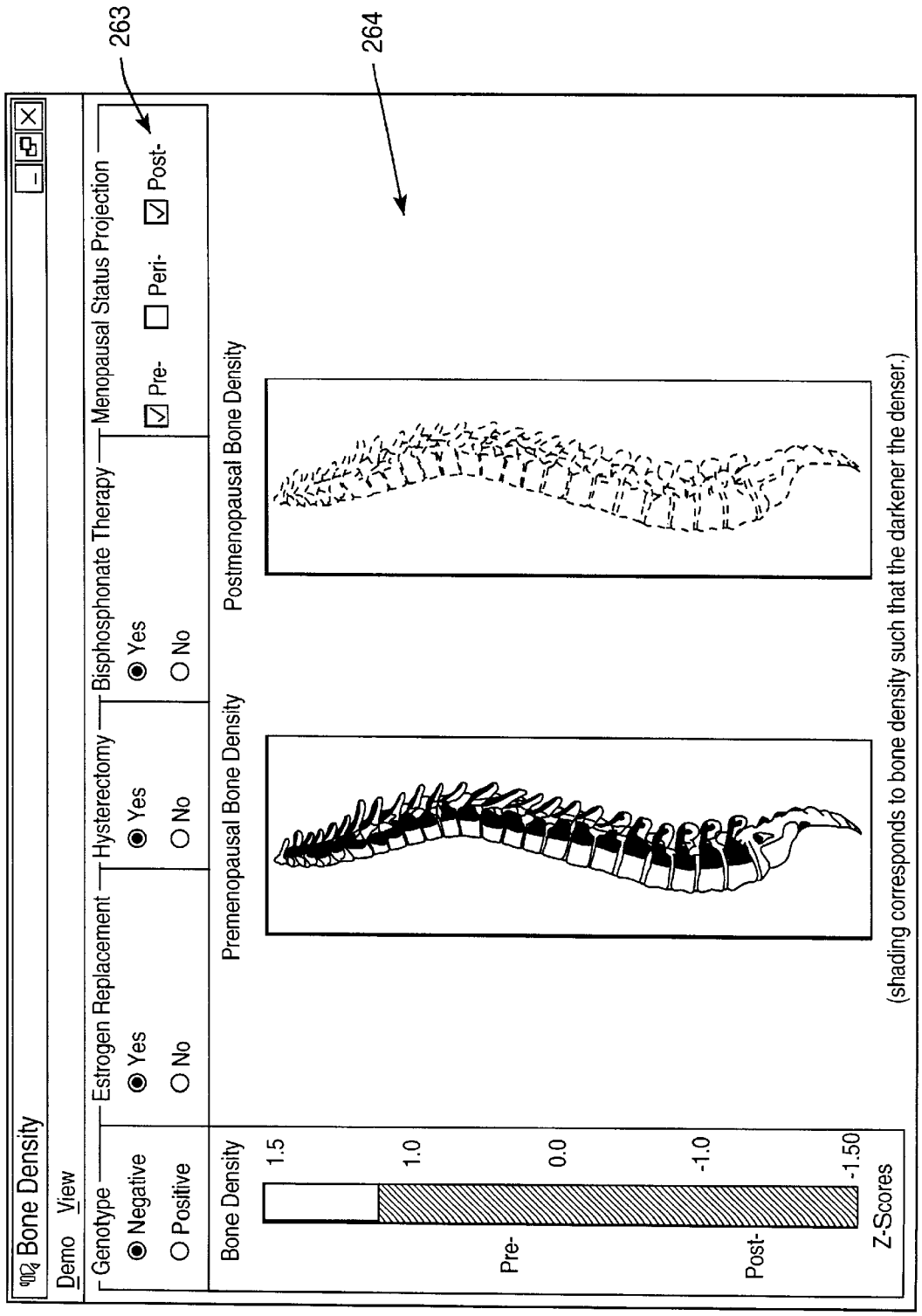
FIG. 29 is a sample user interface to the Patient History Tool and Disease Progression Evaluation Facility.

FIG. 29 shows a sample interface for Patient History Tool 250 and Disease Progression Evaluation Tool 252, as employed in the osteoporosis example. Here a user has specified 263 patient attributes, describing the patient as menopausal by virtue of a hysterectomy and taking estrogen supplements. Patient History Tool 250 formulates and submits a query to the Results Database 22, in the case of a system containing all Explorers, or to the Data/Information Source 20, in the case of a stand alone Disease Progression Explorer 17. This query retrieves information about bone density loss in menopausal women taking estrogen supplements. Disease Progression Evaluation Tool 252 receives this information from Patient History Tool 250 and calculates the average yearly bone density changes for the specified patient. Then, using the expert knowledge, Disease Progression Evaluation Tool 252 projects 264 these changes onto a graphic of an x-ray image of the spinal column for the period of years specified by the user. If the user selects the patient view, Disease Progression Evaluation Tool 252 projects the changes onto graphics of the curvature of the spinal column by computing the likely fracture rate based on expert knowledge.

Disease Progression Tutorials

The final component of the Disease Progression Explorer 17, Disease Progression Tutorials 254, is designed to teach users about the underlying disease biology and how specific patient attributes and/or intervention regimens affect the course of the disease. Disease Progression Tutorials is a combined instance of a Query Processor 226 and Results Synthesizer 228. It combines data and information created by the Target Discovery Explorer 12, the Clinical Trials Explorer 14, and PE Explorer 16, data retrieved from Data/Information Source 20 or Results Database 22, and/or knowledge from experts with lessons and/or explanations. These disease progression tutorials guide practitioners and patients to a greater understanding of the implications of alternative intervention approaches, including the impact of a proposed and any number of standard interventions on the disease biology and progression, the benefits and drawbacks of all competing approaches, the cost of the alternatives, and the impact of the alternative interventions on the patient's quality of life. The user may elect to view one or more of the Disease Progression Tutorials 254 when using Disease Progression Explorer 17.

Figure 30:
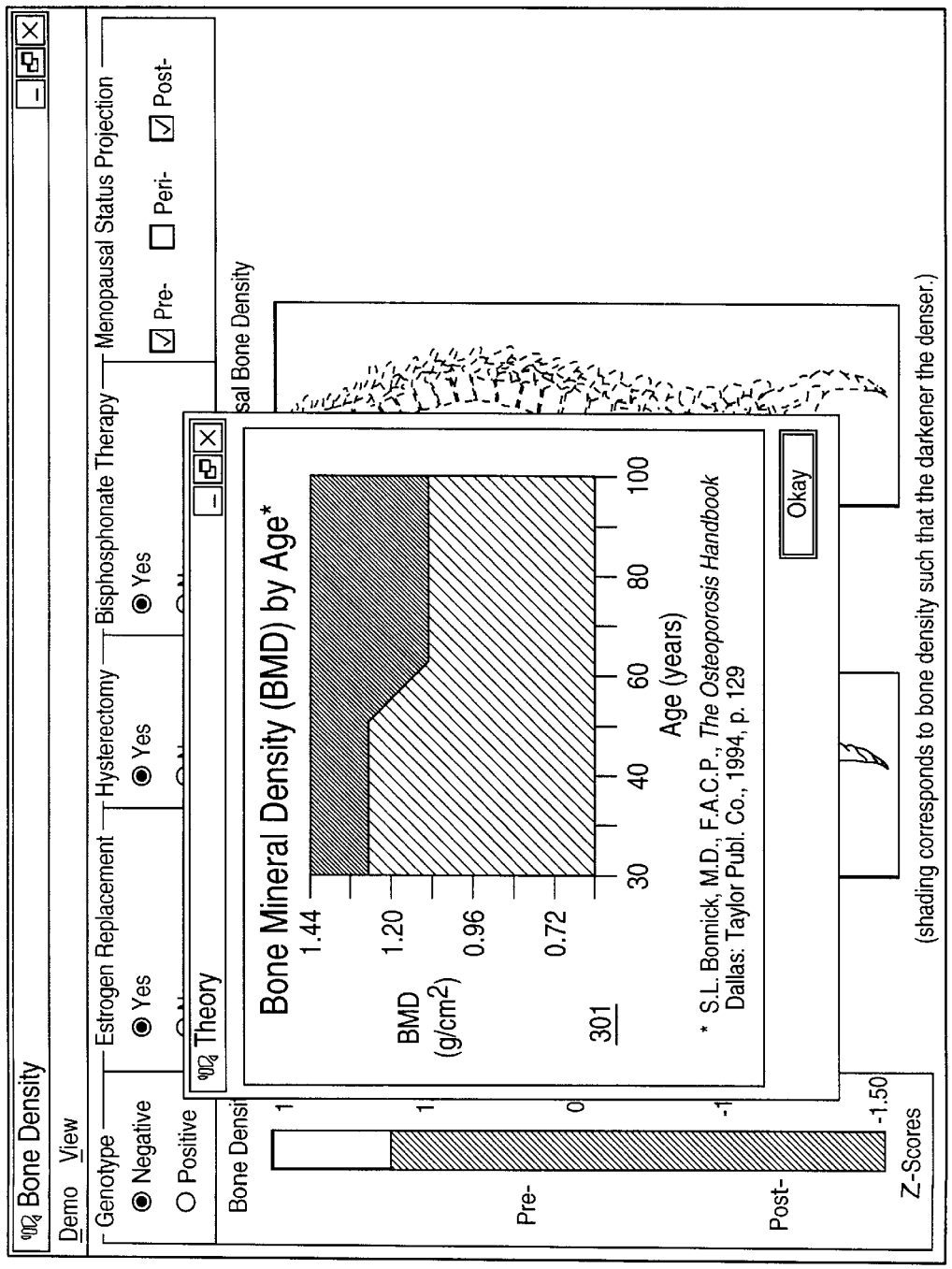
FIG. 30 is a sample user interface to the Disease Progression Tutorials.

The disease progression tutorials are created and coded into the software during software development. First, topics likely to be of interest to patients and practitioners are selected. Then a lesson or tutorial is written about each topic. Software is created to present the lessons and tutorials, for example using conventional multimedia presentation tools. To access a disease progression tutorial, the user selects a topic from the user interface and Disease Progression Tutorials 254 formats and supplies the explanation or tutorial. FIG. 30 shows a sample interface for Disease Progression Tutorials 254, here using a simple chart 301 to display the relationship between bone mineral density and age, in the context of osteoporosis.

The Disease Progression Explorer 17 uses expert knowledge for a number of tasks, including developing an estimated disease progression when no data are available, interpreting data into an estimated disease progression when data are sparse, and converting potentially biologically-based disease progression measures into clinically observable ones (e.g., converting bone mineral density measurements and a variety of other patient factors into a projection of the shape and fracture rate of the spinal column.) The knowledge that is implemented in these analyses comes from experts in the field. To support the disease progression estimates, the experts provide patient attributes that influence disease progression over time and assign weights to those attributes. They also provide data on the rate of progression based on the interaction between patient attributes and intervention regimens. For example, in osteoporosis, estrogen supplements dramatically decrease the bone mineral density loss that occurs for five to ten years after menopause. This effect is improved if the patient also takes calcium supplements. Over longer time periods, however, estrogen supplements cannot completely stop the normal bone mineral density loss that occurs with aging. Based on information of this type, the software projects the type and rate of bone mineral density loss throughout the lifespan of a given woman for both situations, taking estrogen replacement versus not.

Disease Progression Explorer 17 contains a large amount of encoded expert knowledge, especially if it is not configured in a system with any of the other Explorers that generate the data for its use. Because of the large amount of expert knowledge embedded in the code, the development of Disease Progression Explorer 17 resembles the development of a knowledge-based/expert system. The software development process involves translating the expert knowledge of disease progression into knowledge base. Any of a number of standard representational methodologies can be used, e.g., production rules, frames, semantic networks, conditional branching, case structures, and the like. This translation process is well known in the art.

CONCLUSION

The above description of the preferred embodiment has been given by way of illustration only and numerous other embodiments of the subject invention may become apparent to those skilled in the art upon consideration of the above description and the attached drawings. Accordingly, limitations on the scope of the subject invention are to be found only in the claims set forth below.

What is claimed is:

1. A computer assisted method of identifying a proposed intervention for a disease, comprising the computer assisted steps of:

storing a database of biological data relating changes in biological systems to changes in disease progression of the disease, the biological data including:
data relating intercellular, intracellular, and organic changes in a biological system to changes in disease progression for a standard intervention;
patient attributes of a plurality of patient types;
intervention attributes of a plurality of interventions;
biology attributes of cellular changes or cellular attributes associated with each intervention; and
disease progression measures for a disease;

receiving user inputs of biologic parameters of a biological system;

constructing a query from the user inputs;

querying a data source with the query to determine values of disease progression measures associated with the biologic parameters, the disease progression measures selectively including:
cellular behavior parameters;
intermediate biological disease progression measures; and
clinically observable disease progression measures;

displaying the values of the disease progression measures; and systematically querying of the data source with user input changes in the biologic parameters associated with standard interventions to identify the proposed intervention that produces disease progression measures indicative of an effective alteration of the disease.

2. A computer assisted method of designing a clinical trial for a proposed intervention for a disease, comprising the computer assisted steps of:

receiving data relating disease progression for selected patient types to different interventions with respect to clinical symptoms;

receiving an input of a proposed clinical trial design defined by a user selected of intervention attributes of a proposed intervention and patient attributes that are to be controlled during the proposed clinical trial;

producing a disease progression of values of disease progression measures for each of the proposed interventions for each of a plurality of patient types having different patient attributes by:

receiving patient attributes for a single patient of a selected patient type;

determining values of disease progression measures for the patient as a function of the patient attributes and the proposed intervention and standard interventions; and displaying the values of the disease progression measures and patient attributes for each of the interventions, to assist in identifying patient attributes for which the proposed intervention provides an efficacious result on the disease progression relative to other interventions.

3. The method of claim 2, wherein the disease progression measures include at least one of:

cellular data descriptive of disease progression;

intermediate biologic data descriptive of the disease progression; and clinically observable symptoms of the disease progression.

4. The method of claim 2, further comprising:

storing an expert knowledge base relating values of disease progression measures to selected anatomical representations of clinically observable symptoms of disease progression on a human body;

selecting from the knowledge base at least one anatomical representation of the disease progression measures in response to the patient attributes; and graphically displaying the selected anatomical representation(s) of the disease progression measures.

5. The method of claim 2, wherein determining values of disease progression measures further comprises:

receiving patient attribute data for a plurality of patient attributes;

displaying a plurality of factorial combinations of the patient attributes, each factorial combination representing patient attributes of a single patient type;

for each of the plurality of factorial combinations of patient attributes:

querying a data source to retrieve values of disease progression measures for the combination of patient attributes; and selectively displaying the values of the disease progression measures for patient attributes.

6. The method of claim 5, further comprising:

displaying correlations between the plurality of patient attributes and the plurality of disease progression data retrieved from the data source.

7. A computer assisted method of determining a disease progression for a proposed intervention for a disease, comprising the computer assisted steps of:

providing a database of a disease progression information relating changes in disease progression measures of changes in subcellular, cellular, organ, anatomical, or clinical attributes with respect to time and to patient attributes;

receiving a user input of specified patient attributes of a patient;

receiving disease progression measures of the disease, including a time period for projecting the disease progression for the patient;

determining from the database, the disease progression for the time period as a function of the patient attributes, and the disease progression measures; and displaying the disease progression as changes in subcellular, cellular, tissue, or anatomical attributes of the patient.

8. The method of claim 7, wherein displaying the disease progression further comprises:

displaying the disease progression on an anatomical model of the body, showing disease progression over the time period.

9. The method of claim 7, further comprising:

providing a plurality of disease progression tutorials for the disease;

receiving patient attributes for a patient;

receiving intervention data for the proposed intervention;

receiving a user selection of a disease progression tutorial from the plurality of disease progression tutorials; and displaying the selected disease progression tutorial.

10. The method of claim 7, further comprising:

graphically displaying the disease progression for a patient having the specified patient attributes.

11. A computer assisted method of developing an intervention for a disease, comprising the computer assisted steps of:

storing a database of biologic parameters of biological systems, disease progression measures, patient attributes, and intervention data;

receiving an input of a proposed clinical trial design defined by a user selected plurality of intervention attributes and patient attributes that are to be controlled during the proposed clinical trial;

automatically and successively altering the biologic parameters of selected biological systems and querying the database to identify a proposed intervention that affects or measures the disease progression; and automatically and successively altering patient attributes, biologic parameters, and intervention attributes from the user selected set, and querying the database to determine a database outcome of the proposed clinical trial in terms of relationships between patient attributes, interventions, and disease progression measures.

12. The method of claim 11, further comprising:

specifying patient attributes and intervention data, and a time period for a disease progression; and projecting from the database, disease progression measures over the time period as a function of the patient attributes and intervention data.

13. The method of claim 11, further comprising:

receiving at least one of patient attributes, practitioner attributes, and payer attributes; and determining for a proposed intervention a pharmacoeconomic analysis of economic benefits of the proposed intervention relative to at least one standard intervention.

14. The method of claim 11, wherein identifying from the biological data a proposed intervention, further comprises:

receiving user inputs of biologic parameters of a biological system;

constructing a query from the user inputs;

querying a data source with the query to determine values of disease progression measures associated with the biologic parameters;

displaying the values of the disease progression measures; and systematically querying of the data source with user input changes in the biologic parameters associated with standard interventions to identify the proposed intervention that produces disease progression measures indicative of an effective alteration of the disease.

15. The method of claim 14, wherein the disease progression measures are displayed as an animated sequence of images.

16. The method of claim 14, further comprising:

inferring disease progression measures associated with the input biologic parameters in response to the input biologic parameters not matching biologic parameters in the data source.

17. A computer assisted method of developing an intervention for a disease, comprising the computer assisted steps of:

identifying, from biological data of a disease progression, a proposed intervention that affects or measures the disease progression;

designing a clinical trial of the proposed intervention by analysis of a factorial combination of intervention attributes and patient attributes to determine a disease progression of the disease for a selected patient type receiving the proposed intervention;

estimating economic costs and benefits of the proposed intervention relative to standard interventions by analysis of economic and non-economic intervention costs and benefits associated with disease progression for the proposed intervention relative to economic and non-economic intervention costs and benefits associated with the disease progression for the standard interventions; and displaying a disease progression over a specified time period for a selected patient attributes.

18. A computer assisted method of developing an intervention for a disease, comprising the computer assisted steps of:

identifying, from biological data of a disease progression, a proposed intervention that affects or measures the disease progression;

determining clinical trial data of the disease progression of the disease for a selected patient type receiving the proposed intervention by analysis of a factorial combination of intervention attributes of the proposed intervention and patient attributes; and producing for the proposed intervention a pharmacoeconomic analysis of economic benefits of the proposed intervention relative to other interventions by analysis of economic and non-economic intervention costs and benefits associated with disease progression for the proposed intervention relative to economic and non-economic intervention costs and benefits associated with the disease progression for the standard interventions.

19. The method of claim 18, further comprising:

creating a disease progression that describes a progression of the disease for user specified patient attributes, to assist practitioners in providing the proposed intervention to a patient having the specified patient attributes.

20. A computer assisted method for therapy data analysis and creation comprising:

storing information related to therapy data for therapies and disease data for diseases, the information including one or more biologic parameters related to the therapies and biology changes from disease progression in the diseases in response to the therapies; and receiving in a therapy discovery explorer one or more biologic parameters and analyzing the biologic parameters to create therapy data for a therapy for a disease, the therapy data relating biology change from the therapy to disease progression in the disease.

21. A computer system for assisting in the development of an intervention for a disease, comprising:

a database storing:
biological data for biological systems related to the disease;
patient type data for patients having the disease;
economic data for standard interventions applied to the disease, and
clinical data of clinical trials of standard interventions;

a target discovery module, coupled to the database to receive the biological data and patient type data, to identify a proposed intervention and produce first intervention data of effects of the proposed intervention on measures of disease progression;

a clinical trials module, coupled to the database and the target discovery module, to receive the patient type data, the first intervention data, and second intervention data of effects of standard interventions on the disease progression, and to produce clinical trial data relating selected patient populations having specific patient attributes, and disease progression for each patient type to identify patient types for which the proposed intervention has a clinically efficacious effect for inclusion in a clinical trial of the proposed intervention;

a pharmacoeconomic module, coupled to the database, and the clinical trials module, to receive the patient type data, and the economic data, to produce a pharmacoeconomic analysis of economic costs and benefits of the proposed intervention for a selected patient type relative to standard interventions; and a disease progression module, coupled to the database to receive the biological data and patient type data, to produce, for at least one patient type having specified patient attributes, a description of disease progression in the patient type over a user specified time period.

22. The system of claim 21, further comprising:

a results database for storing intermediate result data, including:
patient attributes;
intervention attributes, for both standard interventions and the proposed intervention;
disease progression measures for the standard interventions and the proposed intervention over time, the disease progression measures selectively including cellular data and clinically observable symptoms;
cost data for the standard intervention and the proposed intervention for patients and for payers; and
pharmacoeconomic outcome data for selected patients or patient populations, practitioners, and payers.

23. The system of claim 21, wherein the pharmacoeconomic outcome data further comprises:
  estimated cost of future treatments for the standard interventions and the proposed intervention;
  quality of life data for the standard interventions and the proposed intervention; and
  practice based results to the practitioner for providing either standard interventions or the proposed intervention.

24. A computer system for describing and presenting disease progression measures resulting from a proposed intervention for a disease, comprising:
  a database storing:
    biological data for biological systems related to the disease;
    patient type data for patients having the disease;
    disease progression measures for the disease of changes in subcellular, cellular, organ, anatomical, or clinical attributes over time for various interventions as applied to the disease in different types of patients; and
  a disease progression module, coupled to the database to receive the biological data, a proposed one of the interventions, and selected patient type data, to produce, for at least one patient type having specified patient attributes, a graphic presentation of a projection of disease progression measures of the disease over time in the selected patient type resulting from the proposed intervention.

25. The system of claim 24, wherein the disease progression module further comprises:
  a patient history module for receiving patient attributes of a patient and retrieving values for disease progression measures from the database descriptive of disease progression in the patient.

26. The system of claim 24, wherein the disease progression module further comprises:
  a disease progression evaluation module that receives patient attributes for a patient, intervention data for the proposed intervention, and a time period for projecting the disease progression measures in the patient, and that displays the disease progression measures over the time period for the patient based on the patient attributes, the disease progression measures, and the intervention data.

27. The system of claim 26, wherein the disease progression evaluation module displays the disease progression on an anatomical representation of a human body or portion thereof.

28. An apparatus for therapy data analysis and creation comprising:
  a data/information source for storing information related to therapy data and disease data, the stored information including one or more biologic parameters related to therapies and biology changes from disease progression in response to the therapies;
  a process interface for accessing the data/information source to obtain biologic parameters; and
  a therapy discovery explorer for receiving biologic parameters from the process interface and for analyzing the biologic parameters to create therapy data for a therapy, the therapy data relating biology change from the therapy to disease progression.

29. The apparatus according to claim 28, wherein the therapy discovery explorer comprises a biologic manipulation tool for producing one or more profiles of disease progression based on the one or more biologic parameters.

30. The apparatus according to claim 29, wherein the biologic manipulation tool queries the data/information source based on the one or more biologic parameters to produce the one or more profiles of disease progression.

31. The apparatus according to claim 29, wherein the biologic manipulation tool comprises a graphical user interface for entering the biologic parameters.

32. The apparatus according to claim 28, wherein the therapy discovery explorer further comprises a disease progression evaluation facility for analyzing disease progression based at least in part on information retrieved by the biologic manipulation tool from the data/information source and for developing information relating biology change and disease change.

33. The apparatus according to claim 28, wherein the therapy discovery explorer comprises a disease progression evaluation facility for analyzing one or more profiles of disease progression and developing the information relating biology change and disease change based on the profiles.

34. The apparatus according to claim 33, wherein the disease progression evaluation facility comprises target treatment development support for identifying at least one therapy.

35. The apparatus according to claim 33, wherein the disease progression evaluation facility comprises a user interface element for creating a display of the information relating biology change and disease change.

36. The apparatus of claim 28, wherein:
  the data/information source further comprises a database storing:
    biological data for biological systems related to the disease;
    patient type data for patients having the disease; and
  the therapy discovery explorer is coupled to the database to receive the biological data and patient type data, to identify a proposed intervention and produce intervention data of effects of a proposed intervention on measures of disease progression.

37. The apparatus of claim 36, wherein the therapy discovery explorer further comprises:
  a biological manipulation tool for qualitatively or quantitatively altering biological parameters of a biological system to determine changes in disease progression measures; and
  a biological change evaluation tool for displaying relationships between alterations in biological parameters and resulting changes in disease progression measures.

38. The apparatus of claim 37, wherein:
  the biological manipulation tool:
    receives user inputs of biological parameters of a biological system;
    constructs a query from the user inputs;
    queries a data source with the query to determine values of the disease progression measures associated with the biological parameters; and
  the biological change evaluation tool displays the values of the disease progression measures in relationship to the input biological parameters.

39. The apparatus of claim 38, wherein:
  the data/information source comprises a database storing:
    biologic parameters for biological systems related to a disease;
    disease progression measures for the disease over time;
    patient attribute data for various patient types having the disease;

intervention data descriptive of standard interventions and a proposed intervention; and the clinical trials explorer is coupled to the database, to receive selected patient attributes, selected biologic parameters, and selected intervention data, for querying the database to identify combinations of patient attributes and intervention for which the proposed intervention has a clinically efficacious effect on the disease progression measures, for designing a clinical trial of selected patient attributes, biologic parameters, and intervention data.

40. The apparatus of claim 39, wherein the clinical trials explorer further comprises:

a patient type efficacy module that receives the patient attributes for a single patient type, and outputs the disease progression measures for the patient type as a function of each of a plurality of interventions, including the proposed intervention and other interventions; and a clinical trial design module that receives a plurality of distinct patient attributes, biological parameters, and intervention data, and queries the database with respect selected combinations of patient attributes, each selected combination of patient attributes representing a patient type, to determine disease progression measures for each patient type and an intervention.

41. The apparatus of claim 40, wherein the patient type efficacy module further comprises:

a clinical visualization module that receives patient attributes for a plurality of patient types and selected disease progression measures, and outputs an anatomical representation of disease progression for the selected ones of the disease progression measures and patient types as a function of the proposed intervention.

42. The apparatus of claim 40, wherein the clinical trial design module further comprises:

a trial analysis tool that receives values of selected disease progression measures, for the plurality of patient attributes, and determines and displays correlations between individual ones of the patient attributes and selected disease progression measures.

43. An apparatus for clinical trial data analysis and creation comprising:

a data/information source for storing information related to therapy data, patient data, and patient type information, the information including one or more biologic parameters related to therapies and biology changes from disease progression in response to the therapies, therapy data, and patient type information;

a process interface for accessing the data/information source to obtain biologic parameters, therapy data and patient type information; and a clinical trials explorer for receiving biologic parameters, therapy data, and patient type information from the process interface and for analyzing the biologic parameters, therapy data, and patient type information to create clinical trial data including disease progression information from biology changes for the patient type and a therapy.

44. The apparatus according to claim 43, wherein the clinical trials explorer includes: a patient type efficacy module for receiving patient type information and developing disease progression information based on the patient type information.

45. The apparatus according to claim 43, wherein the clinical trials explorer comprises a visualization component for displaying patient type disease progression information from rules-based analysis.

46. The apparatus according to claim 43, wherein the clinical trials explorer includes, a clinical trial design suite for determining one or more disease outcomes for one or more patient types over a specified period of time with respect to at least one therapy.

47. The apparatus according to claim 46, wherein the clinical trial design suite comprises a study design tool for developing information relating patient types and disease progression based on analysis variables.

48. The apparatus according to claim 46, wherein the clinical trial design suite comprises a trial analysis tool for developing correlations between patient variables and disease outcomes.

49. An apparatus for therapy outcome data analysis and creation comprising:

a data/information source for storing information related to therapy data for therapies, biology change from therapies, and economic and non-economic outcomes of therapies;

a process interface for accessing the data/information source to obtain the stored information; and a pharmacoeconomic explorer for receiving the stored information from the process interface and for performing an effectiveness analysis on the received information to determine an effectiveness of a therapy as a result of biology changes from the therapy and economic and non-economic outcomes of the therapy.

50. The apparatus according to claim 49, wherein the pharmacoeconomic explorer includes at least one outcome analyzer for comparing a proposed therapy to current standard therapy for a particular constituent.

51. The apparatus according to claim 50, wherein the pharmacoeconomic explorer receives information characterizing clinical trial results to support the outcome analyzer.

52. The apparatus according to claim 49, wherein the pharmacoeconomic explorer includes, at least one outcome analyzer for developing information relating a therapy to a particular constituent outcome.

53. The apparatus according to claim 52, wherein the pharmacoeconomic explorer receives information characterizing clinical trial results to support the outcome analyzer.

54. The apparatus of claim 49 wherein:

the data/information source comprises a database storing:
patient type data for patients having the disease;
economic data for a plurality of standard interventions and the proposed intervention as applied to the disease;
disease progression measures for the disease for the plurality of standard interventions and the proposed intervention as applied to disease; and the pharmacoeconomic explorer is coupled to the database to receive the patient type data, the economic data, and the disease progression data, to produce a pharmacoeconomic analysis of economic costs and benefits of the proposed intervention for a selected patient type relative to the standard interventions.

55. The apparatus of claim 54, wherein the pharmacoeconomic explorer further comprises:

a patient outcome analysis module that receives patient attributes for a patient type, disease attributes for a disease, and intervention data of the proposed intervention, and determines a patient outcome, including an estimated cost of the proposed intervention to the patient and a quality of life value for the patient type receiving the proposed intervention.

56. The apparatus of claim 54, wherein the pharmacoeconomic explorer further comprises:

a practitioner outcome analysis module that receives practitioner attributes for a practitioner providing the proposed intervention, and patient attributes for a patient type receiving the proposed intervention, and determines a practitioner outcome as a result of providing the proposed intervention to the patient type.

57. The apparatus of 54, wherein the pharmacoeconomic explorer further comprises:

a payer outcome analysis module that receives intervention data of the proposed intervention, future treatment data for the proposed intervention, and payer attributes of a payer providing payment for the proposed intervention, and determines a payer outcome, including an estimated cost of the proposed intervention to the payer.

58. A system for biological data analysis used in developing, testing and evaluating therapies for a disease, comprising:

at least two distinct data/information sources storing information related to at least one disease, various interventions for the at least one disease, including standard interventions, and disease progression information for at least one disease from the interventions; and a pharmacoeconomic explorer interface integrating data received from the at least two distinct data/information sources to provide an outcome analysis of a proposed one of the interventions for a disease compared to standard interventions for the disease.

59. The system according to claim 58, wherein the at least two distinct data/information sources are chosen from the group consisting of expert knowledge databases, historical databases, clinical trial results, and computer models.

60. The system according to claim 58, wherein results produced by the pharmacoeconomic clinical trials explorer interface are a distinct data/information source which may be used by a second interface in providing reliably appraised data of a desired biological system.

61. An apparatus for therapy analysis and creation comprising:

a process interface for accessing an information source storing biological information of biological systems, the information including therapy data for therapies, biologic parameters related to the therapies and biology changes from disease progression in response to the therapies, patient type information, and economic and non-economic outcomes of the therapies, the process interface communicatively coupled to at least two explorers selected from a group consisting of:

a therapy discovery explorer that receives selected biologic parameters from the information source and develops therapy data relating biology changes to disease changes from a disease by selective alteration of biological parameters;

a clinical trials explorer that receives patient type information and therapy data, and biological parameters from the information source and develops disease progression data for the patient type and therapy therefrom; and a pharmacoeconomic explorer that develops outcome data of a proposed therapy compared to at least one standard therapy.

62. The apparatus of claim 61, further comprising:

an information source including a plurality of different information sources, each information source providing a different type of information, including at least one of biological information, pharmaceutical information, or clinical information, economic information, or therapy information.

63. The apparatus of claim 62, wherein the plurality of information sources include at least two information sources from the group comprising:

an expert knowledge database;

a historical literature database;

a clinical trials results database; and a computer model.

64. The apparatus of claim 62, wherein at least one of the explorers receives and processes data from at least two different information sources to develop its data.

65. The apparatus of claim 62, including at least two of the explorers, wherein the data developed by one of the explorers is an information source used by another explorer to develop its respective data.

* * * * *